US012806209B2

(12) United States Patent
Salgia et al.

(10) Patent No.: US 12,806,209 B2
(45) Date of Patent: Nov. 24, 2026

(54) COMBINATION THERAPY FOR TREATMENT OF CANCER

(71) Applicant: CITY OF HOPE, Duarte, CA (US)

(72) Inventors: Ravi Salgia, Pasadena, CA (US); Tamara Mirzapoiazova, Monrovia, CA (US); Steven Rosen, Pasadena, CA (US)

(73) Assignee: CITY OF HOPE, Duarte, CA (US)

( * ) Notice: Subject to any disclaimer, the term of this patent is extended or adjusted under 35 U.S.C. 154(b) by 292 days.

(21) Appl. No.: 18/784,488

(22) Filed: Jul. 25, 2024

(65) Prior Publication Data

US 2025/0041313 A1 Feb. 6, 2025

Related U.S. Application Data

(60) Provisional application No. 63/515,790, filed on Jul. 26, 2023.

(51) Int. Cl.

| | |
|---|---|
| ***A61K 31/555*** | (2006.01) |
| ***A61K 31/277*** | (2006.01) |
| ***A61K 31/42*** | (2006.01) |
| ***A61K 31/4995*** | (2006.01) |
| ***A61K 31/7048*** | (2006.01) |
| ***A61P 35/00*** | (2006.01) |
| *A61K 39/00* | (2006.01) |

(52) U.S. Cl.

CPC .......... *A61K 31/555* (2013.01); *A61K 31/277* (2013.01); *A61K 31/42* (2013.01); *A61K 31/4995* (2013.01); *A61K 31/7048* (2013.01); *A61P 35/00* (2018.01); *A61K 2039/505* (2013.01)

(58) Field of Classification Search

CPC .... A61K 31/555; A61K 31/277; A61K 31/42; A61K 31/4995; A61K 31/7048; A61K 2039/505; A61P 35/00

See application file for complete search history.

(56) References Cited

PUBLICATIONS

Jiang et al., Anti-inflammatory drug, leflunomide and its metabolite teriflunomide inhibit NSCLC proliferation in vivo and in vitro, 282 Toxicology 154-165 (2018). (Year: 2018).*

Alfaro-Lara, R. et al. (May-Jun. 2019). "Systematic review and meta-analysis of the efficacy and safety of leflunomide and methotrexate in the treatment of rheumatoid arthritis," *Reumatol Clin (Engl Ed)* 15(3):133-139.

American Cancer Society. Cancer Facts & Figures (2022). Located at <https://www.cancer.org/content/dam/cancer-org/research/cancer-facts-and-statistics/annual-cancer-facts-and-figures/2022/2022-cancer-facts-and-figures.pdf> 80 pages.

Cheng, L. et al. (May 18, 2020). "Leflunomide Inhibits Proliferation and Induces Apoptosis via Suppressing Autophagy and PI3K/Akt Signaling Pathway in Human Bladder Cancer Cells," *Drug Des Devel Ther* 14:1897-1908.

Hu, J. et al. (Feb. 19, 2020). "ROCK1 activation-mediated mitochondrial translocation of Drp1 and cofilin are required for arnidiol-induced mitochondrial fission and apoptosis," *J Exp Clin Cancer Res* 39(1):37.

Kundu, K. et al. (Nov. 2021). "SLFN11 biomarker status predicts response to lurbinectedin as a single agent and in combination with ATR inhibition in small cell lung cancer," *Transl Lung Cancer Res* 10(11):4095-4105.

Lennon, F.E. et al. (Apr. 15, 2016). "Unique fractal evaluation and therapeutic implications of mitochondrial morphology in malignant mesothelioma," *Sci Rep* 6:24578.

Lennon, F.E. et al. (May 2014). "Mitochondrial dynamics: biology and therapy in lung cancer," *Expert Opin Investig Drugs* 23(5):675-692.

Liao, Y. et al. (Apr. 4, 2013). "The Subread aligner: fast, accurate and scalable read mapping by seed- and-vote," *Nucleic Acids Res* 41(10):e108.

Liguori, N.R. et al. (Feb. 15, 2022). "Preclinical studies with ONC201/TIC10 and lurbinectedin as a novel combination therapy in small cell lung cancer (SCLC)," *Am J Cancer Res* 12(2):729-743.

Love, M.I. et al. (2014). "Moderated estimation of fold change and dispersion for RNA-seq data with DESeq2," *Genome Biol* 15(12):550.

Miret-Casals, L. et al. (Mar. 15, 2018). "Identification of New Activators of Mitochondrial Fusion Reveals a Link between Mitochondrial Morphology and Pyrimidine Metabolism," *Cell Chem Biol* 25(3):268-278e4.

Mirzapoiazova, T. et al. (Oct. 18, 2019). "Monitoring and Determining Mitochondrial Network Parameters in Live Lung Cancer Cells," *J Clin Med* 8(10):1723.

Mirzapoiazova, T. et al. (Oct. 2021). "Protein Phosphatase 2A as a Therapeutic Target in Small Cell Lung Cancer," *Mol Cancer Ther* 20(10):1820-1835.

Mirzapoiazova, T. et al. (Oct. 2024). MA19.04 "Teriflunomide in Vitro or Leflunomide in Vivo Treatment Increases the Efficacy of Lurbinectedin in SCLC," *J Thorac Oncol* 19(10S): S134.

Murray, N. et al. (2006). "A review of first-line treatment for small-cell lung cancer," *J Thorac Oncol* 1(3):270-278.

Picard, M et al. (Jan. 2021). "The social nature of mitochondria: Implications for human health," *Neurosci Biobehav Rev* 120:595-610.

Poroyko, V. et al. (Apr. 13, 2018). "Exosomal miRNAs species in the blood of small cell and non-small cell lung cancer patients," *Oncotarget* 9(28):19793-19806.

Powell, H.A. et al. (Feb. 18, 2014). "Treatment decisions and survival for people with small-cell lung cancer," *Br J Cancer* 110(4):908-915.

Rehman, J. et al. (May 2012). "Inhibition of mitochondrial fission prevents cell cycle progression in lung cancer," *Faseb J* 26(5):2175-2186.

Rudin, C.M. et al. (Dec 1, 2015). "Treatment of Small-Cell Lung Cancer: American Society of Clinical Oncology Endorsement of the American College of Chest Physicians Guideline," *J Clin Oncol* 33(34):4106-4111.

Santamaria Nunez, G. et al. (Oct. 2016). "Lurbinectedin Specifically Triggers the Degradation of Phosphorylated RNA Polymerase II and the Formation of DNA Breaks in Cancer Cells," Mol Cancer Ther 15(10):2399-2412.

Shaul, Y.D. et al. (Aug. 28, 2014). "Dihydropyrimidine accumulation is required for the epithelial-mesenchymal transition," *Cell* 158(5):1094-1109.

(Continued)

*Primary Examiner* — Timothy R Rozof

(74) *Attorney, Agent, or Firm* — Mintz, Levin, Cohn, Ferris, Glovsky and Popeo, P.C.

(57) ABSTRACT

Described herein, inter alia, are combination therapies for the treatment of lung cancer.

12 Claims, 39 Drawing Sheets

Specification includes a Sequence Listing.

(56) References Cited

PUBLICATIONS

Subbiah, S. et al. (2020). "Small Cell Lung Cancer from Traditional to Innovative Therapeutics: Building a Comprehensive Network to Optimize Clinical and Translational Research," *J Clin Med* 9:2433.
Trigo, J. et al. (2020). "Lurbinectedin as second-line treatment for patients with small-cell lung cancer: a single-arm, open-label, phase 2 basket trial," *Lancet Oncol* 21(5):645-654.

* cited by examiner

| SBC3 Data for Fa=0.5 | CI value | Teriflunomide μM | Carboplatin μM |
|---|---|---|---|
| Teriflunomide | | 4.25 | |
| Carboplatin | | | 4.12 |
| Combination | 0.669 | 1.4 | 1.4 |

| cells | substance | syn_p | teri_p | carb_p |
|---|---|---|---|---|
| SBC3 | UTP | 0.029* | 0.666 | 0.186 |
| SBC3 | dm5UTP | 0.005* | 0.666 | 0.009* |
| SBC3 | dCTP | 0.026* | 0.076 | 0.106 |
| SBC3 | ITP | 0.029* | 0.344 | 0.286 |
| SBC3 | TTP/dTDP | 0.005* | 0.670 | 0.009* |
| SBC3 | GTP | 0.046* | 0.960 | 0.270 |
| SBC3 | XMP | 0.046* | 0.001* | 0.012* |
| SBC3 | Xanthosine | 0.005* | 0.000* | 0.002* |
| SBC3 | ATP | 0.029* | 0.383 | 0.320 |
| SBC3 | dATP | 0.005* | 0.042* | 0.012* |

| substance | Metabolite |
|---|---|
| UTP | Pyrimidine |
| dm5UTP | Pyrimidine |
| dCTP | Pyrimidine |

| substance | Metabolite |
|---|---|
| ITP | Purine |
| TTP/dTDP | Purine |
| GTP | Purine |
| XMP | Purine |
| Xanthosine | Purine |

| substance | Metabolite |
|---|---|
| ATP | Purine/Pyrimidine |
| dATP | Purine/Pyrimidine |

| Data for Fa=0.5 | CI | Teri nM | Lur pM |
|---|---|---|---|
| Teriflunomide | | 1.19E+07 | |
| Lurbinectedin | | | 14375.3 |
| Combination | 0.3 | 4315 | 4315 |

| Data for Fa=0.5 | CI | Teri nM | Lur pM |
|---|---|---|---|
| Teriflunomide | | 4.75E+05 | |
| Lurbinectedin | | | 3.15E+07 |
| Combination | 0.0072 | 3363.84 | 3363.84 |

DLT = Dose Limiting Toxicity

MTD = Maximum Tolerable Dose

SEQUENCE LISTING

```
Sequence total quantity: 11
SEQ ID NO: 1            moltype = AA  length = 736
FEATURE                 Location/Qualifiers
REGION                  1..736
                        note = Synthetic polypeptide
source                  1..736
                        mol_type = protein
                        organism = synthetic construct
SEQUENCE: 1
MEALIPVINK LQDVFNTVGA DIIQLPQIVV VGTQSSGKSS VLESLVGRDL LPRGTGIVTR  60
RPLILQLVHV SQEDKRKTTG EENGVEAEEW GKFLHTKNKL YTDFDEIRQE IENETERISG  120
NNKGVSPEPI HLKIFSPNVV NLTLVDLPGM TKVPVGDQPK DIELQIRELI LRFISNPNSI  180
ILAVTAANTD MATSEALKIS REVDPDGRRT LAVITKLDLM DAGTDAMDVL MGRVIPVKLG  240
IIGVVNRSQL DINNKKSVTD SIRDEYAFLQ KKYPSLANRN GTKYLARTLN RLLMHHIRDC  300
LPELKTRINV LAAQYQSLLN SYGEPVDDKS ATLLQLITKF ATEYCNTIEG TAKYIETSEL  360
CGGARICYIF HETFGRTLES VDPLGGLNTI DILTAIRNAT GPRPALFVPE VSFELLVKRQ  420
IKRLEEPSLR CVELVHEEMQ RIIQHCSNYS TQELLRFPKL HDAIVEVVTC LLRKRLPVTN  480
EMVHNLVAIE LAYINTKHPD FADACGLMNN NIEEQRRNRL ARELPSAVSR DKSSKVPSAL  540
APASQEPSPA ASAEADGKLI QDSRRETKNV ASGGGGVGDG VQEPTTGNWR GMLKTSKAEE  600
LLAEEKSKPI PIMPASPQKG HAVNLLDVPV PVARKLSARE QRDCEVIERL IKSYFLIVRK  660
NIQDSVPKAV MHFLVNHVKD TLQSELVGQL YKSSLLDDLL TESEDMAQRR KEAADMLKAL  720
QGASQIIAEI RETHLW                                                 736

SEQ ID NO: 2            moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 2
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                    448

SEQ ID NO: 3            moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 3
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 4            moltype = AA  length = 451
FEATURE                 Location/Qualifiers
REGION                  1..451
                        note = Synthetic polypeptide
source                  1..451
                        mol_type = protein
                        organism = synthetic construct
SEQUENCE: 4
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
```

-continued

```
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 5           moltype = AA  length = 215
FEATURE                Location/Qualifiers
REGION                 1..215
                       note = Synthetic polypeptide
source                 1..215
                       mol_type = protein
                       organism = synthetic construct
SEQUENCE: 5
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 6           moltype = DNA  length = 20
FEATURE                Location/Qualifiers
misc_feature           1..20
                       note = Synthetic polynucleotide
source                 1..20
                       mol_type = other DNA
                       organism = synthetic construct
SEQUENCE: 6
caagtttagt gattacagct                                              20

SEQ ID NO: 7           moltype = DNA  length = 20
FEATURE                Location/Qualifiers
misc_feature           1..20
                       note = Synthetic polynucleotide
source                 1..20
                       mol_type = other DNA
                       organism = synthetic construct
SEQUENCE: 7
tcttgttgtt aatatctagc                                              20

SEQ ID NO: 8           moltype = DNA  length = 22
FEATURE                Location/Qualifiers
misc_feature           1..22
                       note = Synthetic polynucleotide
source                 1..22
                       mol_type = other DNA
                       organism = synthetic construct
SEQUENCE: 8
agtgggattg tagatgaggg tt                                           22

SEQ ID NO: 9           moltype = DNA  length = 20
FEATURE                Location/Qualifiers
misc_feature           1..20
                       note = Synthetic polynucleotide
source                 1..20
                       mol_type = other DNA
                       organism = synthetic construct
SEQUENCE: 9
tctcccttta gggcaacgga                                              20

SEQ ID NO: 10          moltype = DNA  length = 21
FEATURE                Location/Qualifiers
misc_feature           1..21
                       note = Synthetic polynucleotide
source                 1..21
                       mol_type = other DNA
                       organism = synthetic construct
SEQUENCE: 10
ctgagcgtga acgtggtatc a                                            21

SEQ ID NO: 11          moltype = DNA  length = 24
FEATURE                Location/Qualifiers
misc_feature           1..24
                       note = Synthetic polynucleotide
source                 1..24
                       mol_type = other DNA
                       organism = synthetic construct
SEQUENCE: 11
ggcagacagt actctatcaa ctca                                         24
```

COMBINATION THERAPY FOR TREATMENT OF CANCER

CROSS-REFERENCES TO RELATED APPLICATIONS

This application claims the benefit of U.S. Provisional Application No. 63/515,790, filed Jul. 26, 2023, which is incorporated herein by reference in its entirety and for all purposes.

REFERENCE TO AN ELECTRONIC SEQUENCE LISTING

The contents of the electronic sequence listing (048440-876001US_Sequence_Listing_ST26.xml; Size: 16,894 bytes; and Date of Creation: Jun. 25, 2024) is hereby incorporated by reference in its entirety.

BACKGROUND

Small cell lung cancer (SCLC) is an aggressive malignancy that leads to fatalities if left untreated. Most SCLC patients are diagnosed with metastatic disease and rapid tumor growth. Unfortunately, the clinical outcome of SCLC patients is poor due to early relapse and ineffective standard chemotherapy treatment options for recurrent tumors. Leflunomide and its active metabolite teriflunomide are inhibitors of pyrimidine synthesis that target DHODH resulting in anti-inflammatory and immunosuppressive activity. Leflunomide was identified as a new activator of mitochondrial fusion and revealed a link between mitochondrial morphology and pyrimidine metabolism. Recent studies showed the essential role of mitochondrial dynamics in tumorigenesis and cancer cell proliferation. Mitochondrial fragmentation and elongation are responsible for maintaining proper mitochondrial morphology. Dynamin-related protein (DRP1) is a key protein of mitochondrial fission and can be an attractive therapeutic target for SCLC. Disclosed herein, inter alia, are solutions to these and other problems in the art.

BRIEF SUMMARY

In an aspect is provided a method of treating small cell lung cancer in a subject in need thereof, the method including administering to the subject a combined effective amount of a first agent and a second agent, wherein the first agent is leflunomide or teriflunomide and the second agent is lurbinectedin, carboplatin, or cisplatin.

In an aspect is provided a kit including a combined effective amount of a first agent and a second agent, wherein the first agent is leflunomide or teriflunomide and the second agent is lurbinectedin, carboplatin, or cisplatin.

BRIEF DESCRIPTION OF THE DRAWINGS

FIGS. 1A-1B: Upregulation of DRP1 in human small cell carcinomas. Representative images of immunohistochemical staining of DRP1 in human small cell lung cancer tissue microarray. DRP1 immunostaining was observed to increase in intensity with disease progression. Regression analysis confirms significant positive correlation between DRP1 score and stage of tumor (p=0.002). Reference: Mirzapoiazova T, Li H, Nathan A, Srivstava S, Nasser M W, Lennon F, Armstrong B, Mambetsariev I, Chu P G, Achuthan S, Batra S K, Kulkarni P, Salgia R. Monitoring and Determining Mitochondrial Network Parameters in Live Lung Cancer Cells. J Clin Med. 2019 Oct. 18; 8(10):1723. doi: 10.3390/jcm8101723. PMID: 31635288; PMCID: PMC6832496). FIG. 1C: Representative immunoblots showing expression of DHODH and DRP1 in SCLC cell lines and non-malignant BEAS 2B cells (n=3 biological replicates).

FIG. 2A: Effect of Teri and Leflu on SBC3, and SBC5 cells proliferation was recorded by the Sartorius IncuCyte S3 live-cell analysis system (n=2, four technical replicates). Treatment of SBC3 and SBC5 cells with Leflu or Teri inhibited cell proliferation in a dose-dependent manner. FIG. 2B: Effect of Teri on DRP1 phosphorylation in SBC3 cells. Cell lysates were subjected to immunoblotting (n=3, biological replicates). FIG. 2C: The expression ratio of level of pDRP1 $Ser^{616}$ and $Ser^{637}$ to actin was calculated via densitometric analysis of each blot using ImageJ software. The detected ratio of pDRP1 $Ser^{616}$ to pDRP1 $Ser^{637}$ was calculated and compared in SBC3 cells. Teri significantly inhibited DRP1 phosphorylation at Ser616, and Ser637 however, DRP1 expression level was unaffected after treatment. FIGS. 2D-2E: Calculating pDRP1 $Ser^{616}$ fluorescence signal by QuPath software. Bar graphs mean±SE, *p<0.05; p<0.01; *p<0.001; **p<0.0001. Results were analyzed by ANOVA with Tukey post-test. FIG. 2F: The surface areas of SBC3 mitochondria and nuclei were quantified with Imaris Cells modules. The minimal number of SBC3 cells analyzed for each group was 103 (M1 10 μM), and the maximal was 383 (Control). FIG. 2G**: SBC5 mitochondria and nuclei surface areas were quantified with Imaris Cells modules. The minimal number of SBC5 cells analyzed for each group was 357 (MDIVI1 10 μM) and the maximal was 570 (Control). Results were analyzed by ANOVA with Tukey post-test, *p<0.05; p<0.01; p<0.0001. Mitochondria in control cells were closely packed around the nuclei and treatment with Teri rearranged the mitochondrial network and extended the area from the nuclei. FIG. 2H: Representative immunofluorescence (IF) images of mitochondria treated with teriflunomide, leflunomide, M1, and MDIVI1. SBC3 cells were treated with drugs for 18 hours, fixed with paraformaldehyde and subjected to IF staining with Tom 20 antibody, nuclei were stained with Hoechst 33342. Scale bar 10 μm. Right inserts represent shape of mitochondria for control and treatments. FIG. 2I**: High resolution confocal IF images of mitochondria in SBC5 cells. Scale bar 10 μm. Right inserts represent shape of mitochondria for control and treatments.

FIGS. 3B and 3D: Combination index (CI) was calculated using the Chou-Talalay method to find synergism. $IC_{50}$ isobologram after SBC3 and SBC5 cells treatment with Teri/Carbo. CI values at the 50% inhibition of cell proliferation were below 1, indicating a synergistic effect of Teri/Carbo on SBC3 (0.562) and an additive effect on SBC5 (1.02) cells. FIGS. 3E and 3F: SBC3/SBC5 relative wound density at different time points (% mean values+SD, monolayer wound measurements). Student's t test was used for statistical analysis, p<0.0001 (n=2, four technical replicates). FIG. 3G: The IncuCyte captured drug treatment effects on SBC3 spheroid growth. Upper panel shows data as mean values ±SD (n=2, four technical replicates). Lower panel displays representative brightfield images of SBC3 spheroid control and treatment. FIGS. 3H and 3J: Athymic nude mice were implanted with SBC3 and SBC5 cells and treated with vehicle (control), Carbo (50 mg/kg), Leflu (7.5 mg/kg), and Carbo/Leflu. Treatment with Carbo and Leflu alone caused a ~58% and ~36% reduction in tumor size, respectively. A much higher reduction of ~82% in tumor weight was observed in combinatorial treatment. The average wet weight of the tumor at day 40 (end of study) was significantly inhibited by Carbo/Leflu combination treatment. $p<0.0001$, Student's t test (five mice per group). FIGS. 3I and 3K: Control and treated FPPE mouse tumor sections (3 slides/tumor) were stained with phospho-DRP1 (Ser616) and counterstained with DAPI. Confocal images were acquired for each group (magnification: 100×). Mean signal intensities were measured with ZEN 2.3 Lite. Scale bar 100 μm. $p<0.01$; *$p<0.001$; **$p<0.0001$. Results were analyzed by ANOVA with Tukey post-test. Immunofluorescence staining of pDRP1 at Ser616 was significantly decreased with Leflu and Carbo treatment. Combination treatment more effectively inhibited DRP1 phosphorylation.

FIG. 4A: DRP1 phosphorylation response of SBC3 with the average relative density of pDRP1 $Ser^{616}$ and $Ser^{637}$ protein bands (n=3). FIG. 4B: Western blot images and band densitometry analysis of levels of apoptotic markers including cleaved PARP and p-p53 (n=3, biological replicates). FIG. 4C: Western blot images and band densitometry analysis of levels of DNA damage regulatory proteins. GAPDH was used as an internal control. Teri/Carbo treatment inhibited DRP1 phosphorylation at Ser616 suppressed mitochondrial fission and promoted apoptosis and DNA damage response in SCLC cells. Mitochondria are directly involved in the synthesis of intermediate cellular metabolites like purine and pyrimidine substances. FIG. 4D: Schematic diagram displays the effect of Teri/Carbo treatment on purine and pyrimidine pools in SBC3 cells. FIG. 4E: Statistical comparisons of drug treatments were performed to evaluate the synergistic effect of Teri/Carbo on the concentrations of pyrimidine/purine bases. The Table includes synergistically affected substances and p-values for three treatments of SBC3 cells. Ten significant synergistic p-values were detected by this approach. FIG. 4F: Three pyrimidine substances were significantly inhibited with Teri/Carbo treatment. UTP concentration significantly decreased (control 6.95±0.96; Teri 6.42±0.79; Carbo 9.29±0.4; Teri/Carbo 3.6±0.82 nmol/μg protein) and dm5UTP (control 0.24±0.03; Teri 0.26±0.01; Carbo 0.44±0.001; Teri/Carbo 0.15±0.03 nmol/μg protein), dCTP was increased (control 0.03±0.005; Teri 0.06±0.01; Carbo 0.06±0.004; Teri/Carbo 0.03±0.01 nmol/μg protein). FIG. 4G: Teri/Carbo treatment synergistically affected five purine substances. Highest significant inhibitory effect of Teri/Carbo was observed for two purine substances XMP (control 0.98±0.11; Teri 0.03±0.005; Carbo 0.35±0.18; Teri/Carbo 0.01±0.002 nmol/μg protein) and xanthosine (control 0.339±0.017; Teri 0.003±0.0003; Carbo 0.094±0.045; Teri/Carbo 0.001±0.0002 nmol/μg protein). FIG. 4H: Teri/Carbo significantly depleted the ATP pool: ATP (control 22.01±2.98; Teri 26.55±2.96; Carbo 27.92±0.55; Teri/Carbo 13.87±3.61 nmol/μg protein) and dATP (control 0.09±0.01; Teri 0.15±0.01; Carbo 0.17±0.002; Teri/Carbo 0.09±0.02 nmol/μg protein). Bars show synergistically significant substances. Significance was assessed with a linear model (ANOVA) see methods, *$p<0.05$; $p<0.01$. Our results showed that SCLC cells expressed high level of DRP1 and Teri/Carbo treatment inhibited cell proliferation in vitro and suppressed the growth of human lung cancer xenografts. FIG. 4I: Depletion of DRP1 by CRISPR Knockout significantly reduced colonies of cells by 80% (SBC3) and 40% (SBC5). Total clone number for SBC3 (DOX−/DOX+) and SBC5 (DOX−/DOX+) cells. Each CRISPR edited cell sample was sorted with single cell with DAPI into 3×96 well plates. The total visible clones were counted after 14 days incubation without DOX. $p<0.01$; *$p<0.001$. Results were analyzed by ANOVA with Tukey post-test. FIG. 4J: The NanoString differential expression analysis of gene patterns for SBC3 and SBC5 (DOX+ vs. DOX−), The dot plots were generated using the R ggplot2 package. FIG. 4**K: SBC3 and SBC5 expression pattern of public data set GSE1037. The normalized data from NIH Gene Expression Omnibus (GEO). SBC3, SBC5 and 19 normal samples from GSE1037 are used for the analysis to identify the different expression pattern of SBC3 and SBC5 (vs. normal) using the R LIMMA package (v 3.42.2). The differentially expressed genes are identified with FDR<0.05.

FIGS. 6A-6B: LDH cytotoxicity/death assay. The synergy of Teri/Lur was calculated by Chou-Talalay method. $IC_{50}$ Isobologram analysis indicated synergy for Teri/Lur doses below midline. Insert table shows $CI_{50}$ of treatment. FIGS. 6C-6D: H446 and SBC3 spheroid cell lysates were subjected to immunoblotting with RNA poly II and DNA damage markers antibodies (left panel), and DRP1, MFN2, and ERK antibodies (right panel). Lower panel (FIGS. 6C-6D) cell cycle regulatory antibody MDM2, p21, E2F1, CDK4 and cyclin D1 were used for Western blotting detection after 72 h of drug treatment (n=3, biological replicates). FIG. 6E: H446 spheroid MitoSOX production was detected and quantified with IncuCyte system (n=3, biological replicates). Bars shows the maximal level of MitoSOX in H446 spheroids after 44 h (control vs. Teri/Lur *$p<0.05$; $p<0.01$); and MitoSOX/brightfield images of spheroids. Scale bar 100 μm. FIG. 6F: Dose-response relative ATP measurement in H446 spheroids after 72 hours treatment with Teri, Lur and T-Lur (left panel, n=3). Significance between Lur and T-Lur treatments were assessed by Student's t-test, $p<0.01$; **$p<0.0001$ (right panel). FIG. 6G: Mitochondrial representative images: EL (elongated), R (round), ITM (intermediate) and CL (cluster) with Imaris Surface detections of individual mitochondria. Scale bar 0.3 μm. FIG. 6**H: Panels show the percentage of mitochondria from the total number based on length ratios of round, elongated, and ITM groups (control vs. Teri/Lur *$p<0.05$; $p<0.01$). The average number of cells 344-575 cells per group. FIG. 6I: In vivo efficacy of Leflu/Lur in mouse xenograft. Each value in graphline is the mean±SD from 5 mice per group (control vs. combination, $p<0.0001$). FIG. 6**J: Staining of mouse tumors with phospho-DRP1 (S616) antibodies (n=3, biological replicates). (*$p<0.05$; $p<0.01$). Scale bar 100 μm. FIG. 6K: Schematic diagram displays the effect of Leflu/Lur combination on purine/pyrimidine pools in mouse xenograft. FIGS. 6L-6M: Purine and pyrimidine substances measured by LC-MS/MS in tumors at the end of the study. Three pyrimidine and two purine substances were significantly decreased based on Student's t-test (control vs. Leflu/Lur, p<0.01; ***p<0.001).

FIG. 7A: The comparison of top enriched KEGG pathways for the different treatment expression profiles in three different treatments. FIG. 7B: The dot plot for these different expressed genes in Altered Cell Cycle Arrest, DNA damage and oxidative stress, and pro-apoptotic gene sets. The color of the dot represents the log 2 Fold Change compared between the treatment and control. The dot size represents the adjusted p-value. FIG. 7C: The GSEA plots for the top activated and top suppression KEGG pathways for each treatment.

DETAILED DESCRIPTION

I. Definitions

Figure 1A:
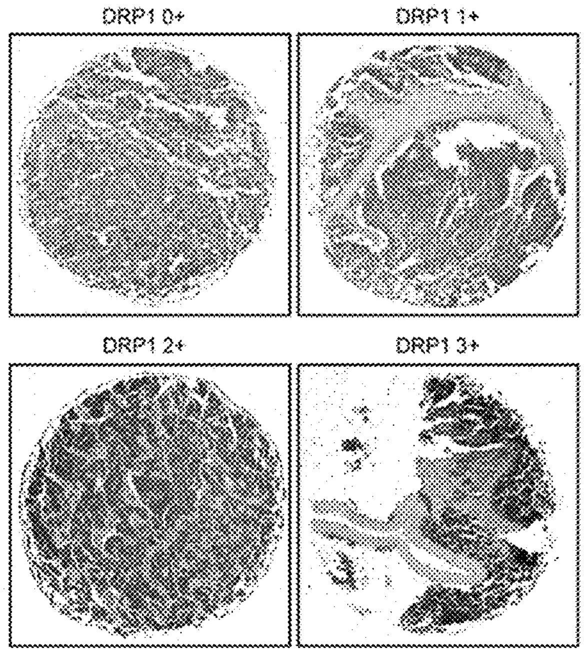
FIGS. 1A-1C. DRP1 expression in SCLC.

The abbreviations used herein have their conventional meaning within the chemical and biological arts. The chemical structures and formulae set forth herein are constructed according to the standard rules of chemical valency known in the chemical arts.

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, NY 1994); and Sambrook and Green, Molecular Cloning: A Laboratory Manual, 4th Edition (2012). Methods, devices and materials similar or equivalent to those described herein can be used in the practice of this invention.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

In this disclosure, "comprises", "comprising", "containing", and "having" and the like can have the meaning ascribed to them in U.S. Patent law and can mean "includes", "including", and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Contacting" is used in accordance with its plain ordinary meaning and refers to the process of allowing at least two distinct species (e.g., chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a cellular component (e.g., protein, ion, lipid, nucleic acid, nucleotide, amino acid, protein, particle, organelle, cellular compartment, microorganism, virus, lipid droplet, vesicle, small molecule, protein complex, protein aggregate, or macromolecule). In some embodiments contacting includes allowing a compound described herein to interact with a cellular component (e.g., protein, ion, lipid, nucleic acid, nucleotide, amino acid, protein, particle, virus, lipid droplet, organelle, cellular compartment, microorganism, vesicle, small molecule, protein complex, protein aggregate, or macromolecule) that is involved in a signaling pathway.

As defined herein, the term "activation," "activate," "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity by at least 10%, 20%, 30%, 40%, 50%, 60%, 70%, 80%, 90%, 95%, 96%, 97%, 98%, or 99% in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition," "inhibit," "inhibiting" and the like in reference to a cellular component-inhibitor interaction means negatively affecting (e.g., decreasing) the activity or function of the cellular component (e.g., decreasing the signaling pathway stimulated by a cellular component (e.g., protein, ion, lipid, virus, lipid droplet, nucleic acid, nucleotide, amino acid, protein, particle, organelle, cellular compartment, microorganism, vesicle, small molecule, protein complex, protein aggregate, or macromolecule)), relative to the activity or function of the cellular component in the absence of the inhibitor. In embodiments, inhibition means negatively affecting (e.g., decreasing) the concentration or levels of the cellular component relative to the concentration or level of the cellular component in the absence of the inhibitor. In some embodiments, inhibition refers to reduction of a disease or symptoms of disease. In some embodiments, inhibition refers to a reduction in the activity of a signal transduction pathway or signaling pathway (e.g., reduction of a pathway involving the cellular component). Thus, inhibition includes, at least in part, partially or totally blocking stimulation, decreasing, preventing, or delaying activation, or inactivating, desensitizing, or down-regulating the signaling pathway or enzymatic activity or the amount of a cellular component.

The terms "inhibitor," "repressor," "antagonist," or "downregulator" interchangeably refer to a substance capable of detectably decreasing the expression or activity of a given gene or protein. The antagonist can decrease expression or activity by at least 10%, 20%, 30%, 40%, 50%, 60%, 70%, 80%, 90%, 95%, 96%, 97%, 98%, or 99% in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "modulator" refers to a composition that increases or decreases the level of a target molecule or the function of a target molecule or the physical state of the target of the molecule (e.g., a target may be a cellular component (e.g., protein, ion, lipid, virus, lipid droplet, nucleic acid, nucleotide, amino acid, protein, particle, organelle, cellular compartment, microorganism, vesicle, small molecule, protein complex, protein aggregate, or macromolecule)) relative to the absence of the composition.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "associated" or "associated with" in the context of a substance or substance activity or function associated with a disease (e.g., a protein associated disease, disease associated with a cellular component) means that the disease (e.g., small cell lung cancer) is caused by (in whole or in part), or a symptom of the disease is caused by (in whole or in part) the substance or substance activity or function or the disease or a symptom of the disease may be treated by modulating (e.g., inhibiting or activating) the substance (e.g., cellular component). As used herein, what is described as being associated with a disease, if a causative agent, could be a target for treatment of the disease.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

"Disease" or "condition" refers to a state of being or health status of a patient or subject capable of being treated with the compounds or methods provided herein. In some embodiments, the disease is a disease related to (e.g., caused by) a cellular component (e.g., protein, ion, lipid, nucleic acid, nucleotide, amino acid, protein, particle, organelle, cellular compartment, microorganism, vesicle, small molecule, protein complex, protein aggregate, or macromolecule). In embodiments, the disease is a cancer. In embodiments, the disease is small cell lung cancer.

As used herein, the term "cancer" refers to all types of cancer, neoplasm or malignant tumors found in mammals (e.g., humans), including leukemia, lymphoma, carcinomas and sarcomas. Exemplary cancers that may be treated with a compound or method provided herein include cancer of the thyroid, endocrine system, brain, breast, cervix, colon, head and neck, liver, kidney, lung, non-small cell lung, melanoma, mesothelioma, ovary, sarcoma, stomach, uterus medulloblastoma, colorectal cancer, or pancreatic cancer. Additional examples include Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

The terms "polypeptide," "peptide," and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat a cancer (e.g., small cell lung cancer) by decreasing the incidence of the cancer (e.g., small cell lung cancer) and or causing remission of the cancer (e.g., small cell lung cancer). The term "treating" and conjugations thereof, include prevention of an injury, pathology, condition, or disease. In embodiments, treating is preventing. In embodiments, treating does not include preventing. In embodiments, the treating or treatment is not prophylactic treatment.

"Patient", "patient in need thereof", "subject", or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In embodiments, a patient is human. In embodiments, a patient in need thereof is human. In embodiments, a subject is human. In embodiments, a subject in need thereof is human.

An "effective amount" is an amount sufficient for a compound to accomplish a stated purpose relative to the absence of the compound (e.g., achieve the effect for which it is administered, treat a disease, reduce enzyme activity, increase enzyme activity, reduce signaling pathway, reduce one or more symptoms of a disease or condition. An example of an "effective amount" is an amount sufficient to contribute to the treatment, prevention, or reduction of a symptom or symptoms of a disease, which could also be referred to as a "therapeutically effective amount" when referred to in this context. A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. An "activity increasing amount," as used herein, refers to an amount of agonist required to increase the activity of an enzyme relative to the absence of the agonist. A "function increasing amount," as used herein, refers to the amount of agonist required to increase the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from binding assays or cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compound's effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

A "synergistic amount" or "synergistically effective amount" as used herein refers to the sum of a first amount (e.g., an amount of a compound provided herein) and a second amount (e.g., a therapeutic agent) that results in a synergistic effect (i.e., an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the compound provided herein when used separately from the therapeutic agent. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the therapeutic agent when used separately from the compound provided herein.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

In therapeutic use for the treatment of a disease, a compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of disease (e.g., small cell lung cancer) diagnosed in a particular patient. The dose administered to a patient, in the context of the present invention, should be sufficient to affect a beneficial therapeutic response in the patient over time. The size of the dose will also be determined by the existence, nature, and extent of any adverse side effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

As used herein, the term "administering" is used in accordance with its plain and ordinary meaning and includes oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

"Co-administer" is meant that a composition described herein is administered at the same time, just prior to, or just after the administration of one or more additional therapies. The compounds of the invention can be administered alone or can be co-administered to the patient. Co-administration is meant to include simultaneous or sequential administration of the compounds individually or in combination (more than one compound). Thus, the preparations can also be combined, when desired, with other active substances (e.g., to reduce metabolic degradation).

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example, mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g., signaling pathway) of a protein in the absence of a compound as described herein (including embodiments, examples, figures, or Tables).

The terms "bind" and "bound" as used herein is used in accordance with its plain and ordinary meaning and refers to the association between atoms or molecules. The association can be covalent (e.g., by a covalent bond or linker) or non-covalent (e.g., electrostatic interactions (e.g., ionic bond, hydrogen bond, or halogen bond), van der Waals interactions (e.g., dipole-dipole, dipole-induced dipole, or London dispersion), ring stacking (pi effects), hydrophobic interactions, and the like).

As used herein, the term "conjugated" when referring to two moieties means the two moieties are bonded, wherein the bond or bonds connecting the two moieties may be covalent or non-covalent. In embodiments, the two moieties are covalently bonded to each other (e.g., directly or through a covalently bonded intermediary). In embodiments, the two moieties are non-covalently bonded (e.g., through ionic bond(s), van der Waals bond(s)/interactions, hydrogen bond(s), polar bond(s), or combinations or mixtures thereof).

The term "drug" is used in accordance with its plain and ordinary meaning and refers to a substance that has a physiological effect (e.g., beneficial effect, is useful for treating a subject) when introduced into or to a subject (e.g., in or on the body of a subject or patient). A drug moiety is a radical of a drug.

The term "DRP1" or "dynamin-related protein 1" or "dynamin-1-like protein" refers to a protein that regulates mitochondrial fission. The term includes any recombinant or naturally-occurring form of DRP1 variants thereof that maintain DRP1 activity (e.g., within at least 30%, 40%, 50%, 60%, 70%, 80%, 90%, 95%, or 100% activity compared to wildtype DRP1). In embodiments, the DRP1 protein encoded by the DNM1L gene has the amino acid sequence set forth in or corresponding to Entrez 10059, UniProt 000429, RefSeq (protein) NP_001265392.1, RefSeq (protein) NP_001265393.1, RefSeq (protein) NP_001265394.1, RefSeq (protein) NP_001265395.1, RefSeq (protein) NP_001317309.1, RefSeq (protein) NP_005681.2, RefSeq (protein) NP_036192.2, or RefSeq (protein) NP_036193.2, or homolog thereof. In embodiments, the amino acid sequence or nucleic acid sequence is the sequence known at the time of filing of the present application. In embodiments, DRP1 has the sequence:

(SEQ ID NO: 1)

```
MEALIPVINKLQDVFNTVGADIIQLPQIVVVGTQSSGKSSVLESLVGRDL
LPRGTGIVTRRPLILQLVHVSQEDKRKTTGEENGVEAEEWGKFLHTKNKL
YTDFDEIRQEIENETERISGNNKGVSPEPIHLKIFSPNVVNLTLVDLPGM
TKVPVGDQPKDIELQIRELILRFISNPNSIILAVTAANTDMATSEALKIS
REVDPDGRRTLAVITKLDLMDAGTDAMDVLMGRVIPVKLGIIGVVNRSQL
DINNKKSVTDSIRDEYAFLQKKYPSLANRNGTKYLARTLNRLLMHHIRDC
LPELKTRINVLAAQYQSLLNSYGEPVDDKSATLLQLITKFATEYCNTIEG
TAKYIETSELCGGARICYIFHETFGRTLESVDPLGGLNTIDILTAIRNAT
GPRPALFVPEVSFELLVKRQIKRLEEPSLRCVELVHEEMQRIIQHCSNYS
TQELLRFPKLHDAIVEVVTCLLRKRLPVTNEMVHNLVAIELAYINTKHPD
FADACGLMNNNIEEQRRNRLARELPSAVSRDKSSKVPSALAPASQEPSPA
ASAEADGKLIQDSRRETKNVASGGGGVGDGVQEPTTGNWRGMLKTSKAEE
LLAEEKSKPIPIMPASPQKGHAVNLLDVPVPVARKLSAREQRDCEVIERL
IKSYFLIVRKNIQDSVPKAVMHFLVNHVKDTLQSELVGQLYKSSLLDDLL
TESEDMAQRRKEAADMLKALQGASQIIAEIRETHLW.
```

II. Methods

In an aspect is provided a method of treating small cell lung cancer in a subject in need thereof, the method including administering to the subject a combined effective amount of a first agent and a second agent, wherein the first agent is leflunomide or teriflunomide and the second agent is lurbinectedin, carboplatin, or cisplatin.

In an aspect is provided a method of treating small cell lung cancer in a subject in need thereof, the method including administering to the subject a combined effective amount of a first agent and a second agent, wherein the first agent is leflunomide or teriflunomide and the second agent is lurbinectedin or carboplatin.

In embodiments, the small cell lung cancer is extensive-stage small cell lung carcinoma. In embodiments, the small cell lung cancer is relapsed sensitive extensive-stage small cell lung carcinoma. In embodiments, the small cell lung cancer is refractory extensive-stage small cell lung carcinoma.

In embodiments, the combined effective amount is a combined synergistically effective amount.

In embodiments, the first agent is leflunomide. In embodiments, leflunomide is

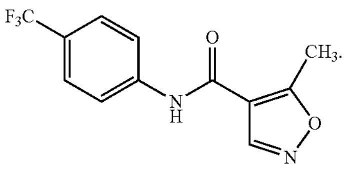 [SMILES: Cc1oncc1C(=O)Nc1ccc(C(F)(F)F)cc1]

In embodiments, leflunomide is

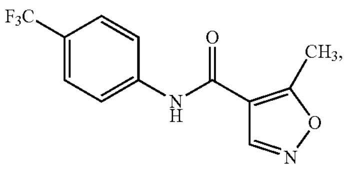 [SMILES: Cc1oncc1C(=O)Nc1ccc(C(F)(F)F)cc1]

or a salt thereof. In embodiments, leflunomide is

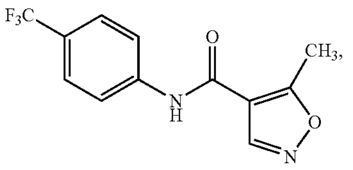 [SMILES: Cc1oncc1C(=O)Nc1ccc(C(F)(F)F)cc1]

or a pharmaceutically acceptable salt thereof. In embodiments, leflunomide is referred to herein as Leflu.

In embodiments, the first agent is teriflunomide. In embodiments, teriflunomide is

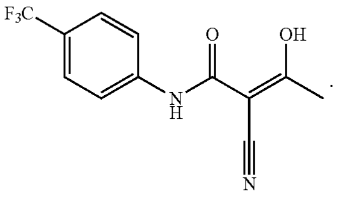 [SMILES: C/C(O)=C(\C#N)C(=O)Nc1ccc(C(F)(F)F)cc1]

In embodiments, teriflunomide is

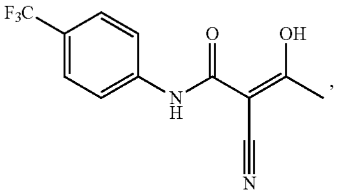 [SMILES: C/C(O)=C(\C#N)C(=O)Nc1ccc(C(F)(F)F)cc1]

or a salt thereof. In embodiments, teriflunomide is

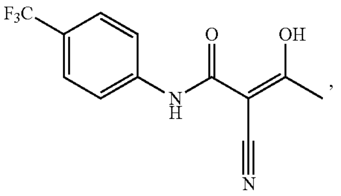

or a pharmaceutically acceptable salt thereof. In embodiments, teriflunomide is referred to herein as Teri.

In embodiments, the first agent is administered orally. In embodiments, the first agent is administered at a dose of from about 10 mg to about 100 mg. In embodiments, the first agent is administered at a dose of about 10 mg. In embodiments, the first agent is administered at a dose of about 20 mg. In embodiments, the first agent is administered at a dose of about 30 mg. In embodiments, the first agent is administered at a dose of about 40 mg. In embodiments, the first agent is administered at a dose of about 50 mg. In embodiments, the first agent is administered at a dose of about 60 mg. In embodiments, the first agent is administered at a dose of about 70 mg. In embodiments, the first agent is administered at a dose of about 80 mg. In embodiments, the first agent is administered at a dose of about 90 mg. In embodiments, the first agent is administered at a dose of about 100 mg.

In embodiments, the first agent is administered at a dose of from about 10 mg to about 200 mg once daily for 3 days prior to Day 1 of a 21-day cycle, termed the "loading dose". In embodiments, the 21-day cycle is repeated. In embodiments, the 21-day cycle is repeated four times. In embodiments, when the 21-day cycle is repeated, the patient is administered the loading dose prior to the first cycle only. In embodiments, the first agent is administered at a dose of from about 10 mg once daily for 3 days prior to Day 1. In embodiments, the first agent is administered at a dose of from about 20 mg once daily for 3 days prior to Day 1. In embodiments, the first agent is administered at a dose of from about 30 mg once daily for 3 days prior to Day 1. In embodiments, the first agent is administered at a dose of from about 40 mg once daily for 3 days prior to Day 1. In embodiments, the first agent is administered at a dose of from about 50 mg once daily for 3 days prior to Day 1. In embodiments, the first agent is administered at a dose of from about 60 mg once daily for 3 days prior to Day 1. In embodiments, the first agent is administered at a dose of from about 70 mg once daily for 3 days prior to Day 1. In embodiments, the first agent is administered at a dose of from about 80 mg once daily for 3 days prior to Day 1. In embodiments, the first agent is administered at a dose of from about 90 mg once daily for 3 days prior to Day 1. In embodiments, the first agent is administered at a dose of from about 100 mg once daily for 3 days prior to Day 1. In embodiments, the first agent is administered at a dose of from about 125 mg once daily for 3 days prior to Day 1. In embodiments, the first agent is administered at a dose of from about 150 mg once daily for 3 days prior to Day 1. In embodiments, the first agent is administered at a dose of from about 175 mg once daily for 3 days prior to Day 1. In embodiments, the first agent is administered at a dose of from about 200 mg once daily for 3 days prior to Day 1.

In embodiments, the first agent is administered at a dose of from about 10 mg to about 100 mg on Days 1 to 3. In embodiments, the first agent is administered at a dose of about 10 mg on Days 1 to 3. In embodiments, the first agent is administered at a dose of about 20 mg on Days 1 to 3. In embodiments, the first agent is administered at a dose of about 30 mg on Days 1 to 3. In embodiments, the first agent is administered at a dose of about 40 mg on Days 1 to 3. In embodiments, the first agent is administered at a dose of about 50 mg on Days 1 to 3. In embodiments, the first agent is administered at a dose of about 60 mg on Days 1 to 3. In embodiments, the first agent is administered at a dose of about 70 mg on Days 1 to 3. In embodiments, the first agent is administered at a dose of about 80 mg on Days 1 to 3. In embodiments, the first agent is administered at a dose of about 90 mg on Days 1 to 3. In embodiments, the first agent is administered at a dose of about 100 mg on Days 1 to 3. In embodiments, the cycle is repeated every 3 weeks. In embodiments, the cycle is repeated every 3 weeks for 4 cycles.

In embodiments, the second agent is lurbinectedin. In embodiments, lurbinectedin is

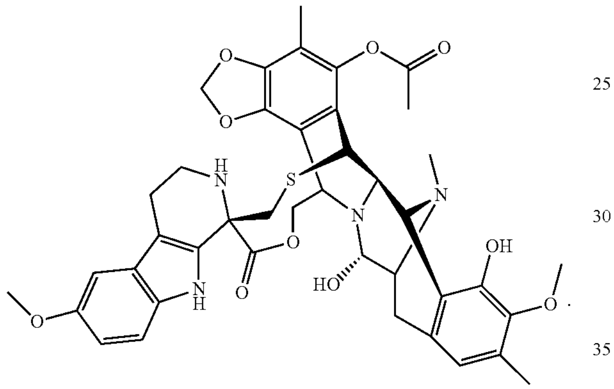

In embodiments, lurbinectedin is

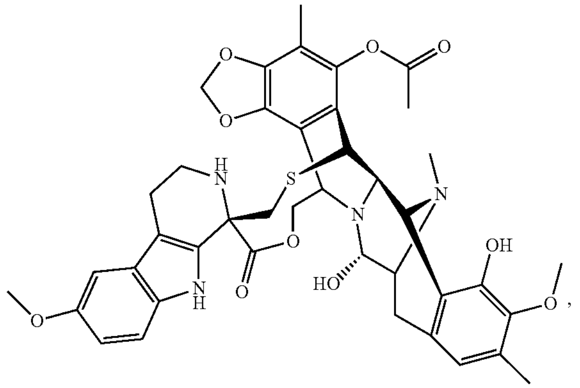

or a salt thereof. In embodiments, lurbinectedin is

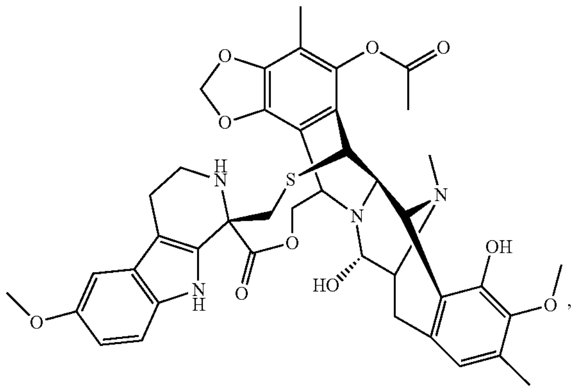

or a pharmaceutically acceptable salt thereof. In embodiments, lurbinectedin is referred to herein as Lur.

In embodiments, lurbinectedin is administered intravenously at a dose of from about 1 $mg/m^2$ to about 5 $mg/m^2$ IV. In embodiments, lurbinectedin is administered intravenously at a dose of about 1 $mg/m^2$ IV. In embodiments, lurbinectedin is administered intravenously at a dose of about 2 $mg/m^2$ IV. In embodiments, lurbinectedin is administered intravenously at a dose of about 2.6 $mg/m^2$ IV. In embodiments, lurbinectedin is administered intravenously at a dose of about 3 $mg/m^2$ IV. In embodiments, lurbinectedin is administered intravenously at a dose of about 3.2 $mg/m^2$ IV. In embodiments, lurbinectedin is administered intravenously at a dose of about 4 $mg/m^2$ IV. In embodiments, lurbinectedin is administered intravenously at a dose of about 5 $mg/m^2$ IV.

In embodiments, lurbinectedin is administered intravenously at a dose of from about 1 $mg/m^2$ to about 5 $mg/m^2$ over 60 minutes. In embodiments, lurbinectedin is administered intravenously at a dose of about 1 $mg/m^2$ over 60 minutes. In embodiments, lurbinectedin is administered intravenously at a dose of about 2 $mg/m^2$ over 60 minutes. In embodiments, lurbinectedin is administered intravenously at a dose of about 2.6 $mg/m^2$ over 60 minutes. In embodiments, lurbinectedin is administered intravenously at a dose of about 3 $mg/m^2$ over 60 minutes. In embodiments, lurbinectedin is administered intravenously at a dose of about 3.2 $mg/m^2$ over 60 minutes. In embodiments, lurbinectedin is administered intravenously at a dose of about 4 $mg/m^2$ over 60 minutes. In embodiments, lurbinectedin is administered intravenously at a dose of about 5 $mg/m^2$ over 60 minutes.

In embodiments, the second agent is carboplatin. In embodiments, the method further includes administering etoposide. In embodiments, the method further includes administering atezolizumab. In embodiments, the method further includes administering durvalumab.

In embodiments, carboplatin is

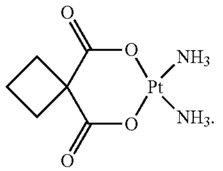

In embodiments, carboplatin is

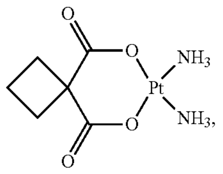

or a salt thereof. In embodiments, carboplatin is

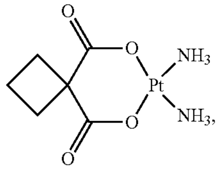

or a pharmaceutically acceptable salt thereof. In embodiments, carboplatin is referred to herein as Carbo.

In embodiments, etoposide is

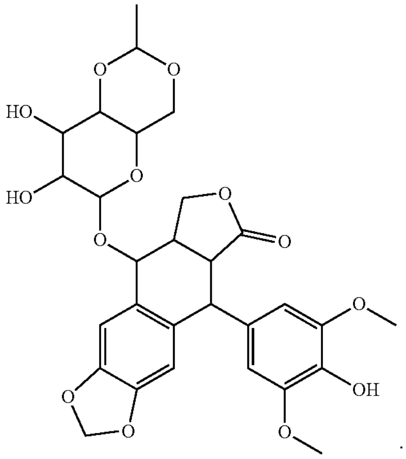 [SMILES: COc1cc(C2c3cc4c(cc3C(OC3OC5COC(C)OC5C(O)C3O)C3COC(=O)C23)OCO4)cc(OC)c1O]

.

In embodiments, etoposide is

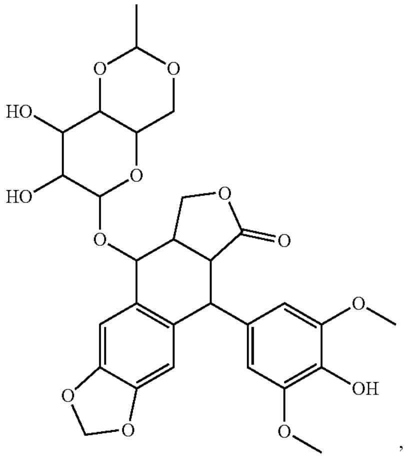 [SMILES: COc1cc(C2c3cc4c(cc3C(OC3OC5COC(C)OC5C(O)C3O)C3COC(=O)C23)OCO4)cc(OC)c1O]

, or a salt thereof. In embodiments, etoposide is

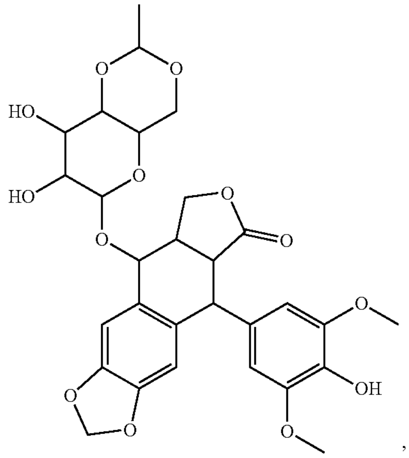 [SMILES: COc1cc(C2c3cc4c(cc3C(OC3OC5COC(C)OC5C(O)C3O)C3COC(=O)C23)OCO4)cc(OC)c1O]

, or a pharmaceutically acceptable salt thereof. In embodiments, etoposide is

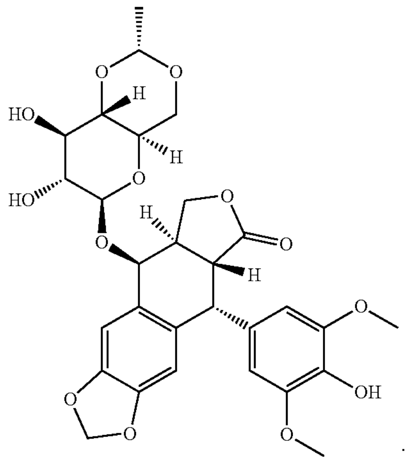

.

In embodiments, etoposide is

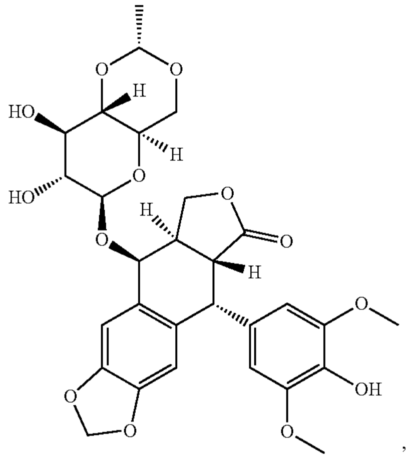

, or a salt thereof. In embodiments, etoposide is

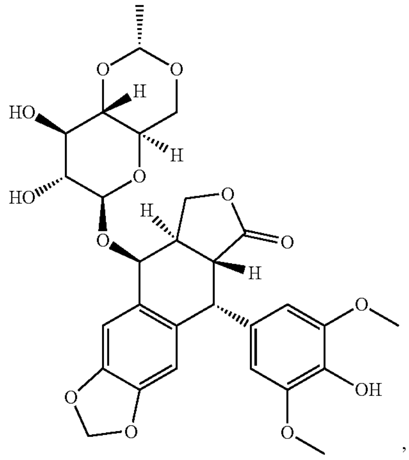

, or a pharmaceutically acceptable salt thereof.

In embodiments, atezolizumab is a monoclonal antibody having a heavy chain sequence:

(SEQ ID NO: 2)
EVQLVESGGGLVQPGGSLRLSCAASGFTFSDSWIHWVRQAPGKGLEWVAW
ISPYGGSTYYADSVKGRFTISADTSKNTAYLQMNSLRAEDTAVYYCARRH
WPGGFDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK.

In embodiments, atezolizumab is a monoclonal antibody having a light chain sequence:

(SEQ ID NO: 3)
DIQMTQSPSSLSASVGDRVTITCRASQDVSTAVAWYQQKPGKAPKLLIYS
ASFLYSGVPSRFSGSGSGTDFTLTISSLQPEDFATYYCQQYLYHPATFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC.

In embodiments, durvalumab is a monoclonal antibody having a heavy chain sequence:

(SEQ ID NO: 4)
EVQLVESGGGLVQPGGSLRLSCAASGFTFSRYWMSWVRQAPGKGLEWVAN
IKQDGSEKYYVDSVKGRFTISRDNAKNSLYLQMNSLRAEDTAVYYCAREG
GWFGELAFDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKRVEPKSCDKTHTCPPCPAPEFEGGPSVFLFPPK
PKDTLMISRTPEVTCVVVDVSHEDPEVKFNWYVDGVEVHNAKTKPREEQY

-continued
NSTYRVVSVLTVLHQDWLNGKEYKCKVSNKALPASIEKTISKAKGQPREP
QVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPG
K.

In embodiments, durvalumab is a monoclonal antibody having a light chain sequence:

(SEQ ID NO: 5)
EIVLTQSPGTLSLSPGERATLSCRASQRVSSSYLAWYQQKPGQAPRLLIY
DASSRATGIPDRFSGSGSGTDFTLTISRLEPEDFAVYYCQQYGSLPWTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC.

In embodiments, the second agent is cisplatin. In embodiments, the method further includes administering etoposide. In embodiments, the method further includes administering durvalumab.

In embodiments, cisplatin is

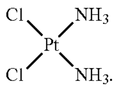

In embodiments, cisplatin is

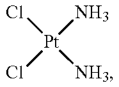

or a salt thereof. In embodiments, cisplatin is

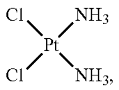

or a pharmaceutically acceptable salt thereof. In embodiments, cisplatin is

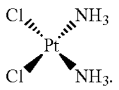

In embodiments, cisplatin is

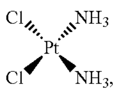

or a salt thereof. In embodiments, cisplatin is

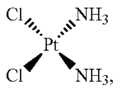

or a pharmaceutically acceptable salt thereof.

In embodiments, carboplatin is administered intravenously at a dose of from about 4 mg/mL·min to about 8 mg/mL·min. In embodiments, carboplatin is administered intravenously at a dose of about 4 mg/mL·min. In embodiments, carboplatin is administered intravenously at a dose of about 5 mg/mL·min. In embodiments, carboplatin is administered intravenously at a dose of about 6 mg/mL·min. In embodiments, carboplatin is administered intravenously at a dose of about 7 mg/mL·min. In embodiments, carboplatin is administered intravenously at a dose of about 8 mg/mL·min.

In embodiments, cisplatin is administered intravenously at a dose of from about 50 $mg/m^2$ IV to about 80 $mg/m^2$ IV. In embodiments, cisplatin is administered intravenously at a dose of from about 75 $mg/m^2$ IV to about 80 $mg/m^2$ IV. In embodiments, cisplatin is administered intravenously at a dose of about 50 $mg/m^2$ IV. In embodiments, cisplatin is administered intravenously at a dose of about 55 $mg/m^2$ IV. In embodiments, cisplatin is administered intravenously at a dose of about 60 $mg/m^2$ IV. In embodiments, cisplatin is administered intravenously at a dose of about 65 $mg/m^2$ IV. In embodiments, cisplatin is administered intravenously at a dose of about 70 $mg/m^2$ IV. In embodiments, cisplatin is administered intravenously at a dose of about 75 $mg/m^2$ IV. In embodiments, cisplatin is administered intravenously at a dose of about 80 $mg/m^2$ IV.

In embodiments, etoposide is administered intravenously at a dose of from about 50 $mg/m^2$ to about 100 $mg/m^2$. In embodiments, etoposide is administered intravenously at a dose of from about 80 $mg/m^2$ to about 100 $mg/m^2$. In embodiments, etoposide is administered intravenously at a dose of about 50 $mg/m^2$. In embodiments, etoposide is administered intravenously at a dose of about 55 $mg/m^2$. In embodiments, etoposide is administered intravenously at a dose of about 60 $mg/m^2$. In embodiments, etoposide is administered intravenously at a dose of about 65 $mg/m^2$. In embodiments, etoposide is administered intravenously at a dose of about 70 $mg/m^2$. In embodiments, etoposide is administered intravenously at a dose of about 75 $mg/m^2$. In embodiments, etoposide is administered intravenously at a dose of about 80 $mg/m^2$. In embodiments, etoposide is administered intravenously at a dose of about 85 $mg/m^2$. In embodiments, etoposide is administered intravenously at a dose of about 90 $mg/m^2$. In embodiments, etoposide is administered intravenously at a dose of about 95 $mg/m^2$. In embodiments, etoposide is administered intravenously at a dose of about 100 $mg/m^2$. In embodiments, etoposide is administered intravenously at a dose of about 50 $mg/m^2$ over 60 minutes. In embodiments, etoposide is administered intravenously at a dose of about 55 $mg/m^2$ over 60 minutes. In embodiments, etoposide is administered intravenously at a dose of about 60 $mg/m^2$ over 60 minutes. In embodiments, etoposide is administered intravenously at a dose of about 65 $mg/m^2$ over 60 minutes. In embodiments, etoposide is administered intravenously at a dose of about 70 $mg/m^2$ over 60 minutes. In embodiments, etoposide is administered intravenously at a dose of about 75 $mg/m^2$ over 60 minutes. In embodiments, etoposide is administered intravenously at a dose of about 80 $mg/m^2$ over 60 minutes. In embodiments, etoposide is administered intravenously at a dose of about 85 $mg/m^2$ over 60 minutes. In embodiments, etoposide is administered intravenously at a dose of about 90 $mg/m^2$ over 60 minutes. In embodiments, etoposide is administered intravenously at a dose of about 95 $mg/m^2$ over 60 minutes. In embodiments, etoposide is administered intravenously at a dose of about 100 $mg/m^2$ over 60 minutes.

In embodiments, atezolizumab is administered intravenously at a dose of from about 500 mg IV to about 1,800 mg IV. In embodiments, atezolizumab is administered intravenously at a dose of about 500 mg IV. In embodiments, atezolizumab is administered intravenously at a dose of about 600 mg IV. In embodiments, atezolizumab is administered intravenously at a dose of about 700 mg IV. In embodiments, atezolizumab is administered intravenously at a dose of about 800 mg IV. In embodiments, atezolizumab is administered intravenously at a dose of about 840 mg IV. In embodiments, atezolizumab is administered intravenously at a dose of about 900 mg IV. In embodiments, atezolizumab is administered intravenously at a dose of about 1,000 mg IV. In embodiments, atezolizumab is administered intravenously at a dose of about 1,100 mg IV. In embodiments, atezolizumab is administered intravenously at a dose of about 1,200 mg IV. In embodiments, atezolizumab is administered intravenously at a dose of about 1,300 mg IV. In embodiments, atezolizumab is administered intravenously at a dose of about 1,400 mg IV. In embodiments, atezolizumab is administered intravenously at a dose of about 1,500 mg IV. In embodiments, atezolizumab is administered intravenously at a dose of about 1,600 mg IV. In embodiments, atezolizumab is administered intravenously at a dose of about 1,680 mg IV. In embodiments, atezolizumab is administered intravenously at a dose of about 1,700 mg IV. In embodiments, atezolizumab is administered intravenously at a dose of about 1,800 mg IV.

In embodiments, durvalumab is administered intravenously at a dose of from about 1,000 mg IV to about 1,500 mg IV. In embodiments, durvalumab is administered intravenously at a dose of about 1,000 mg IV. In embodiments, durvalumab is administered intravenously at a dose of about 1,100 mg IV. In embodiments, durvalumab is administered intravenously at a dose of about 1,200 mg IV. In embodiments, durvalumab is administered intravenously at a dose of about 1,300 mg IV. In embodiments, durvalumab is administered intravenously at a dose of about 1,400 mg IV. In embodiments, durvalumab is administered intravenously at a dose of about 1,500 mg IV.

In embodiments, the method includes administering a combined effective amount of the first agent (e.g., leflunomide or teriflunomide), carboplatin, etoposide, and atezolizumab. In embodiments, the first agent (e.g., leflunomide or teriflunomide), carboplatin, etoposide, and atezolizumab are administered at a dose as described herein. In embodiments, carboplatin is administered intravenously at a dose of about AUC 5 IV over 30 minutes on Day 1. In embodiments, etoposide is administered intravenously at a dose of about 100 $mg/m^2$ over 60 minutes on Days 1 to 3. In embodiments, atezolizumab is administered intravenously at a dose of about 1,200 mg IV on Day 1. In embodiments, the cycle is repeated every 3 weeks. In embodiments, the cycle is repeated every 3 weeks for 4 cycles.

In embodiments, the method includes administering a combined effective amount of the first agent (e.g., leflunomide or teriflunomide), carboplatin, etoposide, and durvalumab. In embodiments, the first agent (e.g., leflunomide or teriflunomide), carboplatin, etoposide, and durvalumab are administered at a dose as described herein. In embodiments, carboplatin is administered intravenously at a dose of about AUC 5 or 6 IV on Day 1. In embodiments, etoposide is administered intravenously at a dose of from about 80 $mg/m^2$ IV to about 100 $mg/m^2$ IV on Days 1 to 3. In embodiments, durvalumab is administered intravenously at a dose of about 1,500 mg IV on Day 1. In embodiments, the cycle is repeated every 3 weeks. In embodiments, the cycle is repeated every 3 weeks for 4 cycles.

In embodiments, the method includes administering a combined effective amount of the first agent (e.g., leflunomide or teriflunomide), cisplatin, etoposide, and durvalumab. In embodiments, the first agent (e.g., leflunomide or teriflunomide), cisplatin, etoposide, and durvalumab are administered at a dose as described herein. In embodiments, cisplatin is administered intravenously at a dose of about 75 $mg/m^2$ IV to about 80 $mg/m^2$ IV on Day 1. In embodiments, etoposide is administered intravenously at a dose of from about 80 $mg/m^2$ IV to about 100 $mg/m^2$ IV on Days 1 to 3. In embodiments, durvalumab is administered intravenously at a dose of about 1,500 mg IV on Day 1. In embodiments, the cycle is repeated every 3 weeks. In embodiments, the cycle is repeated every 3 weeks for 4 cycles.

III. Kits

In an aspect is provided a kit including a combined effective amount of a first agent and a second agent, wherein the first agent is leflunomide or teriflunomide and the second agent is lurbinectedin, carboplatin, or cisplatin.

In an aspect is provided a kit including a combined effective amount of a first agent and a second agent, wherein the first agent is leflunomide or teriflunomide and the second agent is lurbinectedin or carboplatin.

In embodiments, the combined effective amount is a combined synergistically effective amount.

In embodiments, the first agent is leflunomide. In embodiments, leflunomide is in an oral dosage form. In embodiments, the first agent is teriflunomide. In embodiments, teriflunomide is in an oral dosage form.

In embodiments, the second agent is lurbinectedin. In embodiments, lurbinectedin is in an intravenous dosage form.

In embodiments, the second agent is carboplatin. In embodiments, carboplatin is in an intravenous dosage form. In embodiments, the kit further includes etoposide. In embodiments, etoposide is in an intravenous dosage form. In embodiments, the kit further includes atezolizumab. In embodiments, atezolizumab is in an intravenous dosage form. In embodiments, the kit further includes durvalumab. In embodiments, durvalumab is in an intravenous dosage form.

In embodiments, the second agent is cisplatin. In embodiments, cisplatin is in an intravenous dosage form. In embodiments, the kit further includes etoposide. In embodiments, etoposide is in an intravenous dosage form. In embodiments, the kit further includes durvalumab. In embodiments, durvalumab is in an intravenous dosage form.

In embodiments, each agent is in a separate dosage form. In embodiments, two or more agents are combined into a single dosage form. In embodiments, the agents that are in an intravenous dosage form are combined into a single intravenous dosage form.

In embodiments, the kit further includes a pharmaceutically acceptable excipient.

IV. Embodiments

Embodiment P1. A method of treating small cell lung cancer in a subject in need thereof, said method comprising administering to the subject a combined effective amount of a first agent and a second agent, wherein the first agent is leflunomide or teriflunomide and the second agent is lurbinectedin or carboplatin.

Embodiment P2. The method of embodiment P1, wherein the first agent is leflunomide.

Embodiment P3. The method of embodiment P1, wherein the first agent is teriflunomide.

Embodiment P4. The method of one of embodiments P1 to P3, wherein the second agent is lurbinectedin.

Embodiment P5. The method of embodiment P4, wherein lurbinectedin is administered intravenously at a dose of from about 1 $mg/m^2$ to about 5 $mg/m^2$ over 60 minutes.

Embodiment P6. The method of embodiment P4, wherein lurbinectedin is administered intravenously at a dose of about 3.2 $mg/m^2$ over 60 minutes.

Embodiment P7. The method of one of embodiments P1 to P3, wherein the second agent is carboplatin.

Embodiment P8. The method of embodiment P7, wherein carboplatin is administered intravenously at a dose of from about 4 mg/mL·min to about 8 mg/mL·min.

Embodiment P9. The method of embodiment P7, wherein carboplatin is administered intravenously at a dose of about 5 mg/mL·min.

Embodiment P10. The method of one of embodiments P7 to P9, further comprising administering etoposide.

Embodiment P11. The method of embodiment P10, wherein etoposide is administered intravenously at a dose of from about 80 $mg/m^2$ to about 100 $mg/m^2$.

Embodiment P12. The method of embodiment P10, wherein etoposide is administered intravenously at a dose of about 100 $mg/m^2$ over 60 minutes.

Embodiment P13. The method of one of embodiments P10 to P12, further comprising administering atezolizumab.

Embodiment P14. The method of embodiment P13, wherein atezolizumab is administered intravenously at a dose of about 1,200 mg IV.

Embodiment P15. The method of one of embodiments P10 to P12, further comprising administering durvalumab.

Embodiment P16. The method of embodiment P15, wherein durvalumab is administered intravenously at a dose of about 1,500 mg IV.

Embodiment P17. The method of one of embodiments P1 to P16, wherein the combined effective amount is a combined synergistically effective amount.

Embodiment P18. The method of one of embodiments P1 to P17, wherein the first agent is administered orally.

Embodiment P19. The method of one of embodiments P1 to P18, wherein the first agent is administered at a dose of from about 10 mg to about 100 mg.

Embodiment P20. The method of one of embodiments P1 to P18, wherein the first agent is administered at a dose of about 10 mg.

Embodiment P21. The method of one of embodiments P1 to P18, wherein the first agent is administered at a dose of about 20 mg.

Embodiment P22. The method of one of embodiments P1 to P18, wherein the first agent is administered at a dose of about 30 mg.

Embodiment P23. The method of one of embodiments P1 to P18, wherein the first agent is administered at a dose of about 40 mg.

Embodiment P24. The method of one of embodiments P1 to P18, wherein the first agent is administered at a dose of about 50 mg.

Embodiment P25. The method of one of embodiments P1 to P18, wherein the first agent is administered at a dose of about 60 mg.

Embodiment P26. The method of one of embodiments P1 to P18, wherein the first agent is administered at a dose of about 100 mg.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1

Small cell lung cancer (SCLC) is an aggressive malignancy that leads to fatalities if left untreated (1). Most patients are diagnosed with metastatic disease and rapid tumor growth. Unfortunately, the clinical outcome of SCLC patients is poor due to early relapse and standard chemotherapy treatment options for recurrent tumors are limited and ineffective (2). First-line treatment has response rates up to 80%, but many patients relapse within 6 months, and the 5-year survival rate remains at 6% (1,3,4).

Several studies in the past have associated mitochondrial fragmentation with tumor progression in multiple cancers such as mesothelioma, ovarian, breast, lung, and pancreatic cancer (5,6). Both mitochondrial fragmentation (fission) and elongation (fusion) are responsible for maintaining proper morphology. However, the rapid proliferation of cancer cells resulting from their constant growth and metabolic shifts triggers mitochondrial fragmentation (7). Dynamin-related protein 1 (DRP1) plays a central role in mitochondrial fission and fusion regulation. Notably, its phosphorylation at site $Ser^{616}$ (fission) leads to activation, while at $Ser^{637}$ (fusion) leads to inactivation (8). There is growing evidence that mitochondrial fission and fusion can be a target of tumor therapy. Toward this, studies have reported the effect of DHODH (dihydroorotate dehydrogenase) inhibitors leflunomide (Leflu) and teriflunomide (Teri) on mitochondrial fusion/fission dynamics in cancer (9-11). DHODH is a crucial enzyme in the de novo pyrimidine biosynthesis, which is necessary for proliferation of cells. Leflu was shown to block access to the binding site of the DHODH. Therefore, we hypothesized that combining Leflu and Teri with chemotherapeutic agents may be a potent therapeutic strategy for the clinical treatment of SCLC.

SCLC patients typically receive chemotherapy combinations like carboplatin/etoposide or irinotecan but thus far, have had poor prognoses (12). Lurbinectedin (Lur) is a promising new agent to treat SCLC or mesothelioma patients after first-line systemic therapy failure because it has a direct cytotoxic effect on tumor cells by blocking the binding of oncogenic transcription factors to their target sequences and promotes the irreversible proteasomal degradation of RNA polymerase II (13). Additionally, another study demonstrated the sensitivity of SCLC cell lines to seven transcriptional inhibitors leading to treatment strategies focused on RNA transcription inhibition and promoting the degradation of elongating RNA (14).

In the present study, we have demonstrated the effect of Teri and Leflu on DRP1 and the synergism of these two compounds with Carbo and Lur in vitro and in vivo models of SCLC. We investigated (i) the theoretical binding between Leflu/Teri and DRP1; (ii) DRP1 phosphorylation as a function of Teri treatment; (iii) the morphology of mitochondrial networks; (iv) the effect of Teri/Carbo on cell proliferation in vitro and in vivo; (v) the effect of Teri/Carbo on cellular purines and pyrimidines; (vi) the effect of DRP1 CRISPR knockout on the expression of genes associated with mitochondria and pyrimidines; and (vii) the effects of Teri/Lur in vitro and in vivo. Together, the results from our comprehensive study revealed that pharmacological inhibition of DRP1 and DHODH with combinations of Teri, Lur, Carbo, and Leflu accelerated cell death by reducing DRP1 activity, pyrimidine synthesis, and impeded mitochondrial fragmentation.

Cell Culture and Materials

SCLC cells were purchased from ATCC (Manassas, VA) and maintained in RPMI1640 (Thermo Fisher Scientific Waltham, MA) supplemented with 10% (v/v) fetal bovine serum as previously described (15). Cells were routinely screened for mycoplasma. All biological reagents were purchased from Sigma-Aldrich (St. Louise, MO) or Thermo Fisher Scientific (Waltham, MA) unless specified. Teriflunomide and leflunomide were procured from Tocris (Minneapolis, MN), carboplatin from Teva Pharmaceuticals (Irvine, CA), and lurbinectedin from MedChemExpress LLC (Monmouth Junction, NJ).

Immunoblotting

SCLC total cell lysates were prepared using RIPA (radioimmunoprecipitation assay lysis buffer) lysis buffer. Protein concentration was determined using DC Protein Assay Kit Bio-Rad (Hercules, CA). Samples were then run on SDS-PAGE in 4-15% polyacrylamide gels and transferred onto Immobilon membranes (Millipore, MO), blocked, incubated with specific primary antibodies at 4° C. overnight, and subsequently developed with secondary antibodies. The following primary antibody were used: pan-Actin, Phospho-DRP1 ($Ser^{616}$), Phospho-DRP1 ($Ser^{637}$), Histone H2B ($V^{119}$), Phospho-Histone H2A.X ($Ser^{139}$), Phospho-P53 ($Ser^{15}$), P-53, Cleaved PARP ($Asp^{214}$) (D64E10), Phospho-Chk1 ($Ser^{345}$) (133D3) and p21 were from Cell Signaling Technology (City of Industry, CA), β-Actin (Sigma-Aldrich, St. Luis, MO), Phospho RNA Polymerase II (S2) antibody (Bethyl Lab, Montgomery, TX), RNA Polymerase II CTD4H8 (BioLegend, San Diego, CA), DHODH (E-8), DRP1 (C-5), GAPDH (0411), c-Myc (9E10), Tom20 (F-10), FisI (B-5), OPA1 (D-9), antibodies from Santa Cruz Biotechnology (Dallas, TX) and MFN2 (Abcam, Boston, MA) and Chk1, MDM2, Cyclin CDK4 and D1, and E2F1 (Proteintech, Rosemont, IL).

CCK-8 Assay

We have determined cell cytotoxicity toward a specific drug, employing Cell Counting Kit-8 (Dojindo Molecular Technologies, Rockville, MD) as previously described (15).

pDRP1 Immunofluorescence Staining and Analysis

SBC3 and SBC5 cells were grown on glass coverslips and treated with Teri overnight. Next, cells were fixed in 4% paraformaldehyde, permeabilized, and blocked before incubating with pDRP1 ($Ser^{616}$) antibody followed by Alexa 488 secondary antibody. This was followed by staining with Tom20 (F-10) antibody. A far-red dye was used for cytoplasmic staining. Fluorescent images were acquired on an Axio Observer 7 inverted microscope (Carl Zeiss, Jena, Germany). Nuclei and DRP1 were stained with DAPI and Alexa 488 secondary antibody. All imaging was performed using a 40×/0.95 NA Plan-Apochromat objective with a final per pixel scaling of 0.147 by 0.147 microns. Within each 3×3 field of image view (>200 cells per image), QuPath 0.2.0M9 was used to detect cell nuclei, a cytoplasmic area around the nucleus was expanded for analysis, followed by limiting the area of that blind expansion based on the presence of the cytoplasmic dye. The presence of overly bright and uniform DAPI signal along with the absence of cytoplasmic dye were used to select and remove dead cells and debris from the analysis. The subcellular detection command limited the analysis area within each "cell object" to the actual cell area by a far-red signal intensity threshold. The mean pDRP1 signal intensity was then measured within that area. The green intensity sum of these areas was calculated per cell and then averaged for each sample image.

CRISPR-Cas9 Cell Line Generation

Figure 8:
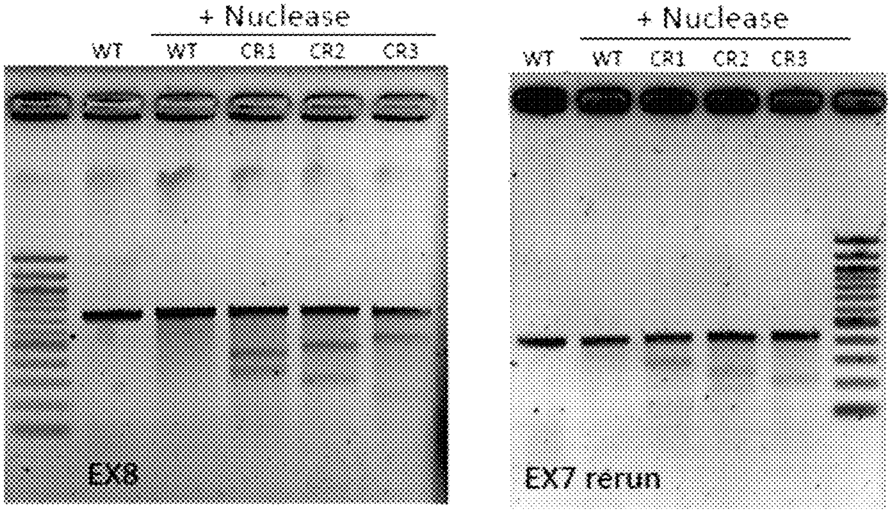
FIG. 8. CRISPR SgRNA efficiency testing. The surveyors assay result. The selected sgRNAs tested the efficiency at 48 hours after transfected in 293T cells.
Figure 9:
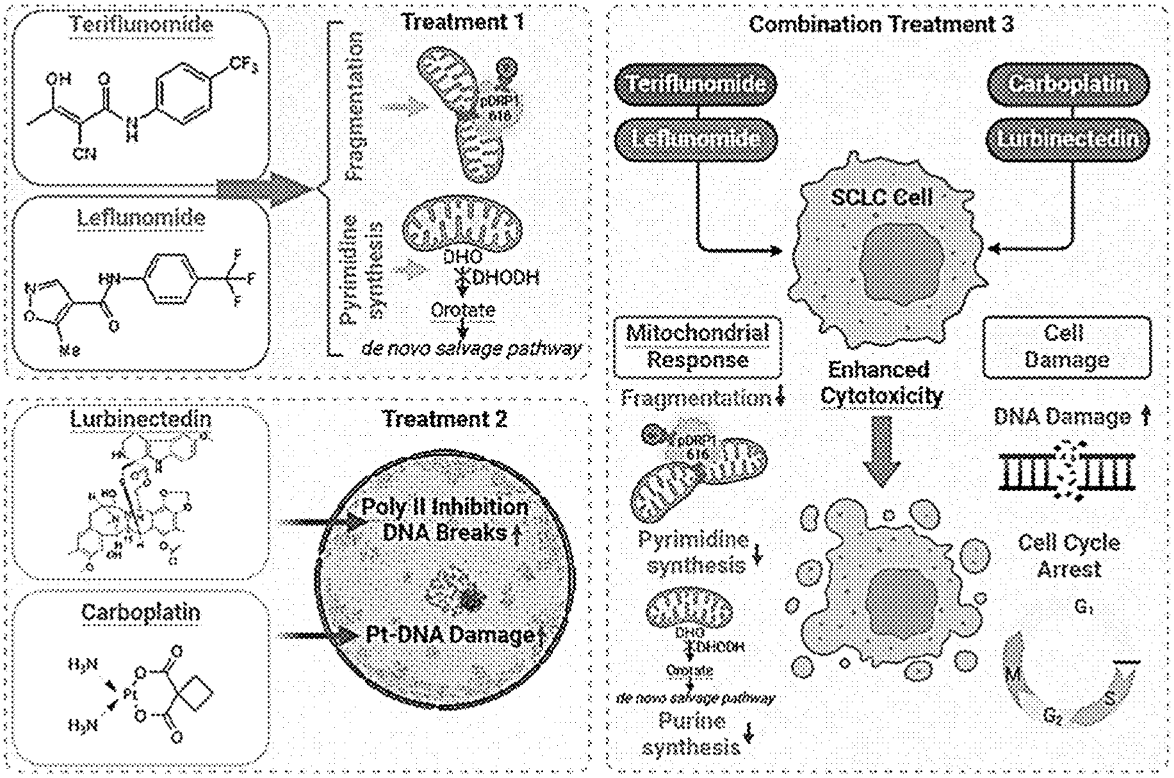
FIG. 9. Graphical representation of the inhibition effect of teriflunomide/leflunomide on SCLC cell viability. Carboplatin and lurbinectedin common cytotoxic agents robustly induced cell DNA damage and apoptosis. Teriflunomide/leflunomide affected cell proliferation through inhibition of DRP1 phosphorylation at Ser 616 and alterations in purine/pyrimidine pathway. Shift in the balance of fission proteins conducted the remodeling of mitochondrial network, mitochondria became less fragmentated and more elongated. Combination of teriflunomide with carboplatin or lurbinectedin is more effective in reducing cancer cells proliferation and promotes cell destruction and death.
Figure 10:
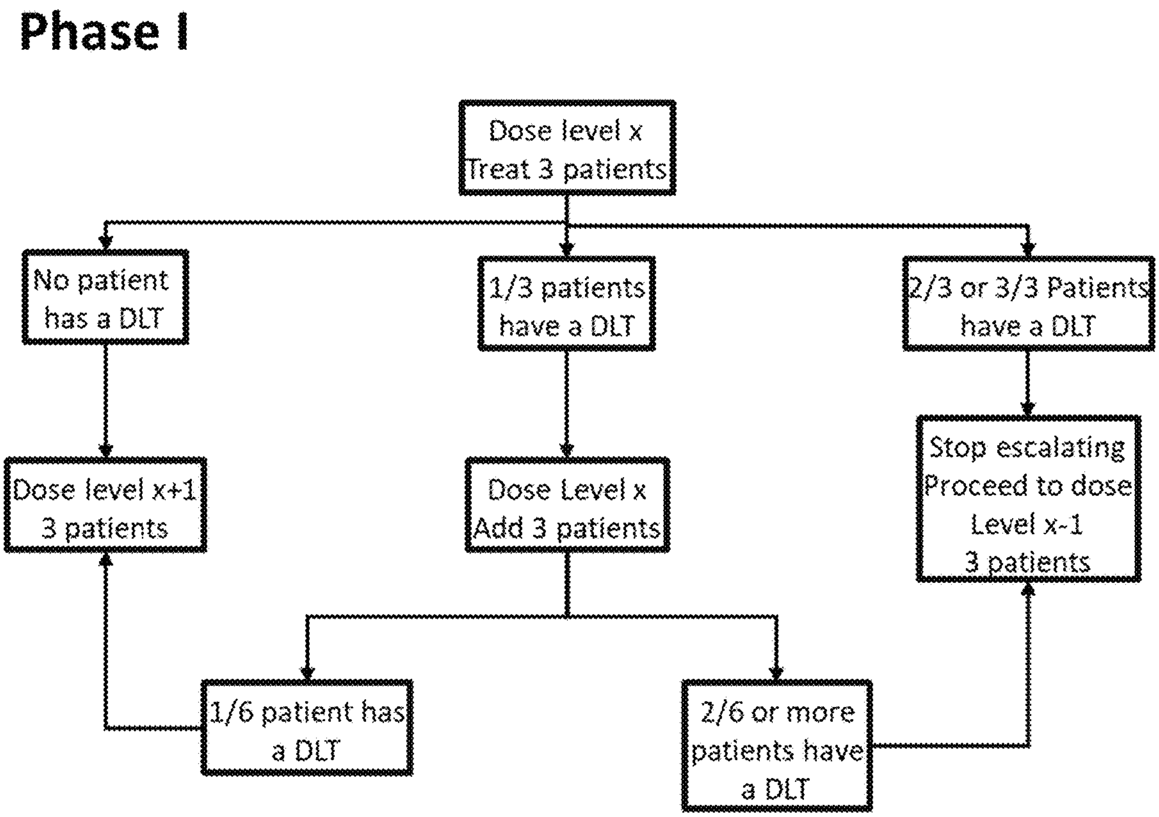
FIG. 10. Phase I/II dose-escalation trials of leflunomide alone or in combination in extensive-stage small cell lung carcinoma.
Figure 11:
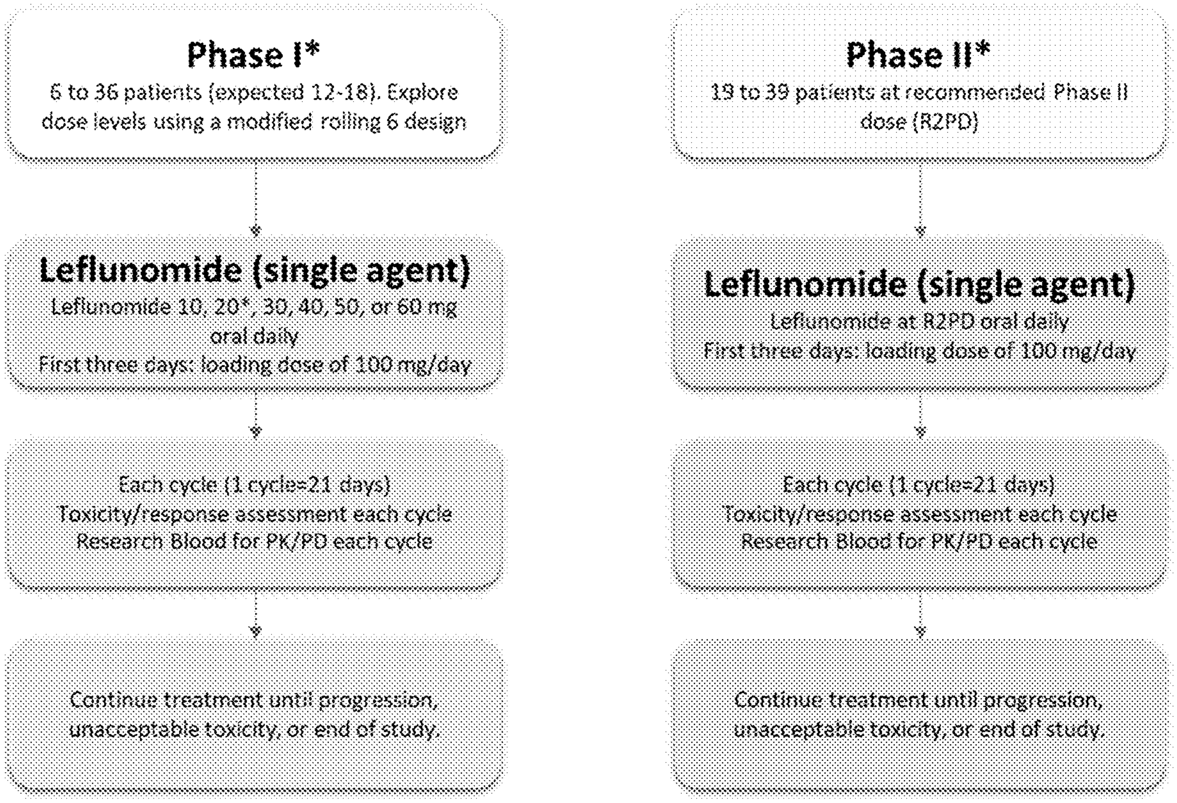
FIG. 11. Phase I/II dose-escalation trials of leflunomide alone in relapsed sensitive/refractory extensive-stage small cell lung carcinoma. *Clinical Pharmacology will be performed to characterize the relationship between serum concentration of the active leflunomide metabolite, teriflunomide (A77 1726), and toxicity, and to assess the relationship between serum concentration of the active leflunomide metabolite, teriflunomide (A77 1726), and disease response.
Figure 12:
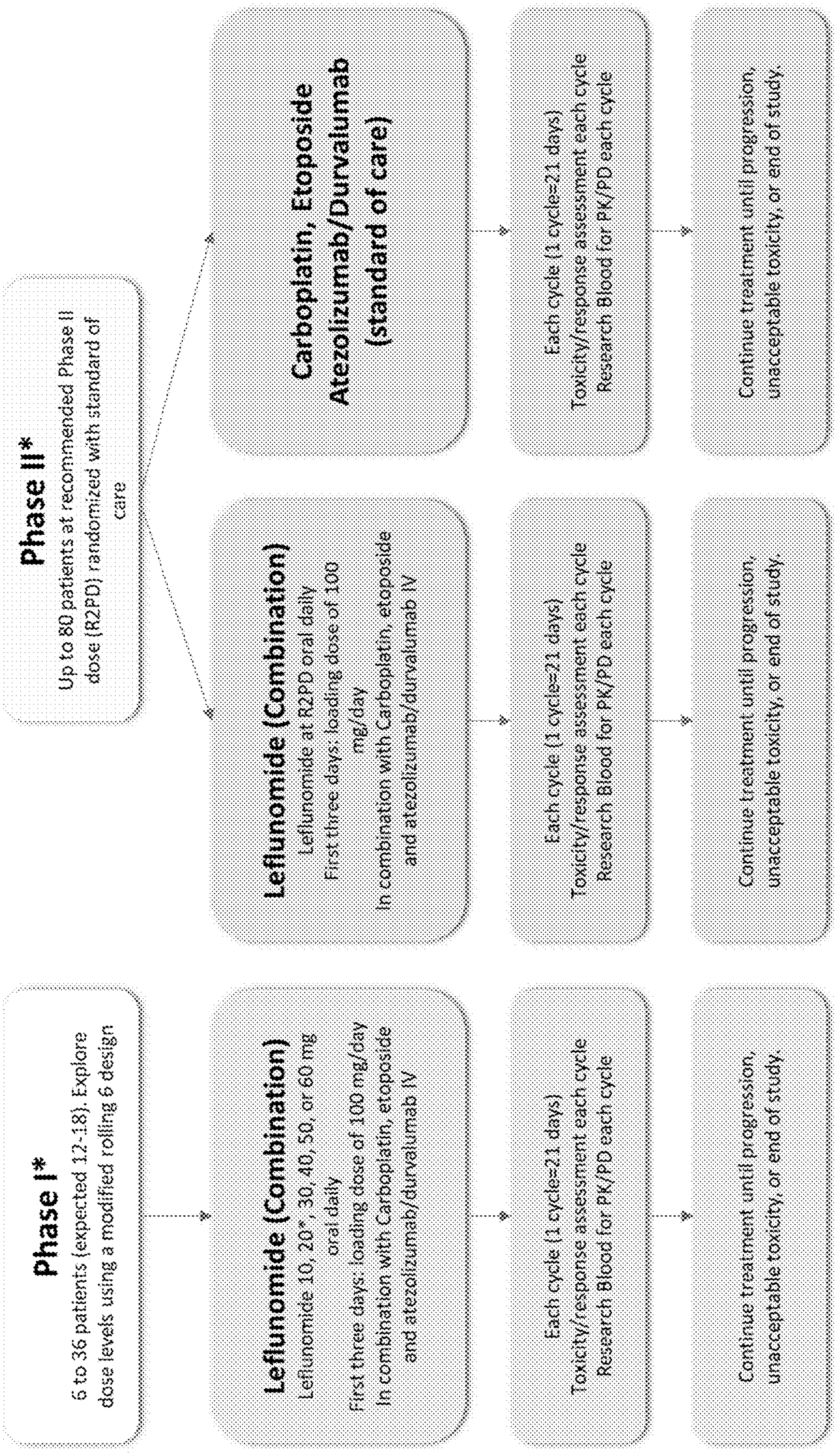
FIG. 12. Phase I/II dose-escalation trials of leflunomide in combination with carboplatin, etoposide, and atezolizumab or durvalumab in first-line extensive-stage small cell lung carcinoma. *Clinical Pharmacology will be performed to characterize the relationship between serum concentration of the active leflunomide metabolite, teriflunomide (A77 1726), and toxicity, and to assess the relationship between serum concentration of the active leflunomide metabolite, teriflunomide (A77 1726), and disease response.
Figure 13:
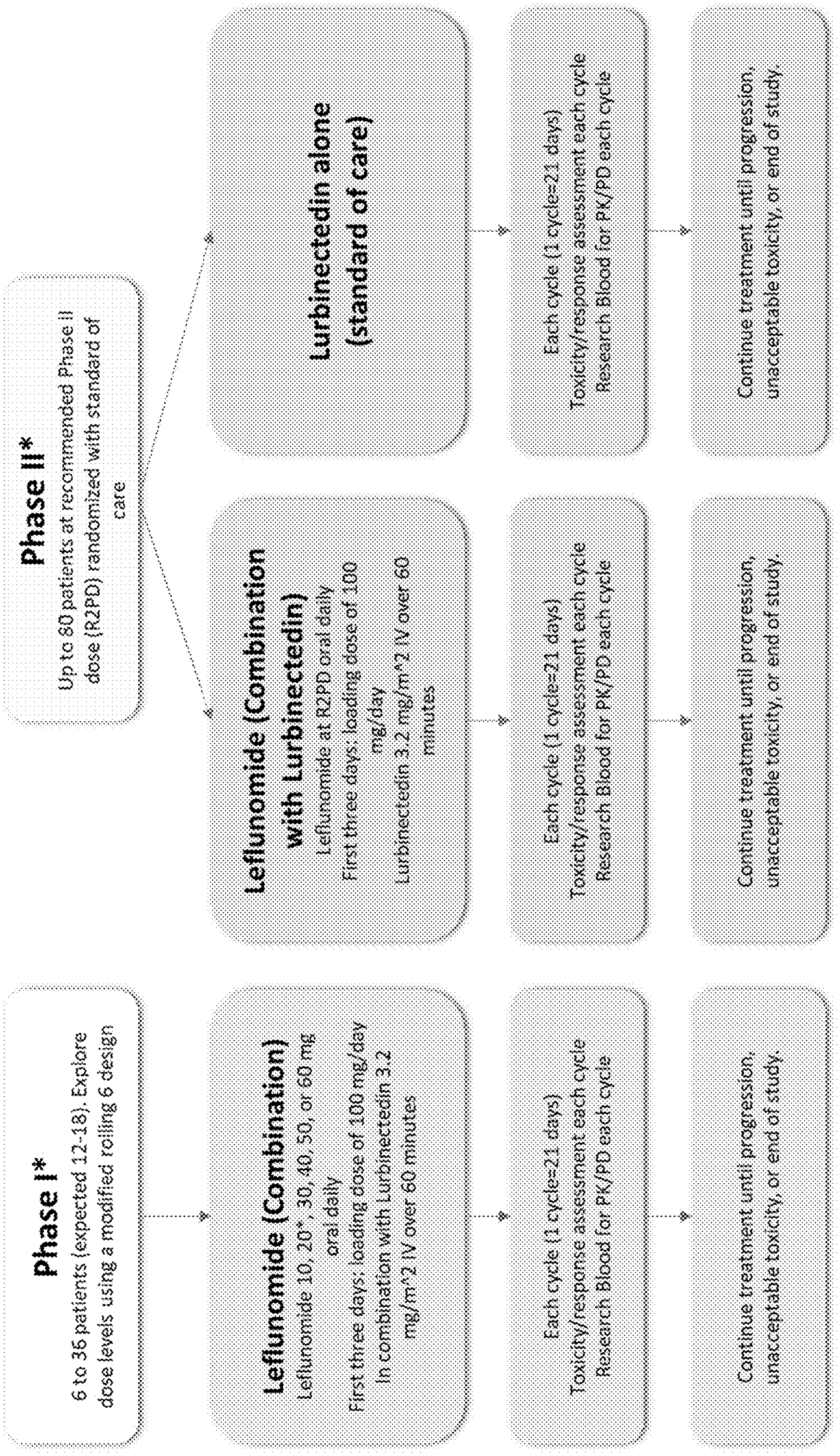
FIG. 13. Phase I/II dose-escalation trials of leflunomide in combination with lurbinectedin in second-line extensive-stage small cell lung carcinoma (80 patients). *Clinical Pharmacology will be performed to characterize the relationship between serum concentration of the active leflunomide metabolite, teriflunomide (A77 1726), and toxicity, and to assess the relationship between serum concentration of the active leflunomide metabolite, teriflunomide (A77 1726), and disease response.

DRP1 KO sgRNA was designed using the GPP sgRNA Designer which selects specific guide RNAs close to the target sequence minimizing identical genomic matches or near-matches to reduce the risk of off-target effects. After confirming the CRISPR editing efficiency by the surveyor nuclease assay, two sgRNAs, hDRP1-EX7-CR1 CAAGTTTAGTGATTACAGCT (SEQ ID NO:6) and hDRP1-EX8-CR1 TCTTGTTGTTAATATCTAGC (SEQ ID NO:7), were selected for the project. Table 1 represents the primer design surveyor nuclease assay. We designed and tested CRISPR sgRNA efficiency and selected hDRP1-EX7-CR1: CAAGTTTAGTGATTACAGCT (SEQ ID NO:6) and hDRP1-EX8-CR1: TCTTGTTGTTAATATCTAGC (SEQ ID NO:7) to use for the KO project (FIG. 8). In the KO experiment, the SBC3 and SBC5 lines were infected with pCW-Cas9-Puro (Addgene #50661), a Tet-mediated Cas9 lentiviral vector with puromycin selectable marker, followed by the 1 ug/mL puromycin selection, and then infected with LV-Blast-DRP1-dCREX7-EX8-CRs, expressing two selected sgRNAs targeting DRP1 Exon 7 and Exon 8, followed by Blasticidin screening. After drug screening, the cell pool was analyzed by NGS to evaluate the KO efficiency. CRISPR experiments were performed by The Gene Editing and Viral Vector Core City of Hope.

doxorubicin were hybridized with Reporter CodeSet and Capture ProbeSet at 65° C. for 18 h. Next, the Prep Station (nCounter MAX/FLEX) transferred all reagents, separated the magnetic beads, and immobilized molecular complexes on the sample cartridge. Subsequently, the cartridge was scanned using nCounter Digital Analyzer, and finally, the data was analyzed using nSolver Analysis Software 4.0. Each experiment was conducted in triplicate. Genes with lower normalized gene expression count under background threshold were excluded from the differential expression analysis. The expression patterns were presented in dot plots using R ggplot2 package. The dot size represents the significant p-value, and the color represents the different expression levels (log 2 Fold Change). Assay and analysis were done by the Research Molecular Pathology facility (City of Hope, Duarte, CA).

In Silico Analysis

Gene expression data set (GSE1037) (16) was downloaded from the National Center for Biotechnology Information Gene Expression Omnibus1 (GEO) (17). It included 19 normal samples, SBC3 and SBC5 cells. The annotation files were downloaded from GEMMA (18). The differential expression gene analysis was performed using GEO2R with R LIMMA package, FDR<0.05, and was presented in dot plots using R ggplot2 package (19). Most genes have multiple clones on this array platform. Each row represents a clone labeled with a gene symbol and probe ID.

LC-MS Method for Detection and Measurements of Nucleotides, Nucleosides and Nucleobases in the Cell Pellets and Tissues These studies were performed by Creative Proteomics in their facility in Shirley, NY. Each sample was placed into 250 μL of 80% methanol. Tissue samples were weighed in 2-mL Eppendorf tubes, and 80% methanol was added at 10 μL per mg of raw tissue. The tissue and cell samples were then homogenized on a MM 400 mill mixer with the aid of two 4-mm metal beads at a shaking frequency of 30 Hz for

TABLE 1

| Target Exon | Cell line | Forward primer | Reverse primer | PCR size | Cut size | |
|---|---|---|---|---|---|---|
| DRP1-EX7-CR1 | 293T | agtgggattgtagatgagggtt (SEQ ID NO: 8) | tctccctttagggcaacgga (SEQ ID NO: 9) | 405 | 284 | 121 |
| DRP1-EX7-CR2 | 293T | | | 405 | 223 | 182 |
| DRP1-EX7-CR3 | 293T | | | 405 | 237 | 168 |
| DRP1-EX8-CR1 | 293T | | | 709 | 403 | 306 |
| DRP1-EX8-CR2 | 293T | | | 709 | 445 | 264 |
| DRP1-EX8-CR3 | 293T | | | 709 | 509 | 200 |
| EEF1A-CR1 (Ctrl) | 293T | CTGAGCGTGA ACGTGGTATCA (SEQ ID NO: 10) | GGCAGACAGTAC TCTATCAACTCA (SEQ ID NO: 11) | 787 | 184 | 603 |

NanoString Differential Expression Analysis

Gene expression was determined with a custom panel (20 genes) employing a NanoString nCounter platform (NanoString Technologies, Inc., Seattle, WA). All experimental procedures were performed using the manufactured protocol with minor modifications. Briefly, 100 ng of RNA extracted from SBC-3 and SBC-5 cells in the presence or absence of 2 min and the homogenization step was repeated twice. The samples were placed at −20° C. for 1 h and then centrifuged at 21,000×g for 10 min. The clear supernatants were collected for LC-MS quantitation. Protein content was measured from protein pellets by Bradford protein assays and used to normalize metabolite concentrations from cell pellets. A stock solution contained standard substances of all the targeted nucleotides, nucleosides, and nucleobases were prepared at 200 nmol/mL for each in an internal standard solution of $^{13}C$- and/or $^{15}N$-labeling AMP, ATP, GMP, GTP, UMP, UTP, adenine and adenosine. This solution was serially diluted with the same solution to prepare 10-point calibration solutions in a concentration range of 0.0001 to 50 µM. 10 µL of the supernatant of each sample was mixed with 90 µL of the internal standard solution. 10 µL aliquots of the sample solutions and the standard solutions were injected into a C18 LC column (2.1*150 mm, 1.9 µm) to run UPLC-MRM/MS on a Waters Acquity UPLC system coupled to a Sciex QTRAP 6500 Plus mass spectrometer operated in the negative-ion mode for detection of nucleotides. The mobile phase was a triethylamine buffer (A) and acetonitrile/methanol (1:1) (B) for binary gradient elution (5% to 60% B in 25 min), at 0.25 mL/min and 55° C. For quantitation of nucleosides and nucleobases, 10-µL aliquots of the sample solutions and the standard solutions were injected onto a polar reversed-phase C18 column (2.1*100 mm, 1.6 µm) to run UPLC-MRM/MS on a Waters Acquity UPLC system coupled to a Sciex QTRAP 6500 Plus mass spectrometer operated in the positive-ion mode. The mobile phase was 0.1% formic acid-ammonium formate buffer (A) and methanol (B) for binary gradient elution (0% to 40% B in 15 min), at 0.25 mL/min and 30° C. Concentrations of the detected nucleotides, nucleosides or nucleobases in the UPLC-MRM/MS runs were calculated with internal-standard calibration by interpolating the constructed linear-regression curves of individual compounds, with the analyte-to-internal standard peak area ratios measured from the sample solutions.

Statistical Analysis of Purine and Pyrimidine Concentrations

The effect of treatment on the concentration of purines and pyrimidines for both cell lines and xenograft were modelled as concentration=Treatment1+Treatment2+Treatment1*Treatment2. For cell lines, Treatment 1-2 were Carbo and Teri, while for the xenografts—Lur and Leflu respectively. The significance of the effects was ascertained by p-values associated with the coefficients of the model (20). The p-values were FDR corrected to account for repeated testing. The coefficient for the interaction term (Treatment1*Treatment2) and its associated p-value correspond to the synergistic effect of the two treatments. Coefficients and p-values for the rest of the terms indicate significance of each treatment alone. Statistical analysis was conducted in R.

Spheroid Growth and Staining

SBC3 and H446 cells were plated at a density of 10,000 cells per well in 96-well ULA round-bottomed plates (S-Bio, Hudson, NH) and incubated for 72 h at 37° C., 5% $CO_2$, and 95% humidity. Spheroids were transferred to low cell attachment dishes, grown for two days, and treated with drug. After treatment, spheroid samples were run with Western blot assay. For spheroid mitochondria visualization, they were stained with 250 nM MitoTracker® Red CMXRos and Hoechst from ThermoFisher Scientific (Waltham, MA) for 2 h after drug treatment. Spheroids were washed, fixated with 4% PFA, transferred into 96-well flat glass-bottom black microplate (Cellvis, Mountain View, CA), and mounted in wells.

Image Acquisition H446 Spheroids

Images were acquired on an LSM 880 inverted microscope (Carl Zeiss) controlled with Zen software (2.3 Black), equipped with a 63×/1.4 NA Plan-Apochromat Oil objective, and captured with GaAsP-PMT detectors. Z-stacks were acquired in Airyscan Fast mode with a 2.0 µm interval and optical zoom of 2.0. Images had a width and height of 1900×1900 pixels, and spatial resolution of dx=0.04 µm, dy=0.04 µm and dz=2 µm. In Airyscan Fast mode excitation was provided by 405 nm (1.0%) and 561 nm (1.0%) lasers with gain and detection wavelengths: DAPI 670V (450 nm) and Red 650V (579 nm). 2D images were acquired with a 20×/0.8 NA Plan-Apochromat objective and captured with PMT detectors. Images had a width and height of 2580×2580 pixels, and spatial resolution of dx=0.08 µm and dy=0.08 µm. Excitation was provided by 405 nm (0.3%) and 561 nm (0.2%) lasers with gain and detection wavelengths: DAPI 669.1V (410-490 nm) and Red 639.1V (569-620 nm).

Imaris Method for Analysis of 2D Cell Monolayer and Spheroid Images

Imaris 9.9.0 (Bitplane, AG), with Surfaces and Cells modules, was used to generate mitochondria morphology data from 2D images and 2D Z-stack subsets. Surfaces were used to evaluate individual mitochondria from cell monolayers and spheroids. Detection parameters were optimized for visible mitochondria and nuclei in each group with varying signal intensities. Roundness ratios were calculated from Surface generated Bounding Box 00 Length measurements. Object lengths less than 0.1 µm were excluded, and lengths greater than 1.26 µm were separately analyzed as clusters. Thresholds were uniformly applied to roundness ratios to categorize mitochondria morphology as elongated (<0.599), intermediate (≥0.600-0.649), or round/fragmentated (≥0.650). The percentage of cells from total number is based on a ratio. A perfectly round object has a ratio of 1.0. The Cells module was used to detect and quantify mitochondria and nucleus area from cell monolayers. Identical parameters were applied to all groups with cell boundary detection based on mitochondria signals. Imaris includes nuclei in cytoplasm measurements, so mitochondrial area is calculated by subtracting nucleus area from cell cytoplasm area. Abnormal nuclei were excluded (<100 $\mu m^2$, >750 $\mu m^2$).

Spheroid LDH Assay

LDH activity was measured using LDH Cytotoxicity Assay Kit following the manufacturer protocol (Thermo Fisher Scientific, Waltham, MA). Briefly, H446 and SBC3 spheroids after 72 hours of drug treatments were mixed with 10 µl 10× lysis buffer and incubated for 45 min in cell culture incubator. 50 µl of lysed cells from each sample were used to measure absorbance by plate reader (Tecan Spark 10, Salzburg, Austria). Percentage of cell cytotoxicity/death was calculated by using the following formula:

$$\%\ \text{Cytoxicity} = \left[\frac{\text{Compound−treated } LDH \text{ activity} - \text{Spontaneous } LDH \text{ activity}}{\text{Maximum } LDH \text{ activity} - \text{Spontaneous } LDH \text{ activity}}\right] \times 100$$

Spheroid MitoSOX Assay

The IncuCyte system recorded two days MitoSOX red dye (Thermo Fisher Scientific, Waltham, MA) penetration in live H446 spheroids. Spheroids were labeled with 5 µM of dye and red fluorescence was assessed by IncuCyte software. Fluorescence and brightfield images were acquired on an Axio Observer 7 (Carl Zeiss, Jena, Germany) inverted microscope, equipped with a 10×/0.45 NA Plan-Apochromat objective, TL halogen lamp, Colibri 7, filter set 90 HE, and captured on a Zeiss Axiocam 702 CMOS camera. Exposure times and wavelengths were 15 ms (red fluorescence), 9.4 ms (brightfield), BP 555/30 excitation filter, and QBP 592/25 emission filter.

Spheroid ATP Assay

Cell titer glo/ATP assay (Promega, Madison, WI) was used for ATP measurement in spheroids. After 72 h of drug treatments, intracellular spheroid's ATP concentration was measured by luminescence following the manufacturer protocol using Tecan Spark 10 plate reader.

RNA Isolation and Data Processing

The total RNA was extracted from SBC3 control, Teri (3200 nM), Lur (1600 μM) and Teri/Lur treated spheroids for 24 hours and purified using the RNeasy Plus Mini kit (Qiagen, Hilden, Germany), according to the manufacturer's instructions. All samples passed QC/quality control and met the requirement of poly-A-selected-RNAseq protocol. The sample libraries were sequenced on Illumina HiSeq4000 (Illumina, San Diego, CA) to generate 101 bps paired-end reads. Before aligning the reads to the reference genome, the adaptor sequences and polyA sequences were trimmed and filtered out using fastp (ver 0.23.2) (21). The RNA-seq data was aligned to the reference sequence (hg38) using STAR (ver 2.7.9) (22) with Gencode annotation database (v 38). The R Subread package with the featureCount function generated RNA-seq raw counts for quantification (ver 2.0.3) (23). Very low expressed genes with maximum expression <0.1 RPKM from all samples are excluded for downstream differential expression analysis. The differential expression analysis of RNA-seq were applied using DESeq2 package (ver 1.38.2) (24). The heatmap of differentially expressed genes were generated using R heatmap (ver 1.0.12). The genes were sorted by signed p-value for the gene set enrichment analysis which were applied using R clusterProfiler (ver 4.6) (25) with KEGG pathway database (https://www.genome.jp/kegg/pathway.html). The dot plot for differentially expressed genes were generated using R ggplot2 (ver 3.4).

In Vivo Xenograft Studies

Athymic nude nu/nu mice were obtained from Charles River, Wilmington, MA, and were acclimated for a week before beginning the experiment. All animal experiments were carried out in accordance with a protocol approved by the Institutional Animal Care and Use Committee COH (IACUC #16004). For treatments, mice were divided into 4 groups with five mice per group and subcutaneously injected into one flank with $2\times10^6$ SBC3 or SBC5 cells suspensions in 100 μl of PBS. Treatment started on the 14th day when tumors became palpable. Two in vivo studies were done in this project. SBC3 and SBC 5 xenograft with i) vehicle control, ii) Carbo 50 mg/kg, iii) Leflu 7.5 mg/kg, and iv) Carbo/Leflu. SBC3 with i) vehicle control, ii) Lur 0.5 mg/kg, iii) Leflu 3.8 mg/kg, and iv) Lur/Leflu. Treatments were given to mice via i.p. twice a week for 6 weeks. Animals were examined daily for signs of tumor growth. Tumors were measured in two dimensions using calipers and body weights were recorded. Animals were photographed on days 1, 5, 10, 15, 20, 25, 30, 35, and 40 after treatment. Tumors were removed on day 40 and photographed. At the end of the study, the mice were euthanized by $CO_2$ asphyxiation followed by cervical dislocation. The tumor weights were compared between groups using an unpaired Student's t-test. A portion of the tumor was fixed in 10% buffered formaldehyde solution and paraffin-embedded for immunostaining. FFPE tumor sections were stained with pDRP $Ser^{616}$ antibody. Tumor sections were deparaffinized and rehydrated, followed by heat-mediated antigen retrieval (pH 6, Dako). After permeabilization and blocking, tumor sections were stained with pDRP1 $Ser^{616}$ antibody overnight, washed and incubated with Alexa 488 secondary antibody for one hour, mounted and observed on an LSM 880 with a 10×/0.45 NA objective (Carl Zeiss). Immunofluorescent confocal images were acquired for each treatment (magnification:100×). Mean immunofluorescence intensities were calculated with ZEN 2.3 Lite software.

Statistical Analysis

All data represent means±SE or means±SD. Two sample groups were compared by unpaired, two-sided Student's t tests. Data from more than two groups were analyzed by one-way ANOVA followed by Tukey's multiple comparison tests. Values of $p<0.05$ were considered significant and indicated as: *$p<0.05$, $p<0.01$, *$p<0.001$. Data analysis was conducted using GraphPad Prism 8 software (La Jolla, CA).

Leflu and Teri Bind DRP1

Figure 1B:
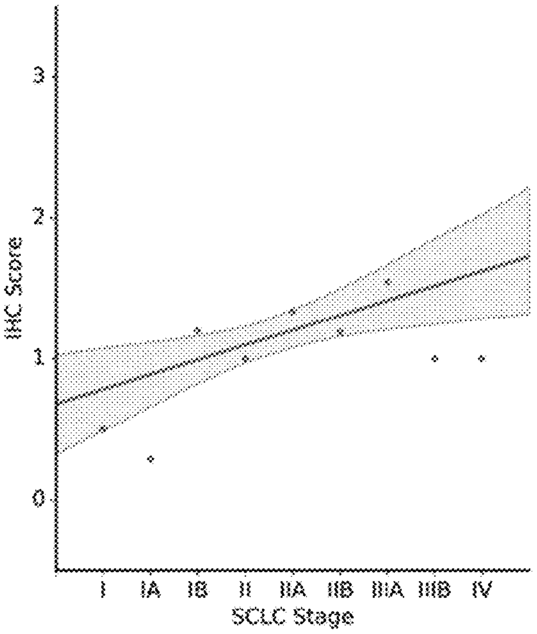

IHC of DRP1 expression in disease specimens was determined using SCLC TMAs. TMA staining was quantified as ranging from 0-3 using a semi-quantitative visual index. Representative images of immunohistochemical staining of DRP1 are shown in FIG. 1A and DRP1 immunostaining was observed to increase in intensity with disease progression. A regression analysis showed a significant positive correlation between DRP1 score and stage of tumor (p=0.002) (FIG. 1B). These data suggest that there is increased mitochondrial fission activity in lung cancer cells that is driven by increased DRP1 expression.

Figure 1C:
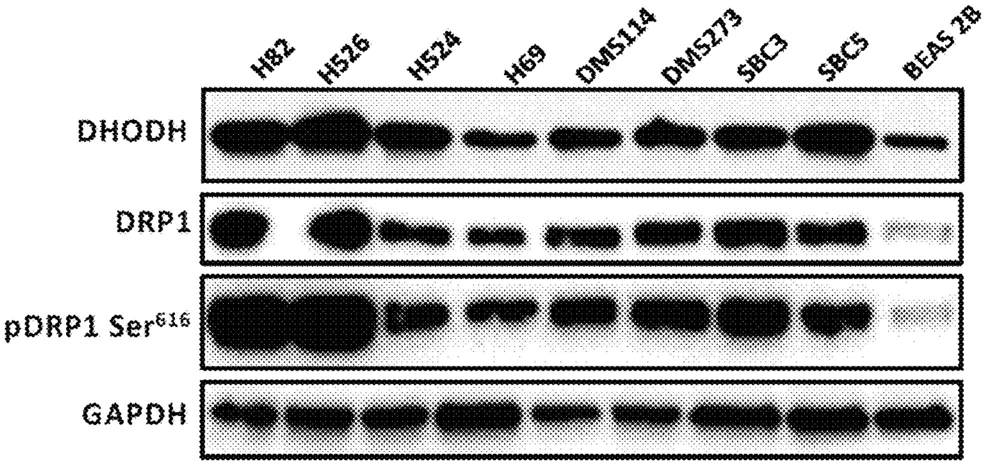
Figure 2A:
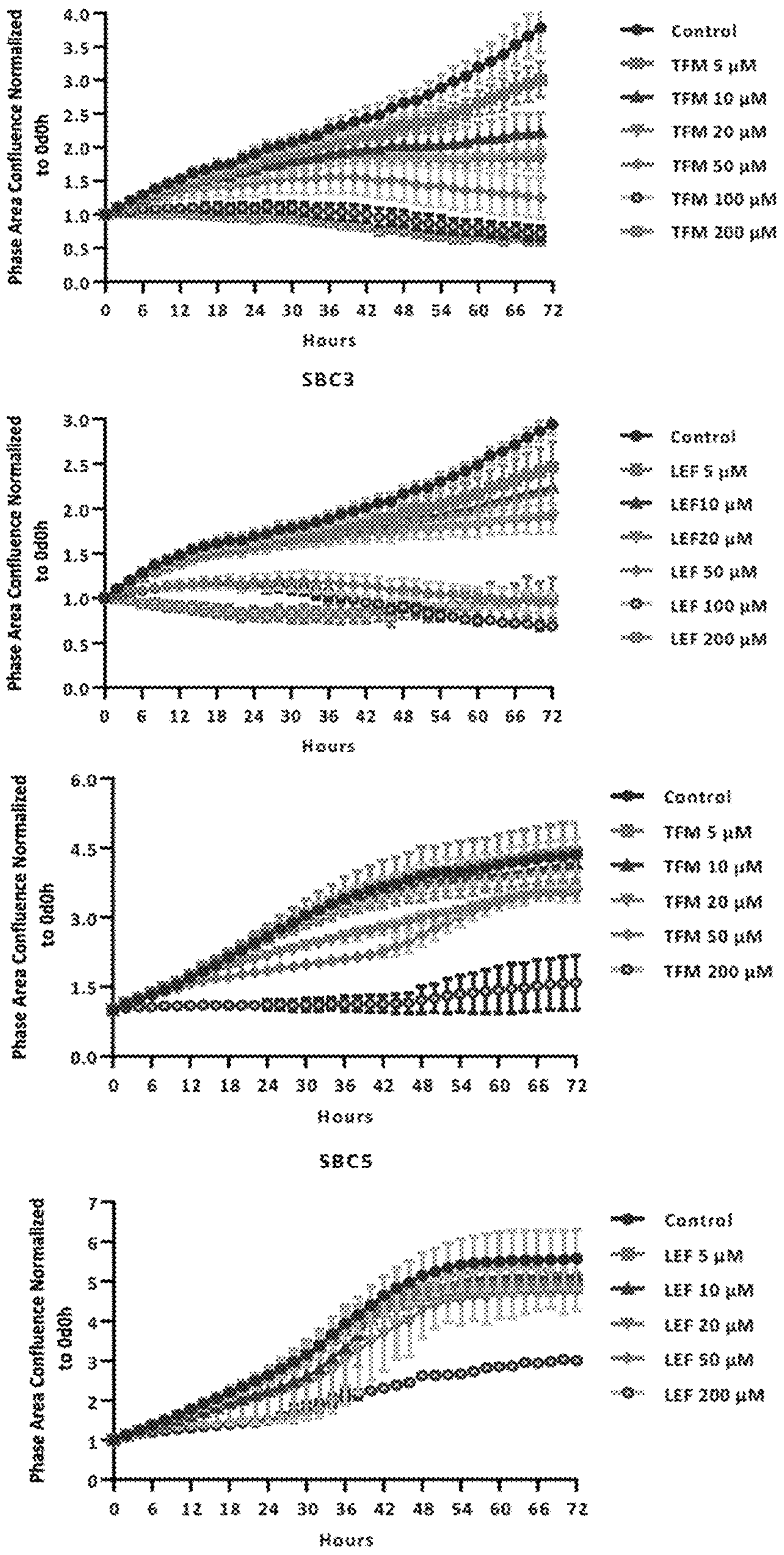
FIGS. 2A-2I. Teriflunomide (Teri) affects the phosphorylation of DRP1 at $Ser^{616}$ and mitochondrial/nuclear morphology.

The expression levels of DRP1 and DHODH in SCLC lines were compared with non-malignant BEAS 2B cells. Elevated levels of DRP1 and pDRP1 at $Ser^{616}$ were detected in all tested SCLC cells. Higher expression of DHODH was also observed in all seven SCLC cell lines (FIG. 1C). Previous studies have shown that Leflu and its active metabolite Teri regulate mitochondrial morphology (9,10, 26). To find the effects of these two drugs on DRP1, AA docking (27) method was used to search for the best binding pocket for inhibitor binding. We identified that Teri and Leflu preferably binds at the GDP-binding site with relatively higher docking scores, while MDV1 binds at an allosteric site (Site-2). Teri shows the highest docking score (−8.02 kcal/mol) in the GDP-binding pocket. Leflu has a medium docking score of −5.6 kcal/mol. MDV1 shows the lowest docking score (−3.66 kcal/mol) with weaker interactions with DRP1 (Table 2). Amino acids involved in interactions between Leflu, Teri, MDV1, and DRP1 are shown in Table 2. In vitro cytotoxicity effect of Teri and Leflu was tested in a panel of SCLC cell lines. $IC_{50}$ values are reported in Table 3. Ten SCLC cell lines were treated with increasing concentrations of each drug for 72 h. It was observed that five cell lines were sensitive to Teri with $IC_{50}$ less than 11 μM. In contrast, $IC_{50}$ doses were much higher for Leflu. Upon oral administration of Leflu, over 80% of the drug is converted to Teri (28), indicating a potential reason for higher sensitivity to Teri. Two cell lines, SBC3 and SBC5, with $IC_{50}$ 2 μM and 30 μM, respectively, for Teri were used for additional experiments. Treatment of SBC3 and SBC5 cells with Leflu or Teri inhibited cell proliferation in a dose-dependent manner. The inhibitory effect was higher with Teri in both cell lines (FIG. 2A). These data suggest that inhibition of SCLC cells with Teri or Leflu in vitro model reduces the growth of lung tumors.

TABLE 2

Targeting of DRP1 by leflunomide (Leflu) and teriflunomide (Teri) directly in SCLC. To find the effects of these two drugs on DRP1, AA docking method was used to search for the best binding pocket for inhibitor binding. We identified that teriflunomide (Teri) and leflunomide (Leflu) preferably binds at the GDP-binding site with relatively higher docking scores, while MDV1 binds at an allosteric site (Site-2). Teri shows the highest docking score (−8.02 kcal/mol) in the GDP-binding pocket. Leflu has a medium docking score of −5.6 kcal/mol. MDV1 shows the lowest docking score (−3.66 kcal/mol) with weaker interactions with DRP1. The last column includes amino acids involved in interactions between Leflu, Teri, MDV1, and DRP1. Protein model for each: DRP1.

| FDA approved drug | Compound | Target | Disease | Docking score (kcal/mol) | Binding site | No. of H-bonds | No. of hydrophobic pairs | No. of π-interactions | Amino acid involved in interacttion |
|---|---|---|---|---|---|---|---|---|---|
| Yes | Teriflunomide | DHODH | Multiple sclerosis | −8.02 | GDP-binding | 3 | 2 | 1 | G37, K38, T59, V58, I252, K216 |
| Yes | Leflunomide | DHODH | Rheumatoid arthritis | −5.63 | GDP-binding | 2 | 1 | 2 | S39, G54, I252, K38, K216 |
| N/A | MDIVI1 | DRP1 | N/A | −3.66 | Site 2 | 1 | 2 | 3 | Q66, I22, L25, N141, Q24, Q12 |
| Traditional Chinese Medicine | Isobavachalcone | DHODH | AML | −7.76 | GDP-binding | 2 | 4 | 2 | S40, G149, L219, V58, I57, I252, K216, K38 |
| Yes (curcumin/ piperine) | Piperine | DHODH | Multiple sclerosis | −5.67 | GDP-binding | 2 | 1 | 1 | Q249, S39, L219, K38 |
| AML in clinical (NCT03760666) | Brequinar | DHODH | Advance solid tumors | −5.86 | Site 2 | 1 | 1 | 5 | R172, L25, N176, Q24, Q27, N178, Q66 |

TABLE 3

| Sensitivity | Cells | IC50 Teriflunomide μM | IC50 Leflunomide μM |
|---|---|---|---|
| 1 | SBC3 | 2 | 8.9 |
| 2 | H82 | 7.2 | 102.9 |
| 3 | H526 | 7.6 | 48.3 |
| 4 | H146 | 8.6 | 152 |
| 5 | H524 | 10.8 | 132.6 |
| 6 | DMS114 | 12.6 | R |
| 7 | H69 | 17.1 | R |
| 8 | SBC5 | 33 | 107.8 |
| 9 | DMS273 | 43.7 | R |
| 10 | H345 | R | R |

DRP1 Phosphorylation is Impacted by Teri/Leflu Treatment

Figure 2B:
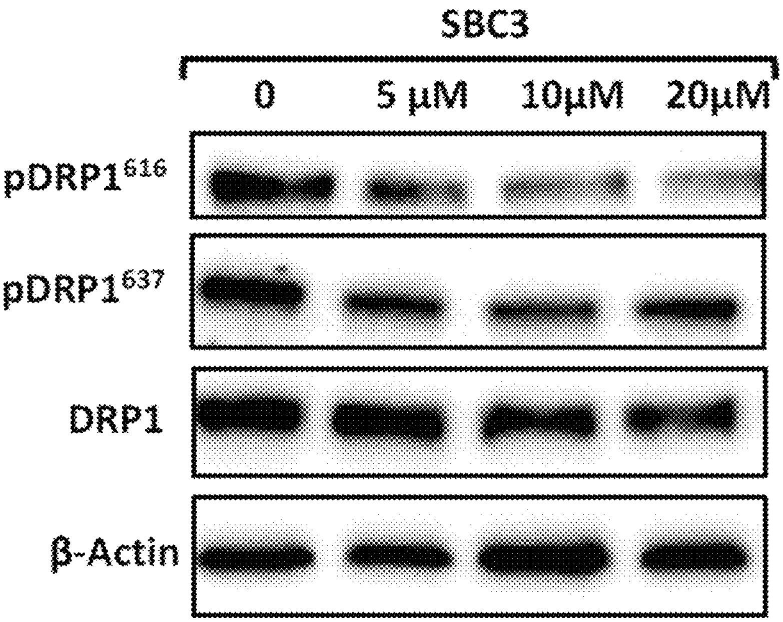
Figure 2C:
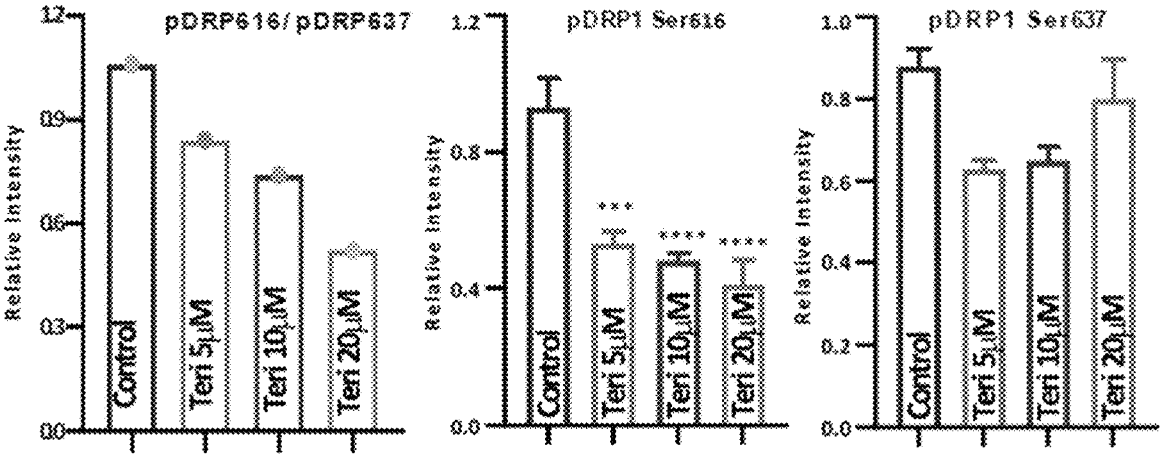

Leflu and Teri are approved DHODH inhibitors used as anti-inflammatory drugs to treat autoimmune and infectious diseases (29). However, preclinical studies have shown significant effects of Leflu and Teri in cancer (30,31). Computational AA docking results demonstrated a high binding score of Teri to DRP1. DRP1 regulates of mitochondrial dynamics and controls fission events (32,33). Treatment of SBC3 with Teri significantly inhibited DRP1 phosphorylation at $Ser^{616}$, and $Ser^{637}$ (FIG. 2B). Additionally, the ratio of pDRP1 ($Ser^{616}$) to pDRP1 ($Ser^{637}$) was significantly decreased in a dose-dependent manner following Teri treatment (FIG. 2C).

Figure 2D:
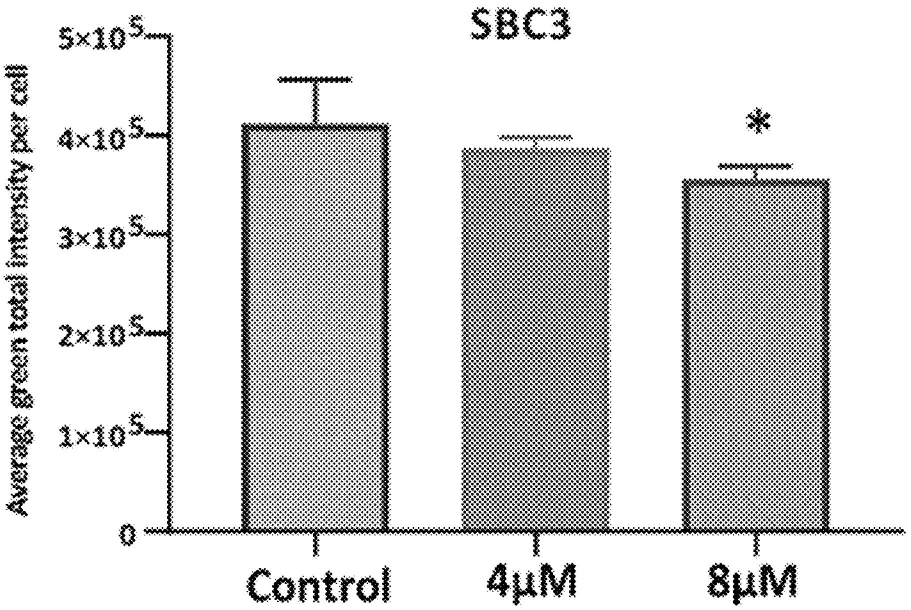
Figure 2E:
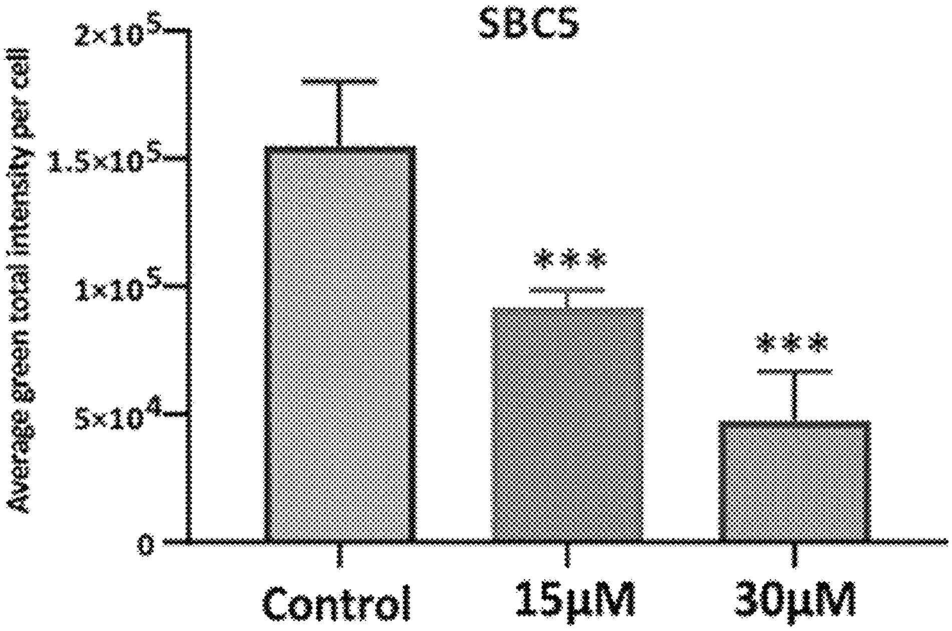

Additionally, SBC3 and SBC5 cells were stained with pDRP1 $Ser^{616}$ antibody (2° ab Alexa488), and the phosphorylation level was analyzed with QuPath 0.2.0M9 software. Quantification of green IF showed significant signal intensity decreased and inhibition of DRP1 phosphorylation in SBC3 and SBC5 cells with Teri treatment (FIGS. 2D-2E).

Figure 2F:
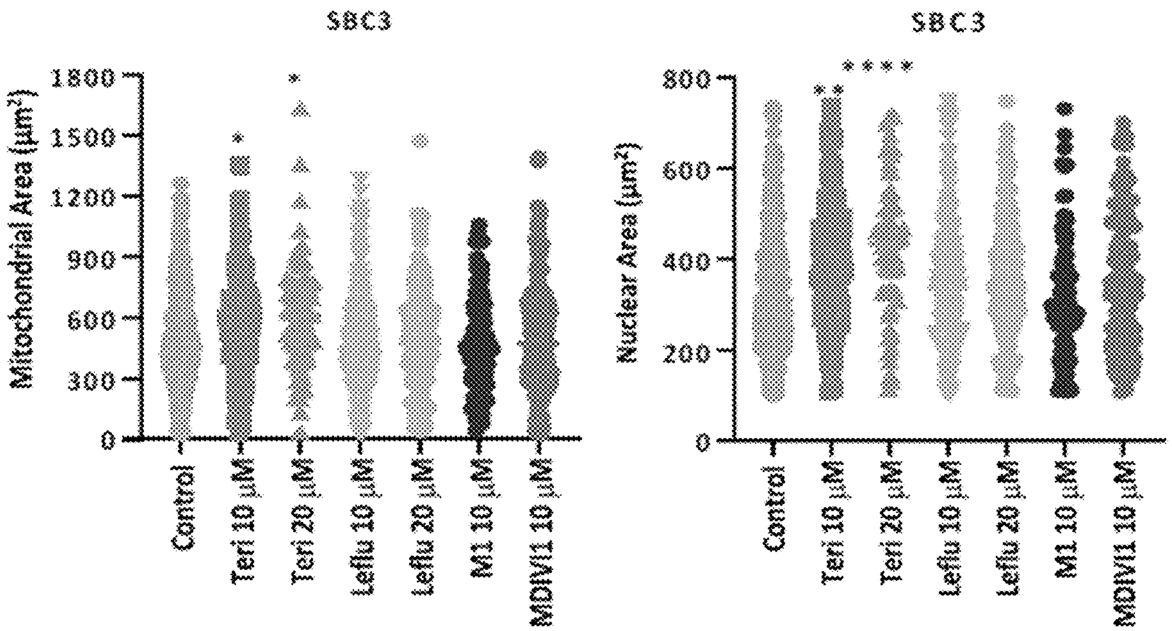

MitoTracker Red and Hoechst 33342 were used to validate Teri and Leflu effects on intact mitochondrial morphology in SBC3 and SBC5 cells. M1 and MDIVI1 compounds were used as positive controls because they are promoters of mitochondrial fusion. Mitochondrial and nuclear areas were quantified by analyzing object surface area and intensity in Imaris 9.9.0. Mitochondrial areas of SBC3 cells were significantly increased after Teri treatments (Control 502.5±11.9 vs 569±19.9 10 μM $μm^2$ ($p=0.0483$); and vs 20 μM 604.8±28.9 $μm^2$ ($p<0.011$) (FIG. 2F, left panel). Mitochondria in control cells were closely packed around the nuclei and treatment with Teri rearranged the mitochondrial network and extended the area from the nuclei. Nuclear size also increased after Teri treatments (Control 339.2±7.33 $μm^2$ vs 10 μM 386.8±10.86 $μm^2$ ($p<0.0055$); and vs 20 μM 423.5±16.57 $μm^2$ ($p<0.0001$) (FIG. 2F, right panel). Leflu, M1, and MDIVI1 did not affect mitochondrial or nuclear areas.

Figure 2G:
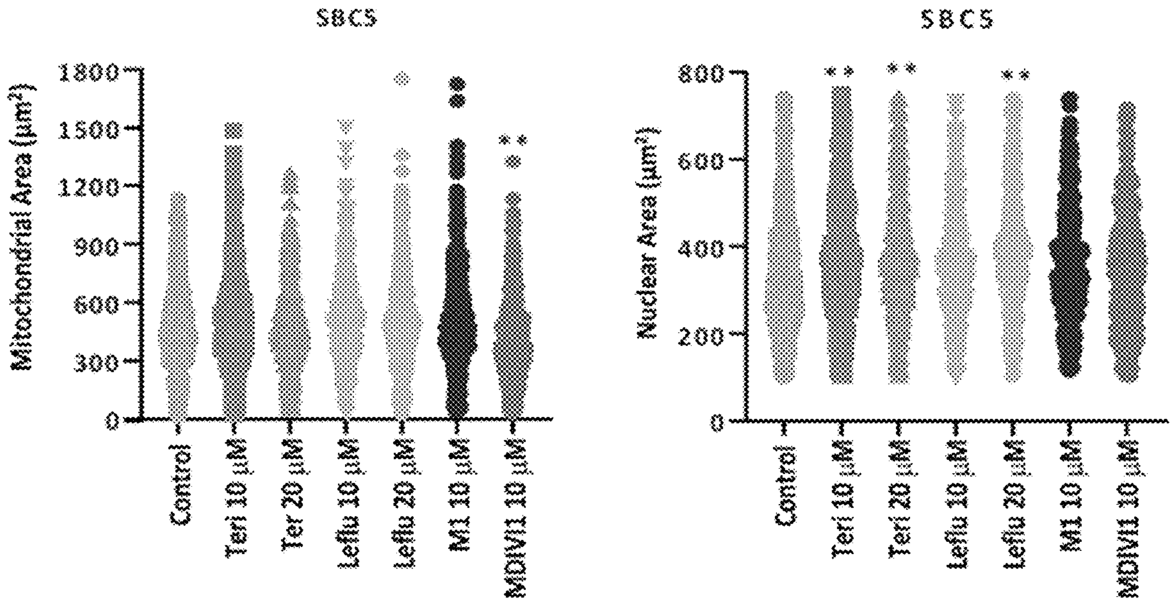
Figure 2H:
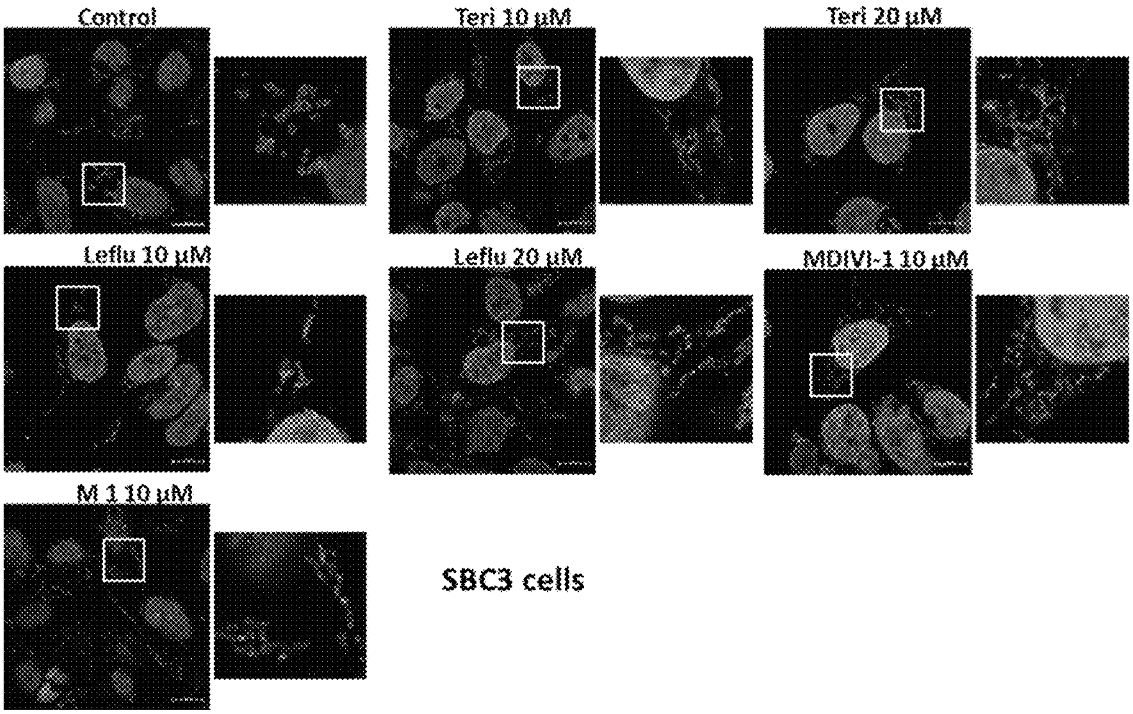
Figure 2I:
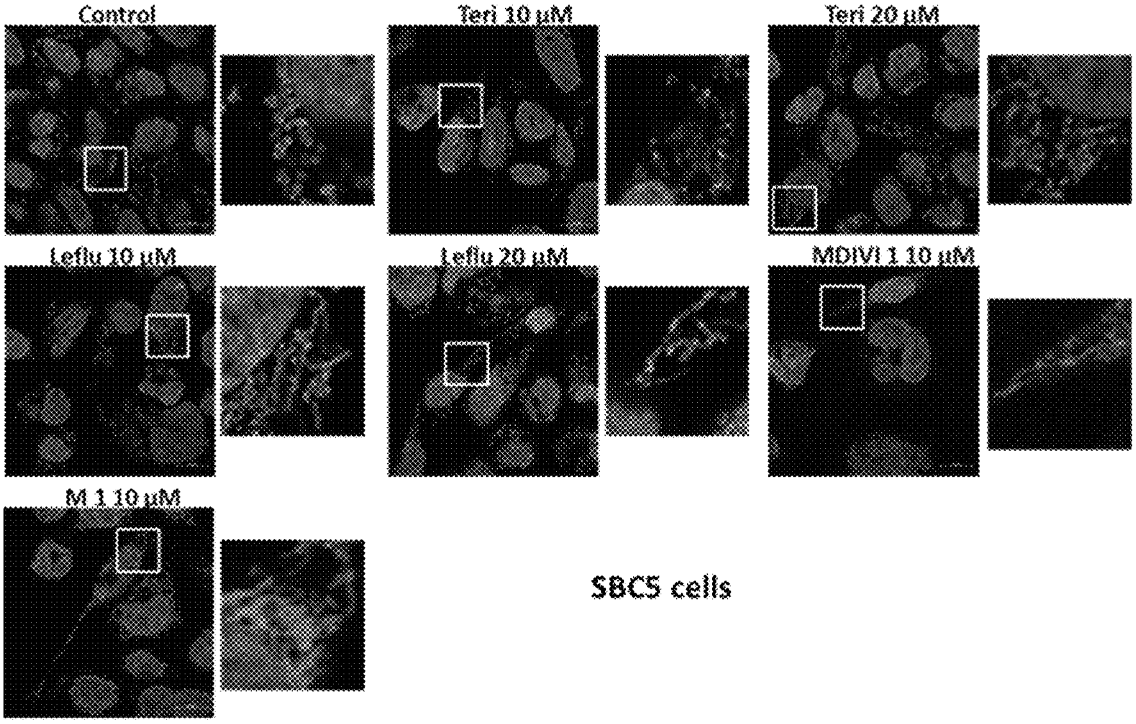

Next, we performed the same analysis with SBC5 cells. Mitochondrial areas were significantly reduced only with MDIVI1 treatment (Control 475.2±9 vs 419.9±13.26 10 μM $μm^2$ ($p=0.0072$) (FIG. 2F, left panel). Significant nuclear enlargement was observed in SBC5 cells treated with Teri and Leflu (Control 337.1±5.77 vs 10 μM 369.5±6.15 $μm^2$ ($p<0.0014$) and vs 20 μM 369.8±5.94 $μm^2$ ($p<0.0017$) Teri; and vs 20 μM Leflu 386.8±7.23 ($p<0.0001$)) (FIG. 2G, right panel). Imaris quantification showed the highest mitochondrial and nuclear area differences in SBC3 cells after Teri treatment. Airyscan high-resolution imaging of mitochondria in SBC3 and SBC5 control groups demonstrated the small round morphology (FIGS. 2H-2I). Mitochondrial elongation in SBC3 cells treated with Teri and Leflu is visible and correlates with Imaris Surface results. M1 and MDIVI 1 treatment groups were moderately affected. Although mitochondrial areas of SBC5 cells were not affected by Teri and Leflu treatments, elongations of individual mitochondria were detected with each treatment (FIG. 2I). Altogether, these data suggest that targeting DRP1 with Teri decreased phosphorylation at $Ser^{616}$ and affected mitochondrial morphology. Therefore, it is important to investigate the effects of Teri and Leflu on mitochondrial morphology and cell survival in combination with chemotherapeutic drugs.

SCLC is Remarkably Responsive to a Combination of Carbo/Teri/Leflu

Figure 3A:
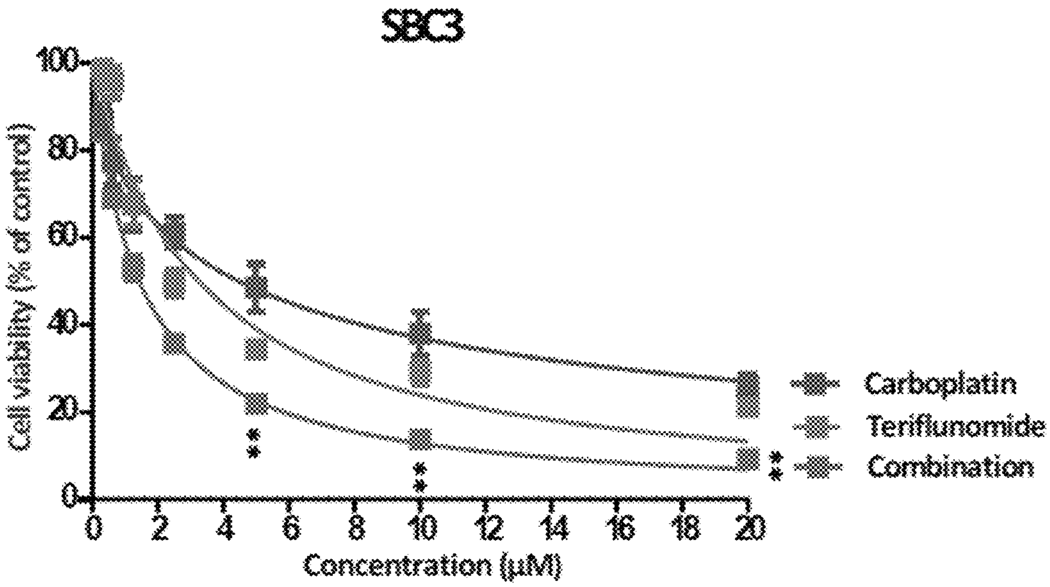
FIGS. 3A-3K. Effect of teriflunomide (Teri) and leflunomide (Leflu) on in vitro and in vivo models in combination with carboplatin (Carbo). SBC3 (FIG. 3A) and SBC5 (FIG. 3C) cells were treated with different concentrations of Teri and Carbo for 72 h. Cell viability was detected by the CCK-8 assay (p<0.01; p<0.0001; Student's t test (n=3, biological replicates)).
Figure 3B:
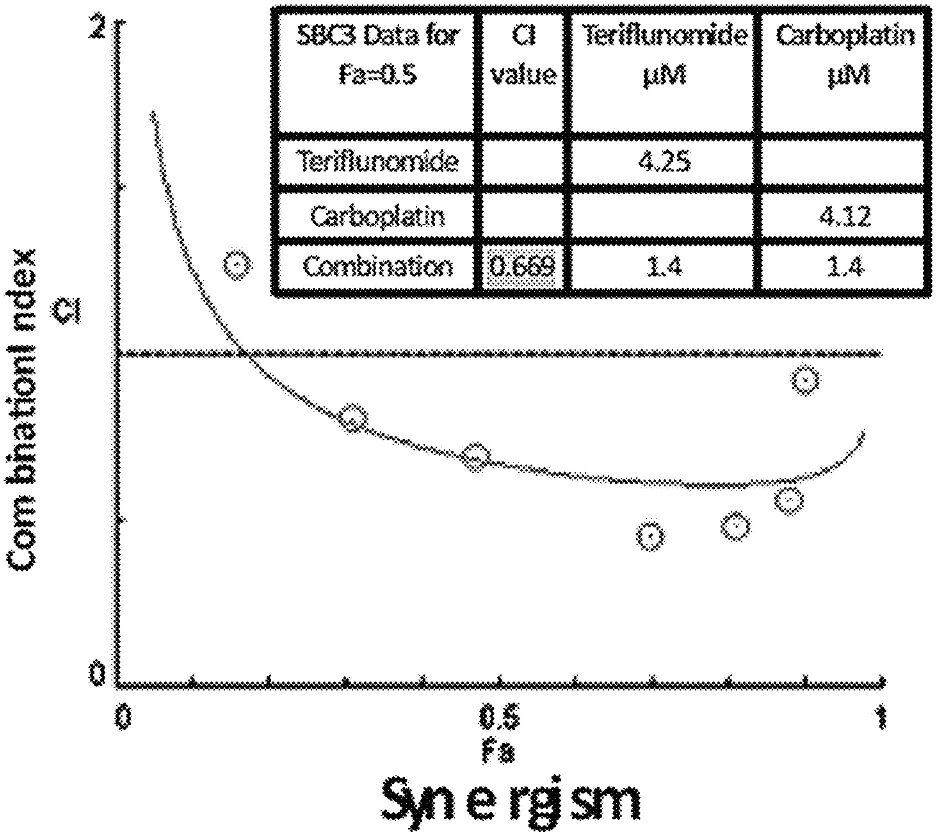
Figure 3C:
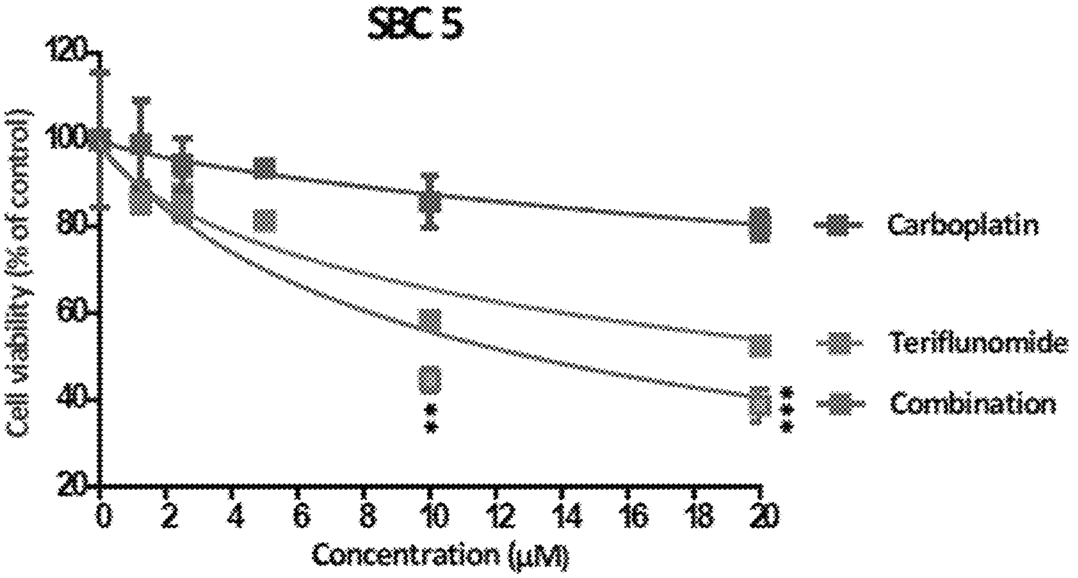
Figure 3D:
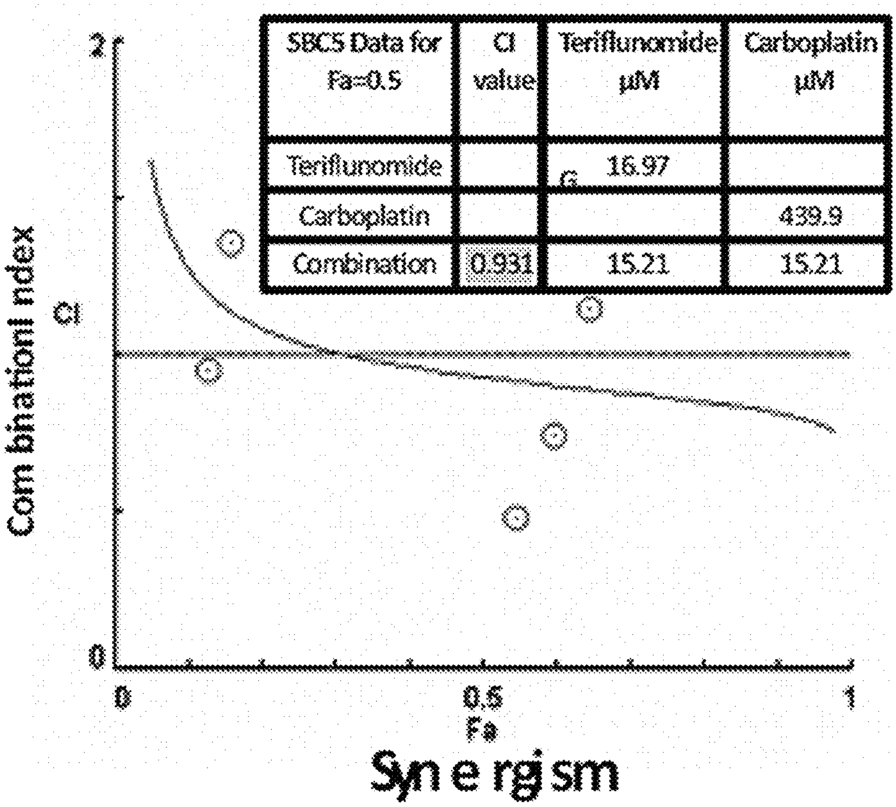
Figure 3E:
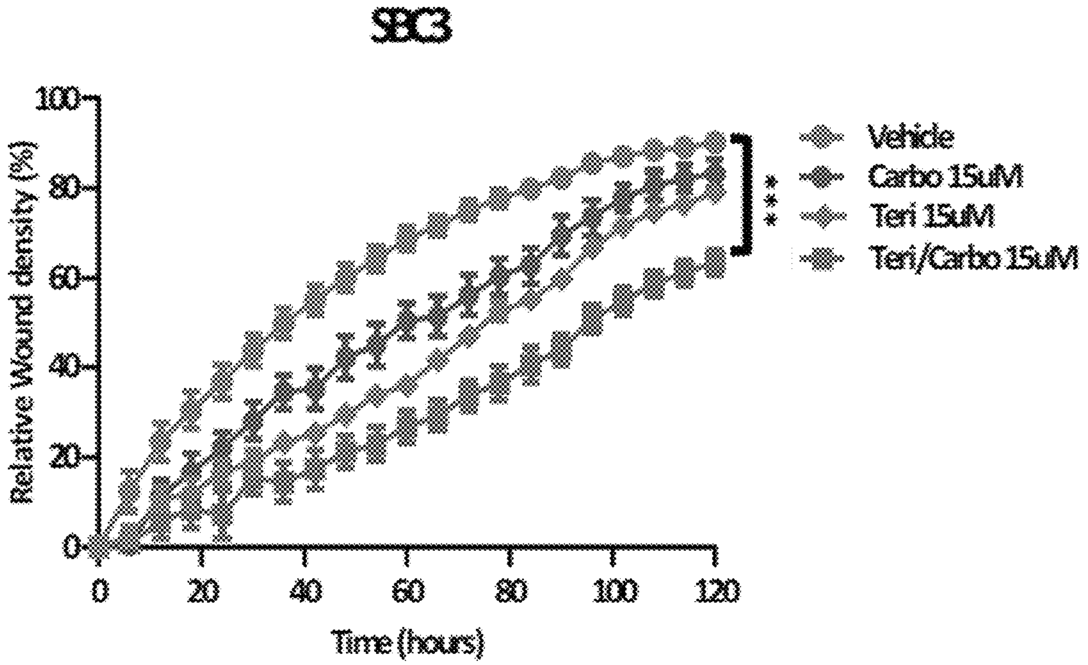
Figure 3F:
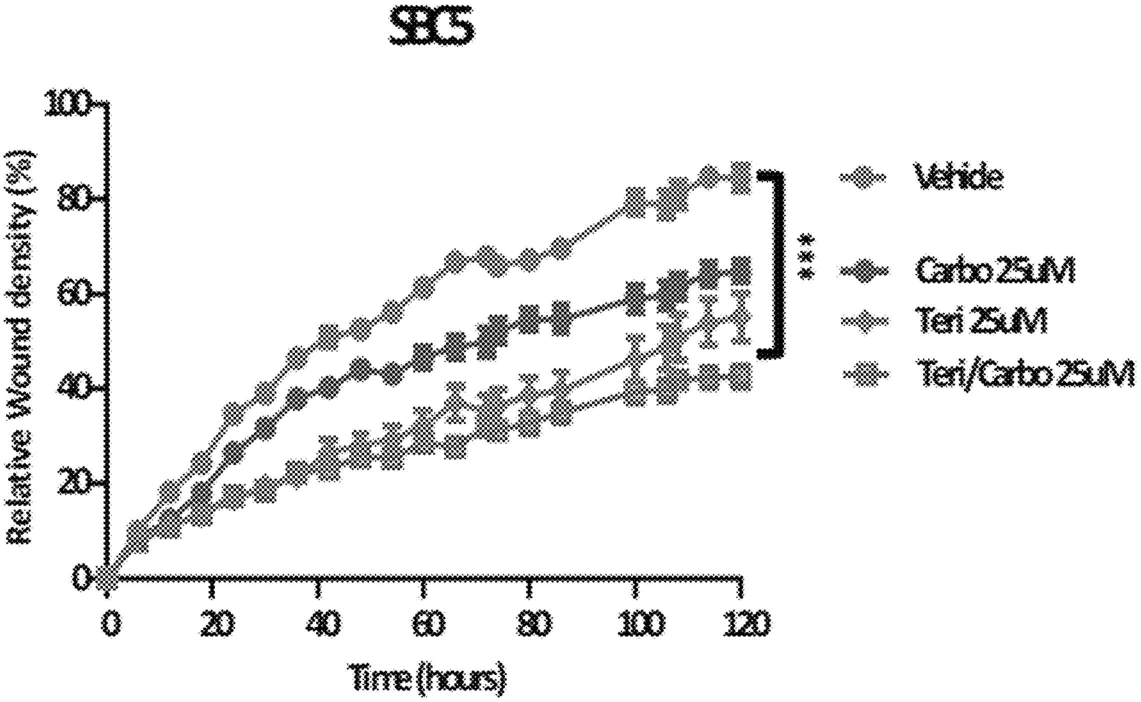

To define the functional effects of Teri and Leflu on SCLC cells in combination with Carbo, we tested two 2D/3D in vitro models, and in vivo mouse xenograft model. Measurement of SBC3 cell viability (FIG. 3A) indicated a reduction of cell viability in combination with several doses of Teri and Carbo (dose range ~4-10 μM). Isobologram and $CI_{50}$ values were calculated using the Chou-Talalay method and $IC_{50}$ to find synergism (FIG. 3B). Synergism was observed with fixed concentrations of Teri and Carbo. The $IC_{50}$ values for a single treatment with Teri (4.24 μM) or Carbo (4.12 μM) were about three-fold higher compared with a combination treatment (1.4 μM). The combination treatment had a $CI_{50}$ value of 0.669, indicating drug synergism of Teri/Carbo. SBC5 cells are less sensitive to Teri/Carbo combination but responded in higher dose ranges (FIG. 3C). Additive interactions of Teri with Carbo were shown in SBC5 cells ($IC_{50}$=0.931) (FIG. 3D). The IncuCyte system was used to evaluate live SBC3 cell migration in the presence of Teri and Carbo. After 24 h, the wound closure percentage of treated SBC3 cells significantly decreased compared to control (FIG. 3E). The significant differences between single drug treatments and combination were observed in later time points over a period of 60 h. A similar response was observed for SBC5 cells (FIG. 3F). Teri/Carbo treatment significantly inhibited wound closure in SBC3 and SBC5 cells in culture.

Figure 3G:
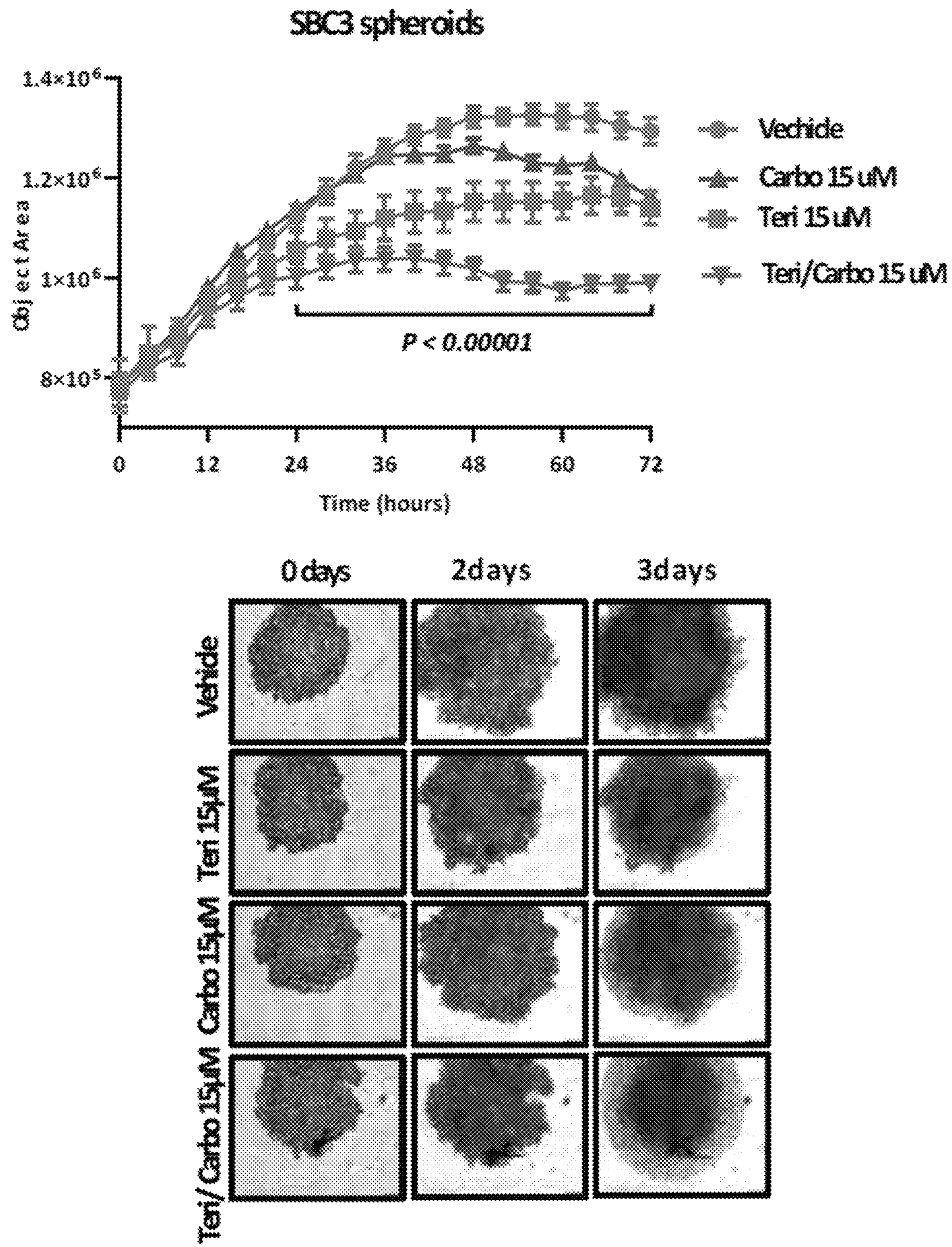

3D spheroid cultures of SBC3 cells were used to model the drug effect on cell proliferation and death. SBC3 spheroid sizes were evaluated with time-lapse images, demonstrating significant differences between the control, single treatments, and combination groups on days 1-3 (FIG. 3G).

Figure 3H:
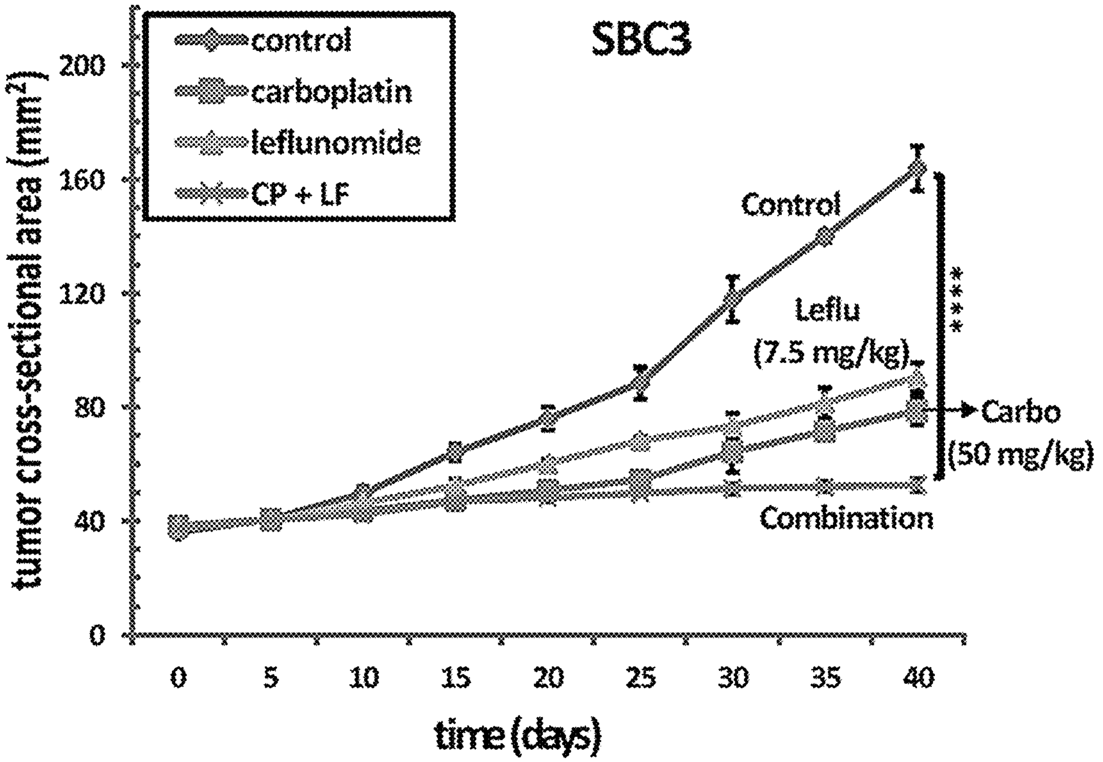
Figure 3I:
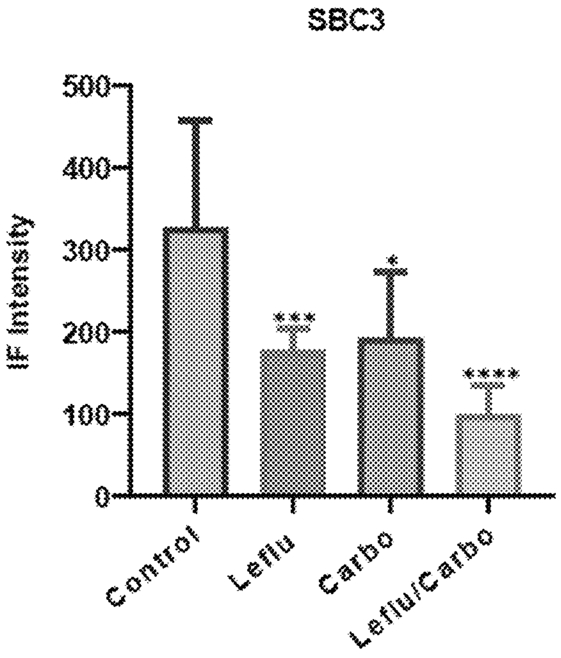
Figure 3J:
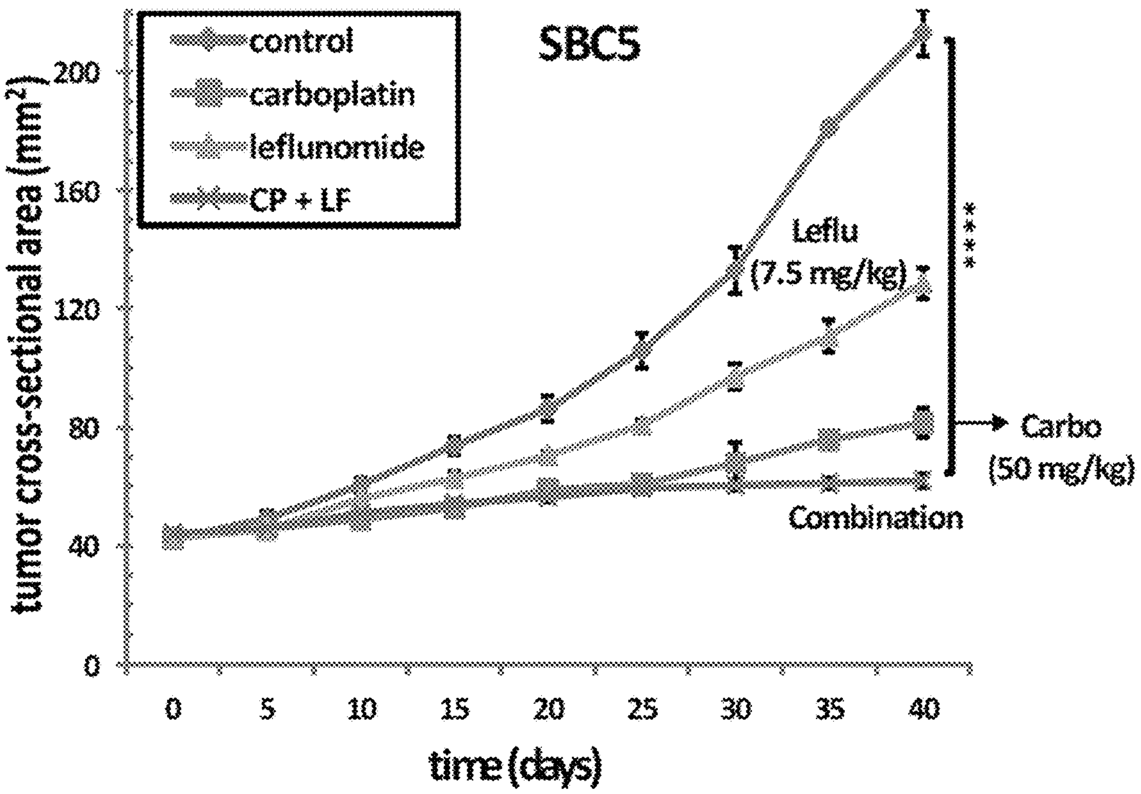
Figure 3K:
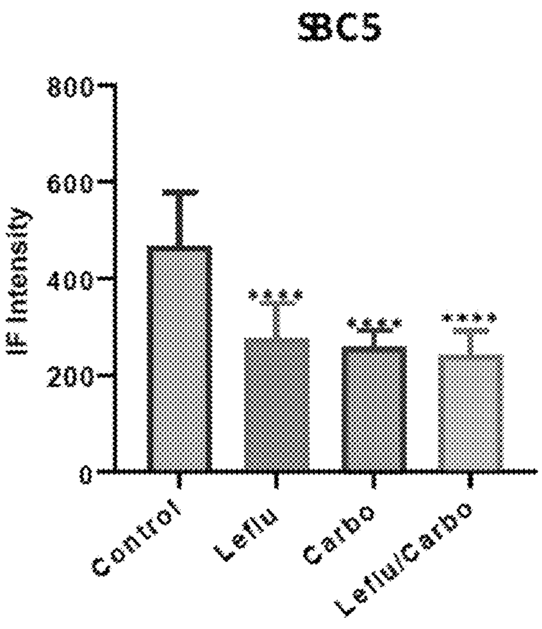

The promising in vitro growth inhibitory effects of Carbo and Leflu led us to evaluate their therapeutic efficiency in xenograft models. The remarkable contrast in the outcome of tumor growth in animals treated with Carbo and Leflu versus vehicle control was clear. The effectiveness of Carbo in reducing tumor growth was comparable to Leflu treatment in the SBC3 xenograft. The average final size of tumors at the end of the study (day 40) in treated animals was significantly lower compared to the control (control—1.67±0.12 g; vs. treated: Carbo—0.75±0.10 g, Leflu—1.01±0.14 g, and Leflu/Carbo—0.32±0.04 g). Treatment with Carbo and Leflu alone caused a ~58% and ~36% reduction in tumor size, respectively. A much higher reduction of ~82% in tumor weight was observed in combinatorial treatment (FIG. 3H). Overexpression or activation of DRP1 through $Ser^{616}$ phosphorylation was linked to a malignant phenotype in various epithelial and endocrine tumors (34, 35). We stained FFPE tumor sections with pDRP1 antibody. Quantitative analysis of immunofluorescence staining showed high DRP1 phosphorylation at $Ser^{616}$ in untreated tumors. A significant decrease in pDRP1 was observed after Leflu and Carbo treatments. Importantly, combination treatment more effectively inhibited DRP1 phosphorylation (FIG. 3I). Treatments in SBC5 mouse xenograft demonstrated the inhibition of tumor growth after Leflu or Carbo and Leflu/Carbo treatments (control—2.01±0.19 g; vs. treated: Carbo—0.64±0.10 g, Leflu—1.49±0.20 g, and Leflu/Carbo—0.54±0.06 g). Maximal inhibition was observed with Leflu/Carbo on tumor xenograft growth curve (FIG. 3J). Immunofluorescence staining of pDRP1 at $Ser^{616}$ was comparable with SBC3 xenograft. A higher inhibitory effect was observed after Leflu/Carbo treatment than control or single drug treatments (FIG. 3K). Together, these results confirm the antitumor effects of Teri/Carbo in 2D cell culture and 3D mouse xenograft models.

Figure 4A:
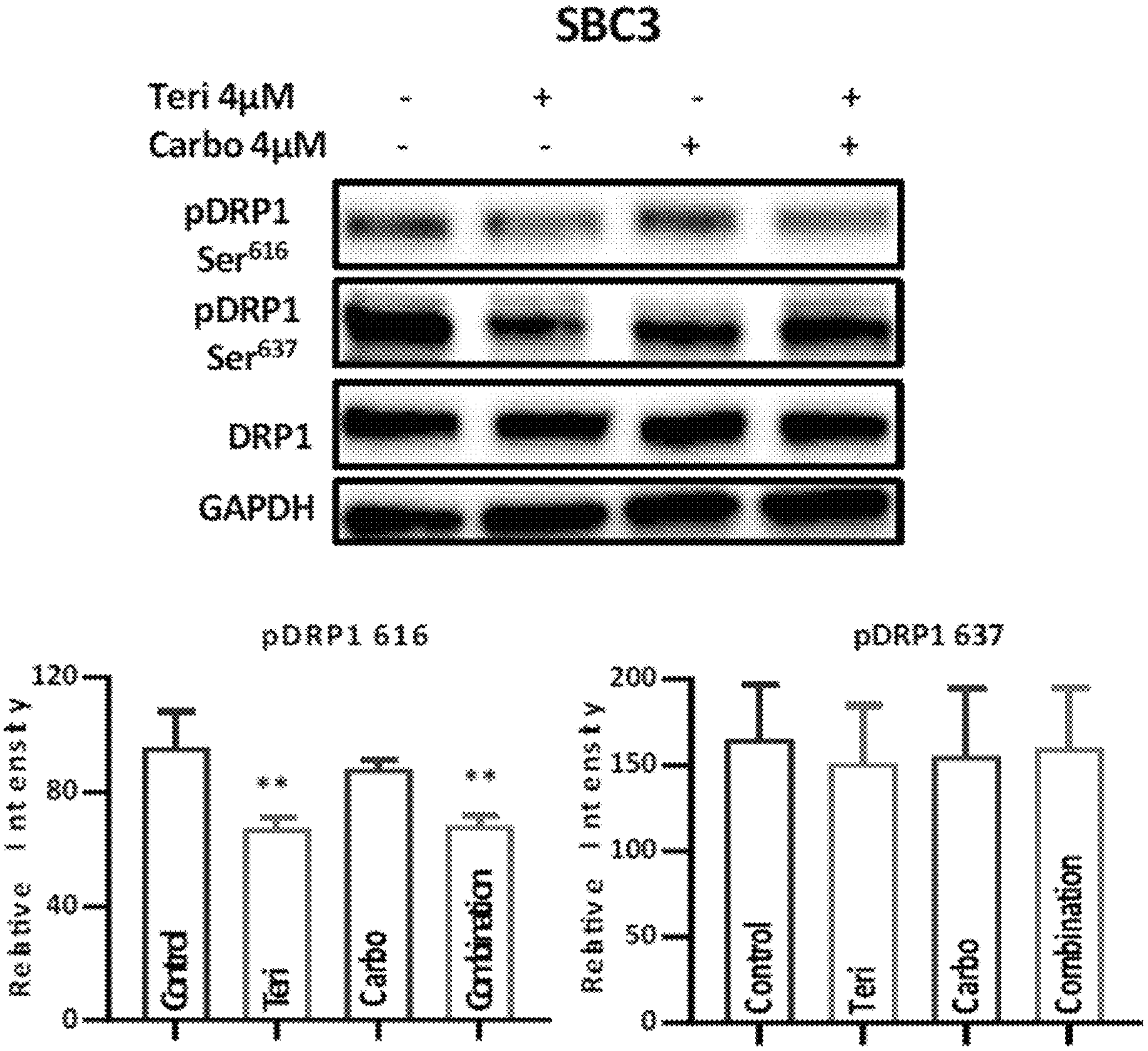
FIGS. 4A-4K. Inhibition of DRP1 phosphorylation at Ser616 by Teri increases SCLC cells susceptibility to Carbo.

Teri/Carbo Combination Affects DRP1phosphorylation, Apoptosis, DNA Damage and Disrupts the Purine-Pyrimidine Pool Our initial results demonstrated an inhibitory effect of Teri in SBC3 cells on DRP1 phosphorylation at $Ser^{616}$. We next evaluated the effect of Teri/Carbo on DRP1 phosphorylation. Phosphorylation at $Ser^{616}$ was significantly decreased only in SBC3 cells (FIG. 4A). Teri/Carbo treatment in SBC3 cells did not change the total and $Ser^{637}$ site DRP1 levels (FIG. 4A). Mitochondrial morphology plays a crucial role in cellular functions, including metabolism, cell proliferation, and apoptosis (32,36). DRP1 regulates mitochondrial fission by increasing phosphorylation at $Ser^{616}$ and drives the mitochondrial dynamic towards fission (37). Studies have reported fission/fusion protein ratio alterations in pancreatic, breast, head, and neck squamous cell carcinoma and lung cancer (38,39). Overexpression of fission proteins, including DRP1, has been correlated with resistance to drug treatment and uncontrolled proliferation (6,40).

Figure 4B:
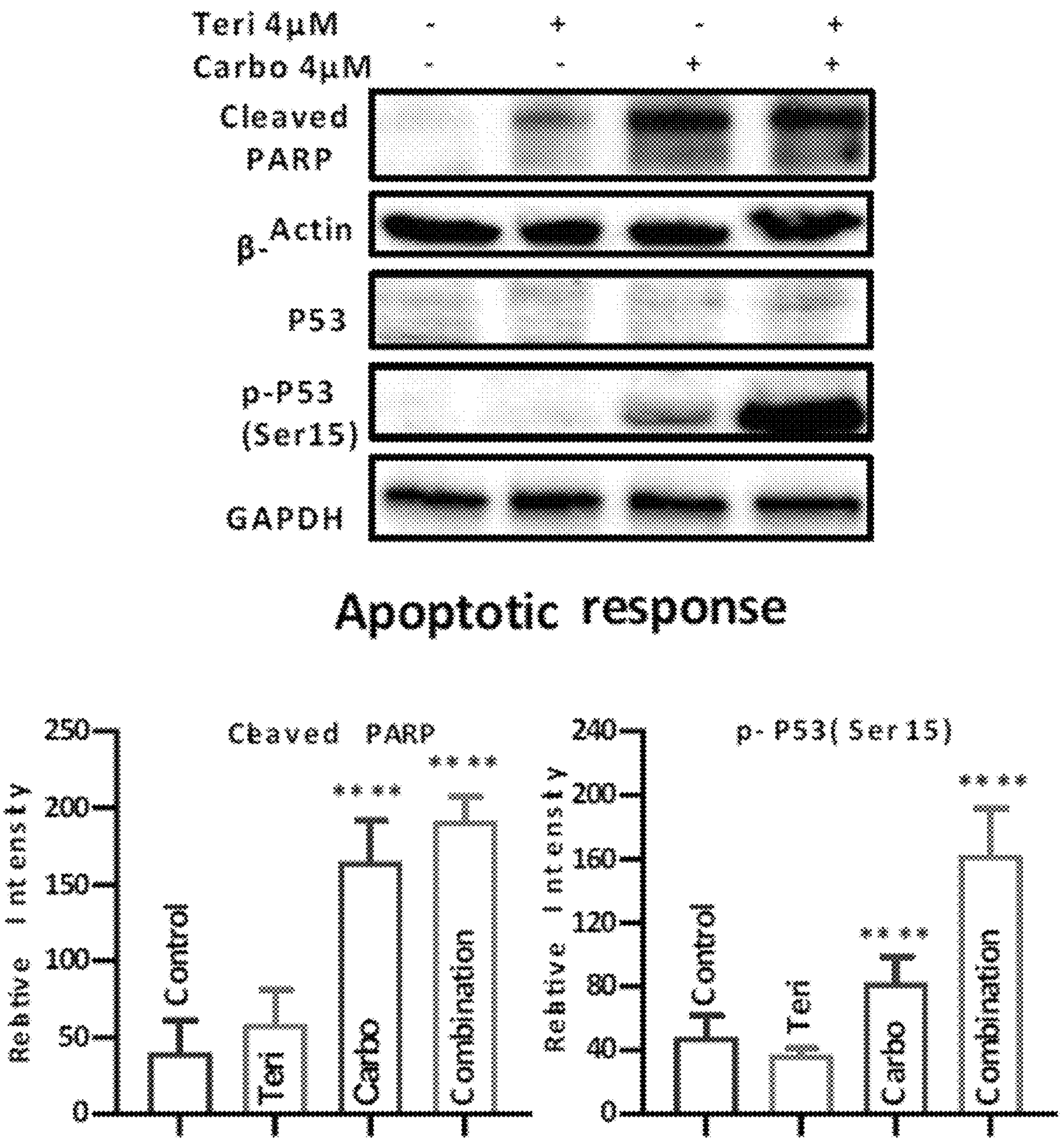
Figure 4C:
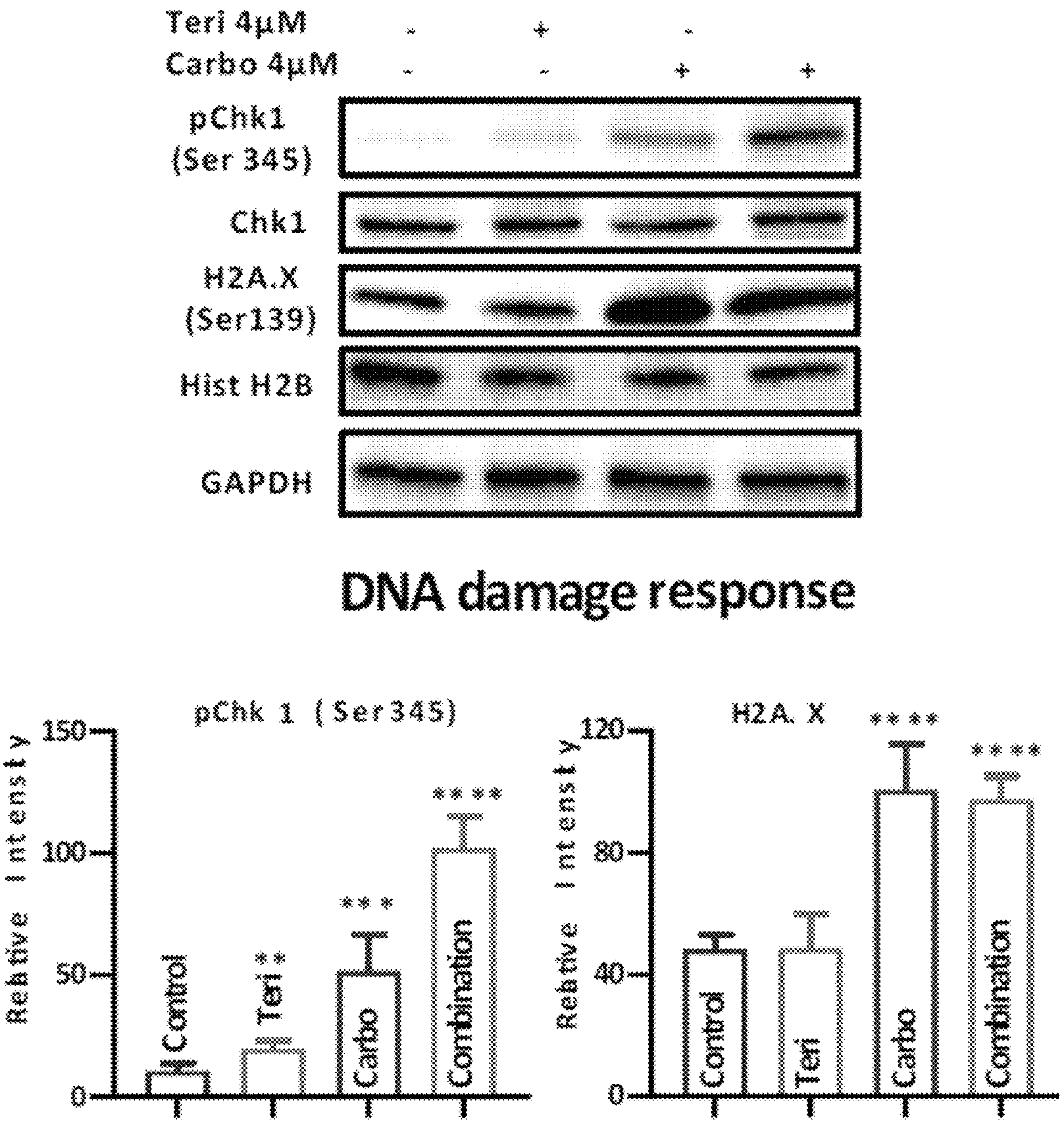
Figures 4D, 4E:
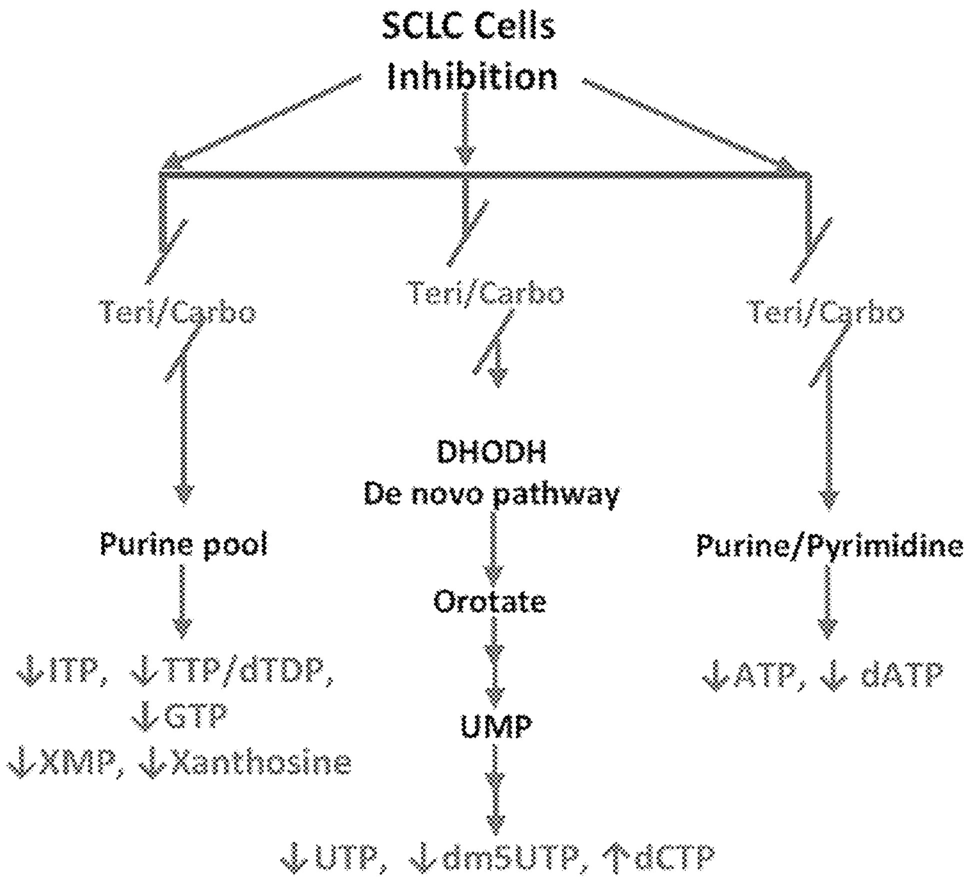
Figure 4F:
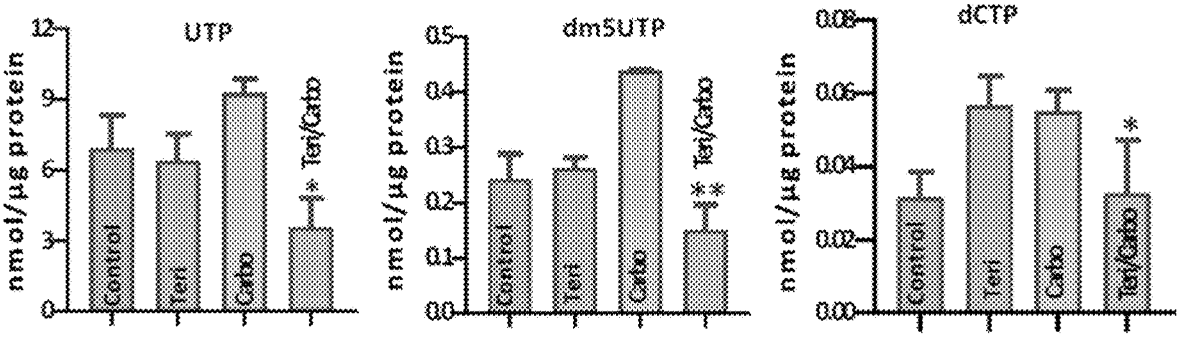
Figure 4G:
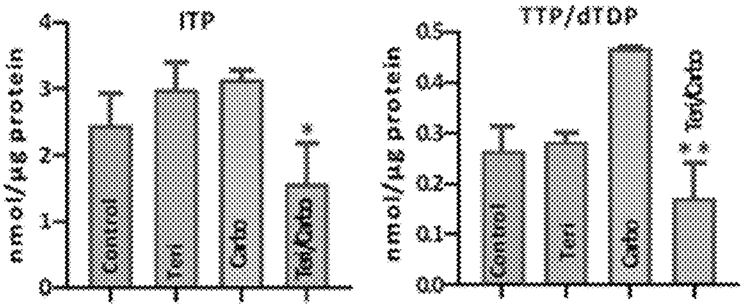
Figure 4G:
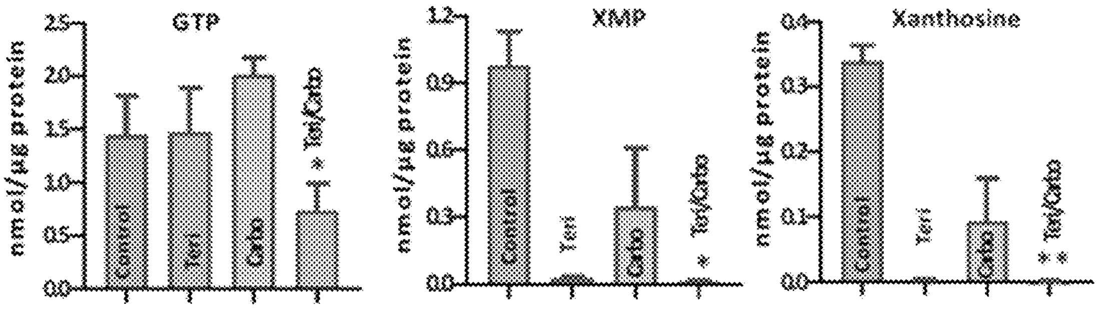
Figure 4H:
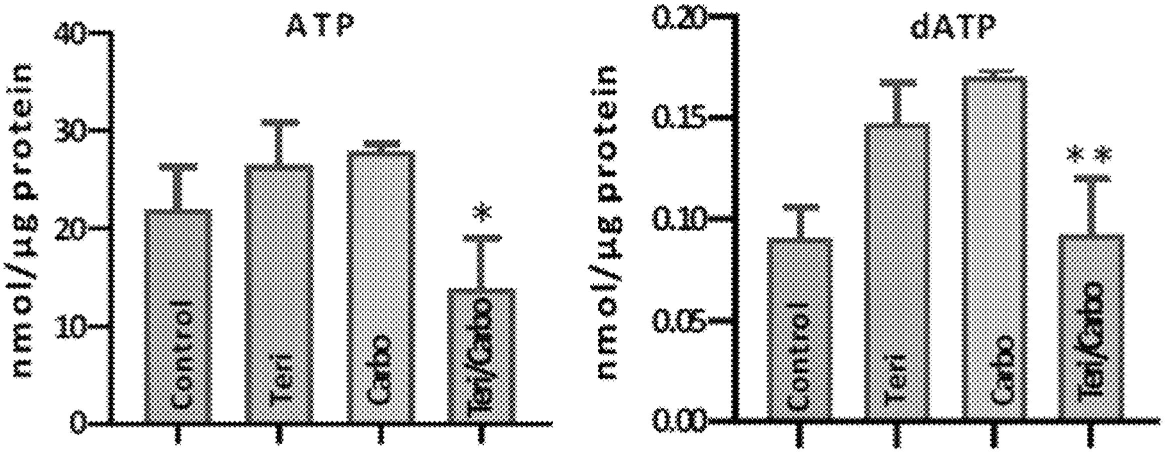

Alteration of p53 signaling is the most common genetic modification in SCLC (41). Several studies have shown that p53 phosphorylation is integral to cell apoptosis and accumulates in the mitochondria during cell death (42,43). p53 phosphorylation increased at $Ser^{15}$ in SBC3 cells when treated with Teri/Carbo (FIG. 4B). We detected high levels of DNA damage proteins (p-Chk1 and γ-H2AX) in Teri/Carbo-treated SBC3 cells (FIG. 4C). Teri/Carbo treatment of SBC3 cells regulated p53 phosphorylation, increased DNA damage, and dysregulated mitochondrial fission. Mitochondria are directly involved in the synthesis of intermediate cellular metabolites like purine and pyrimidine substances (40). DHODH, a mitochondrial inner membrane enzyme, catalyzes dihydroorotate to orotate. A recent study demonstrated a potential SCLC treatment to inhibit tumor growth in multiple in vivo models of SCLC by pharmacological inhibition of DHODH (35). Our experiments used Teri or Teri/Carbo for targeting DHODH in SBC3 cells. The schematic diagram shows the effect of Teri/Carbo on purine, pyrimidine, and purine/pyrimidine pools in SBC3 cells (FIG. 4D). To evaluate the synergism of Teri and Carbo on the concentrations of purines and pyrimidines, we used the mathematical model concentration=Treatment1+Treatment2+Treatment1*Treatment2. The significance of the effects was ascertained by p-values associated with the model's coefficients (20). Ten significant synergistic p-values were detected by this approach (FIG. 4E). Three pyrimidine substances were significantly inhibited with Teri/Carbo treatment. UTP concentration significantly decreased (control 6.95±0.96; Teri 6.42±0.79; Carbo 9.29±0.4; Teri/Carbo 3.6±0.82 nmol/μg protein) and dm5UTP (control 0.24±0.03; Teri 0.26±0.01; Carbo 0.44±0.001; Teri/Carbo 0.15±0.03 nmol/μg protein), dCTP was increased (control 0.03±0.005; Teri 0.06±0.01; Carbo 0.06±0.004; Teri/Carbo 0.03±0.01 nmol/μg protein) (FIG. 4F). Highest significant inhibitory effect of Teri/Carbo was observed for two purine substances XMP (control 0.98±0.11; Teri 0.03±0.005; Carbo 0.35±0.18; Teri/Carbo 0.01±0.002 nmol/μg protein) and xanthosine (control 0.339±0.017; Teri 0.003±0.0003; Carbo 0.094±0.045; Teri/Carbo 0.001±0.0002 nmol/μg protein) (FIG. 4G). Inhibition of DHODH with Teri/Carbo significantly depleted the ATP pool: ATP (control 22.01±2.98; Teri 26.55±2.96; Carbo 27.92±0.55; Teri/Carbo 13.87±3.61 nmol/μg protein) and dATP (control 0.09±0.01; Teri 0.15±0.01; Carbo 0.17±0.002; Teri/Carbo 0.09±0.02 nmol/μg protein) (FIG. 4H). Teri/Carbo treatment inhibited de novo pyrimidine synthesis of UTP in SBC3 cells, resulting in depleted ATP-dependent substance pools. Additionally, the drug combination reduced purine nucleotides XMP and xanthosine levels. Collectively, data from the combination treatment demonstrated that Teri/Carbo enhanced apoptosis, level of DNA damage, and disturbed purine/pyrimidine concentrations through two potential targets, DRP1 and DHODH.

Figure 4I:
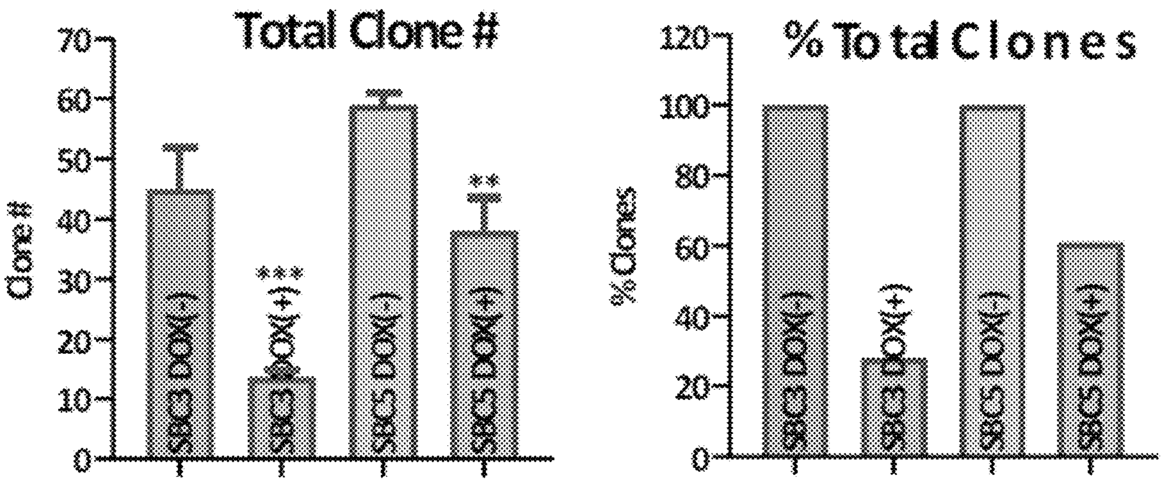

Effect of DRP1 CRISPR Knockout on Expression of Genes Associated with Mitochondria and Pyrimidines To further understand the role of DRP1 in SCLC, we performed the gene KO by CRISPR (see methods for CRISPR-Cas9). First, we tested the CRISPR KO efficiency at different time points, we found doxycycline (DOX) treatment for 72 and 96 h induced less than 5% gene editing outcomes in all cells. However, DOX treatment for 7 or 14 days can induce gene editing in SBC3 as 53.2% (Exon7)/31.6% (Exon8) with 7-day treatment and as 47.36% (Exon7)/31.56% (Exon8) with 14-day treatment, and in SBC5 as 37.4% (Exon7)/24.2% (Exon8) with 7-day treatment and as 35.2% (Exon7)/24.3% (Exon8) with 14-day treatment. The 7-day DOX (+) treated samples retained the highest mutation rate and slowest growth of SBC3 and SBC5 cells. Therefore, we selected the 7-day treatment samples to perform NanoString gene expression analysis, and the no-DOX (−) treated cells served as the negative control. The CRISPR/sgRNAs integrated SBC3 and SBC5 cells were sorted into single-cell clones. Finally, the single-sorted cells were cultured for an additional two weeks without DOX. After two weeks of culture, we noticed that DOX-treated cells had significantly reduced colony forming efficiency. DOX treatment reduced the number of colonies by 80% (SBC3) and 40% (SBC5) (FIG. 4I). Among the visible colonies, two types of growth patterns were apparent in the population: a normal growth pattern (as a negative control) and a significantly slow-growing population. We selected clones from both for PCR and subsequent sequencing to evaluate the relationship between CRISPR editing in the DRP1 CRISPR targeted region and growth rates. Slow-growing clones carry CRISPR-mediated mutations, while normal growing clones remained wild-type or only had one allele edited.

Figure 4J:
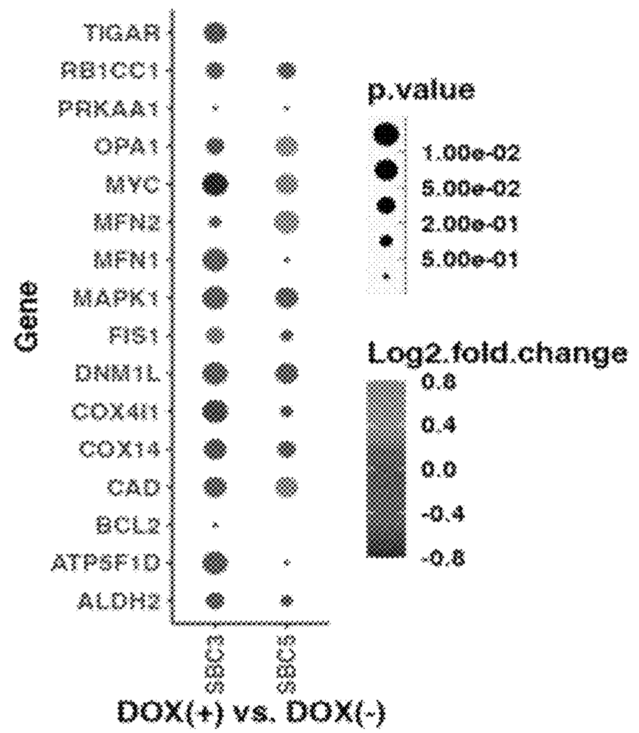
Figure 4K:
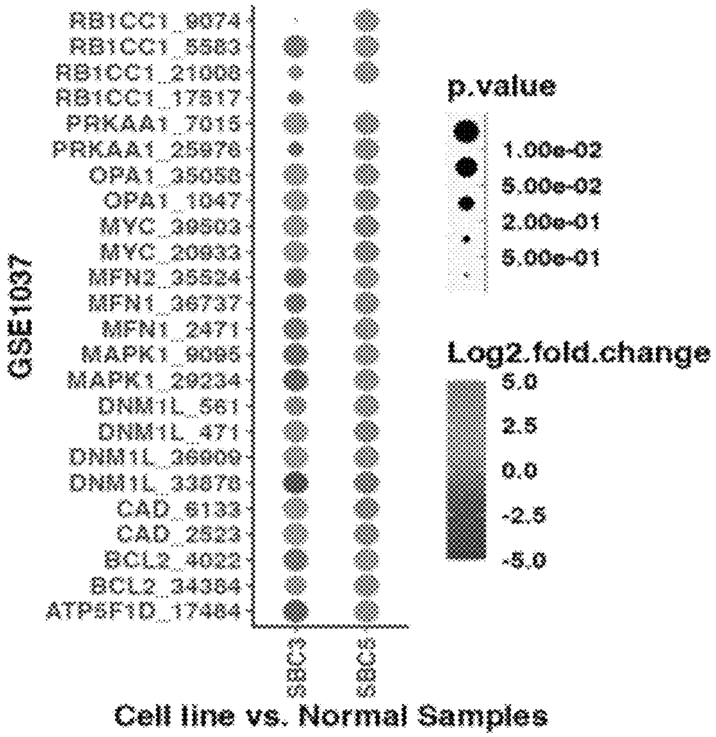

To further investigate the DRP1 function, we performed a NanoString assay to analyze the panel of genes associated with fission/fusion genes. Due to the scarce number of KO clones, the RNA samples were isolated and pooled as 10 clones per RNA samples for the assay. The NanoString analysis identified 16 differentially expressed genes in SBC3 and SBC5. FIG. 4J shows the different expression patterns for SBC3 and SBC5 (DOX+vs. DOX−). Several mitochondrial-related genes are down-regulated after the treatment. DNM1L is significantly decreased in both SBC3 and SBC5 after CRISPR KO. SBC3 has more down-regulated genes than SBC5, such as MYC, MFN1, MAPK1, COX411, CAD, and ATP5F. We also checked the expression pattern of those differentially expressed genes using in silico analysis with the public dataset GSE1037. GSE1037, based on GPL962 platform covered 11 of those genes we tested in the NanoString experiment. Expression of most of them is increased in SBC3 and SBC5 compared with normal samples. FIG. 4K shows the differential expression profile of SBC3 and SBC5. SBC5 shows a highly up-expression pattern. These results showed that DOX treatment significantly down-regulated mitochondrial-related genes. The up-regulation pattern was reduced after treatment in the sample with a highly up-regulation pattern (SBC5). In the case of the sample with moderate up-regulation (SBC3), the expression pattern was reversed after the treatment.

Teri/Leflu Increased the Efficacy of Lur In Vitro and In Vivo

Figure 5A:
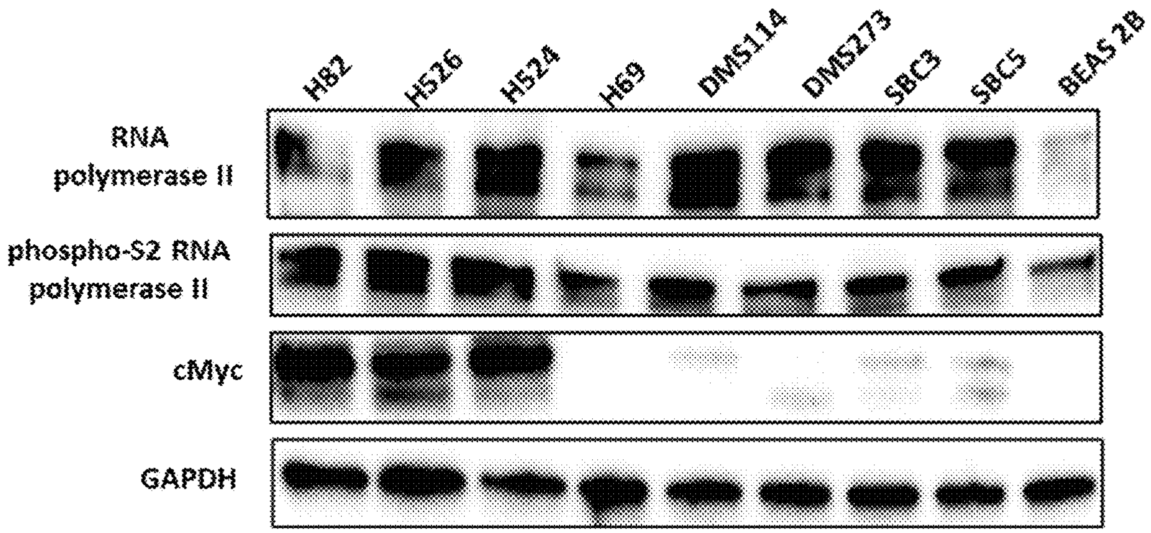
FIGS. 5A-5B. Representative immunoblots of the expression of RNA polymerase II and phospho-in SCLC cell lines and non-malignant BEAS 2B cells (n=3). Five SCLC cell lines were treated with difference concentrations of Teri and Lur for 72 hours. Cell viability was detected by CCK-8 assay.
Figure 5B:
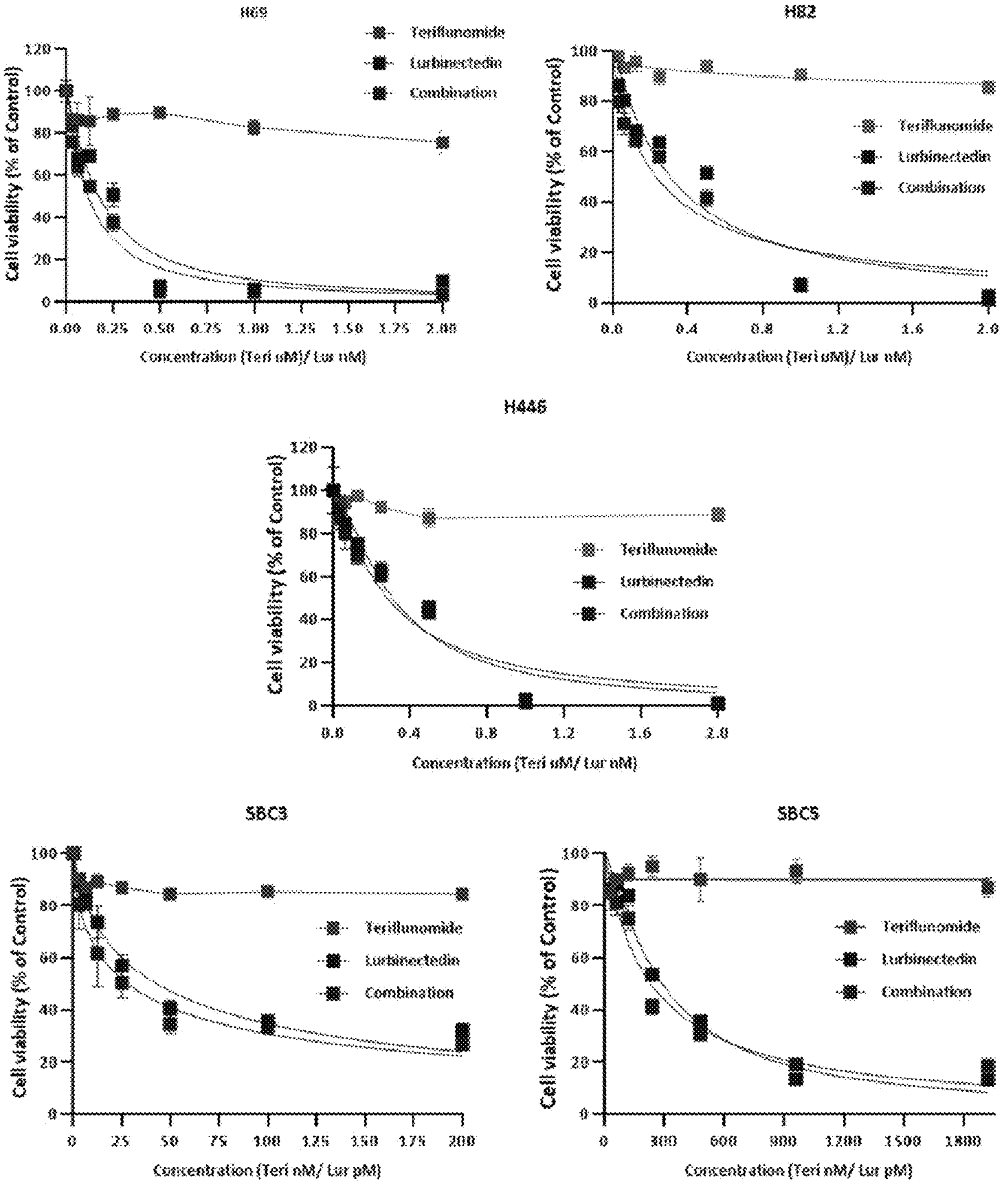

Among the drugs approved for SCLC, lurbinectedin is used to treat patients with metastatic SCLC with disease progression. Lurbinectedin (Lur) is an inhibitor of RNA polymerase II, which is commonly hyperactivated in SCLC, resulting in excessive transcription in tumor cells (44). In this study, we tested the combination of Lur with Teri to see if it may reduce the viability of SCLC cells. RNA polymerase II expression and phosphorylation were increased in SCLC cell lines compared with non-malignant BEAS 2B cells (FIG. 5A). We evaluated the synergistic effects of Teri and Lur in a panel of SCLC cell lines. The cell viability assay did not show any synergistic effects for Teri/Lur. However, low doses of Lur drastically increased cell cytotoxicity in H69, H82, H446, SBC3, and SBC5 cells (FIG. 5B).

Figure 6A:
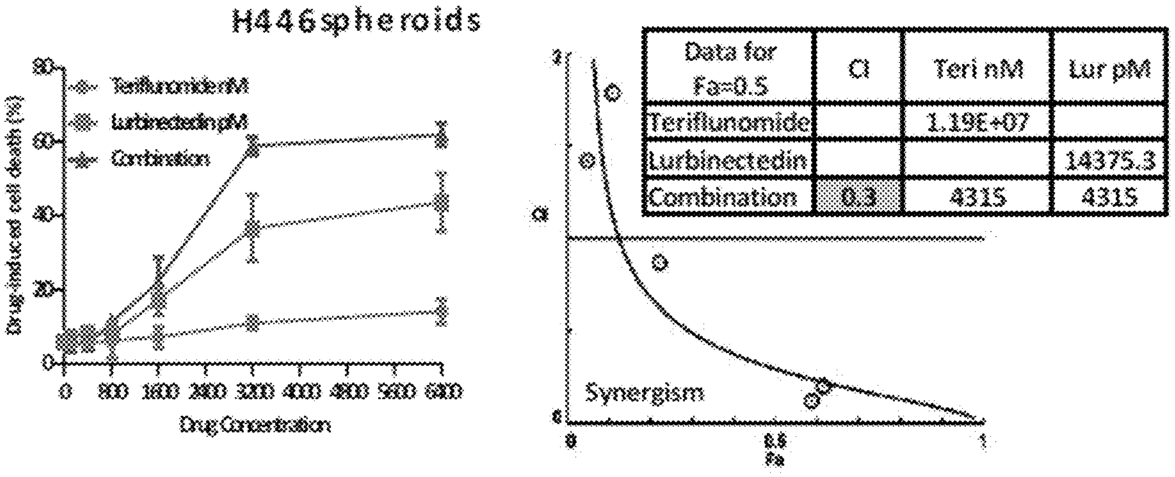
FIGS. 6A-6M. Spheroid response for drug treatments.
Figure 6B:
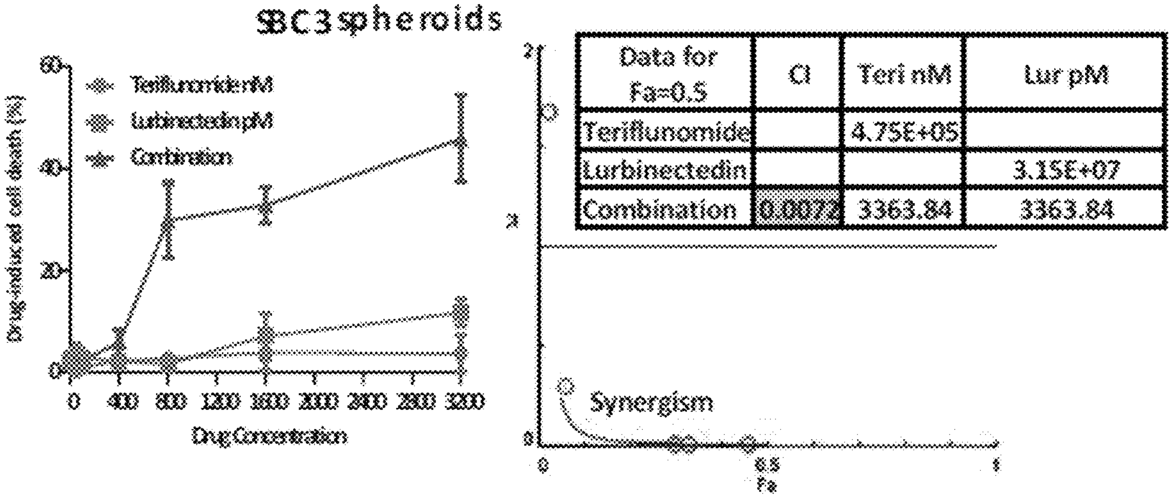
Figure 6C:
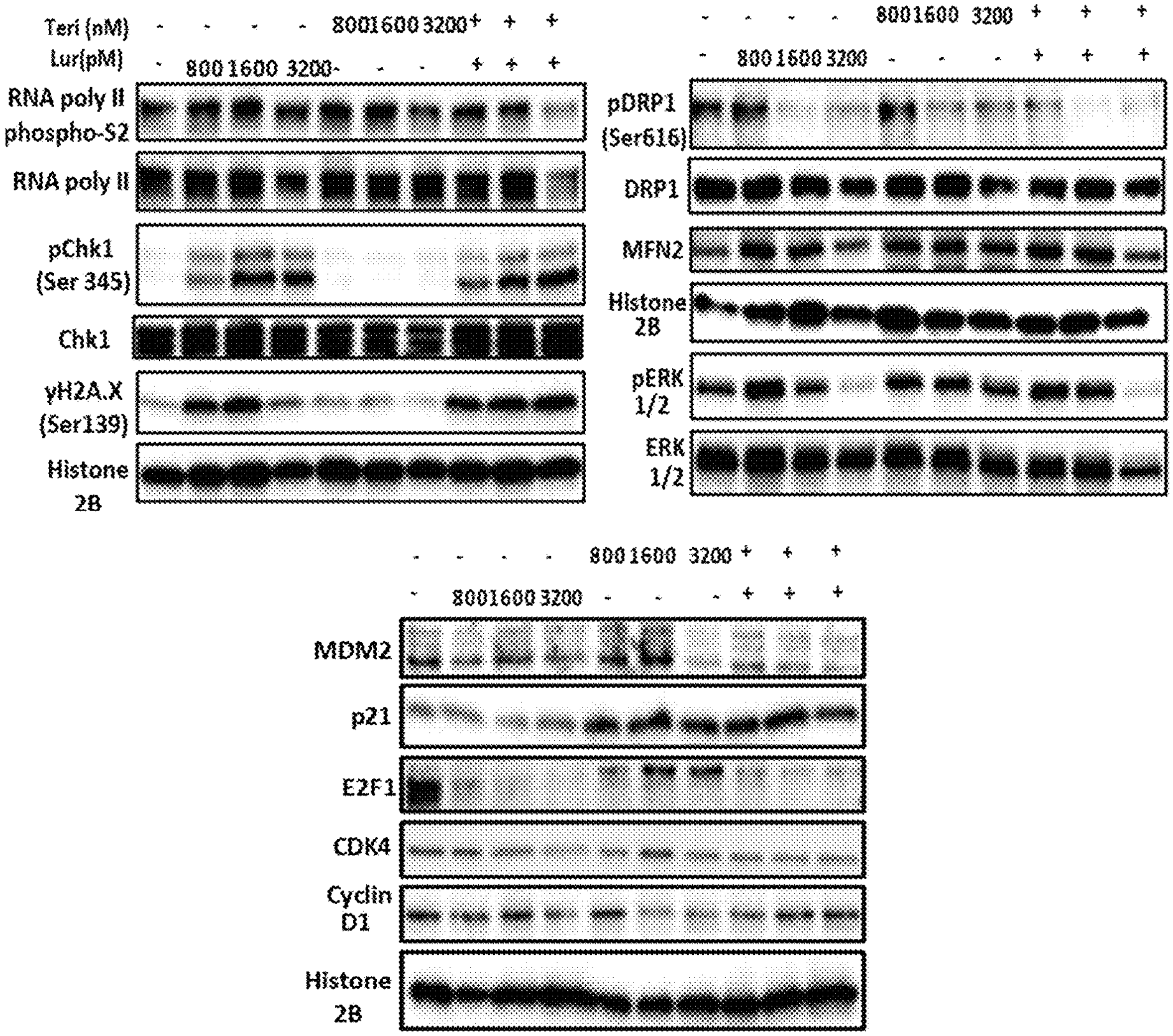
Figure 6D:
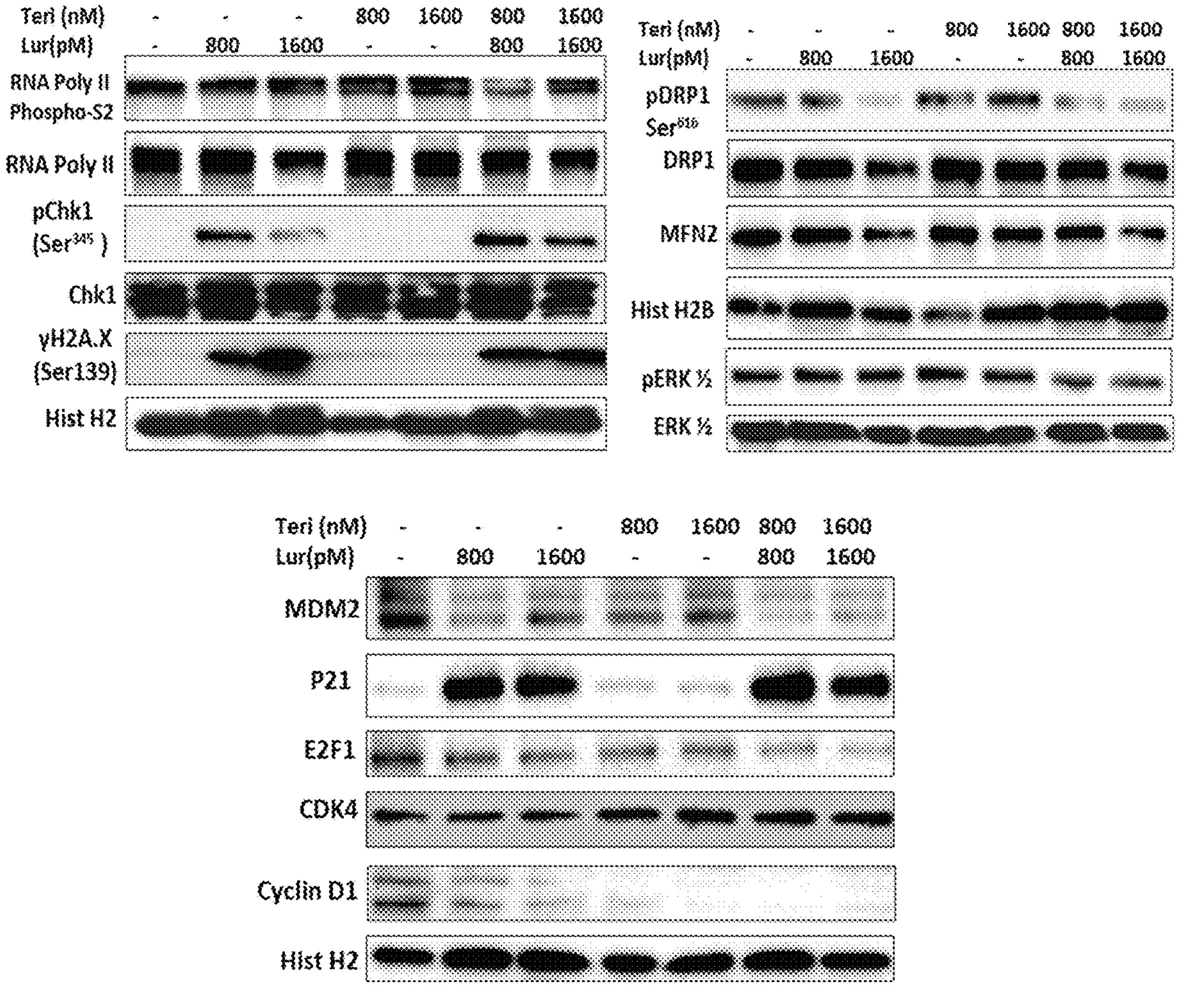
Figure 6E:
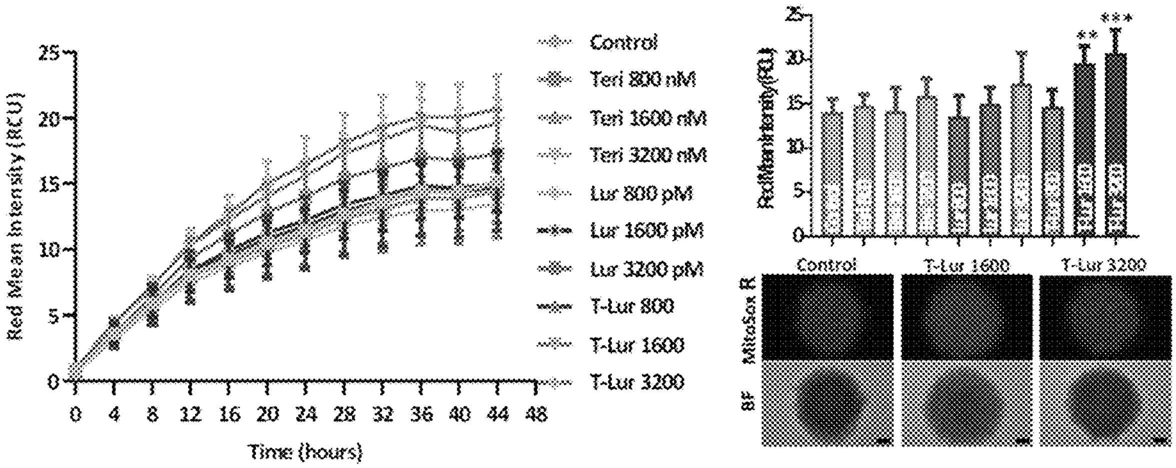
Figure 6F:
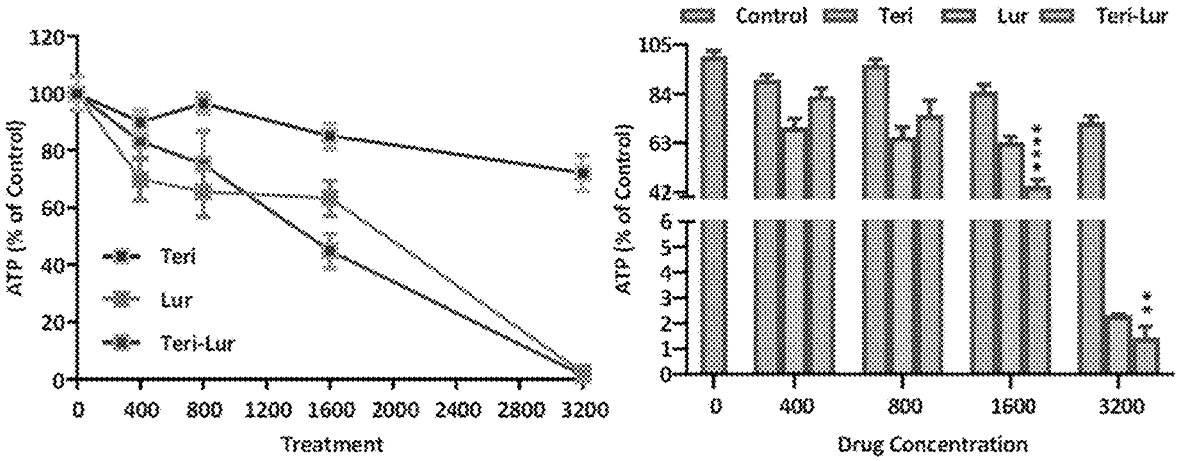
Figure 6G:
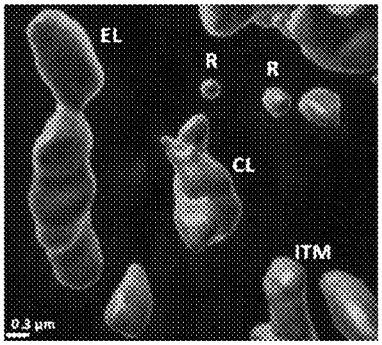
Figure 6H:
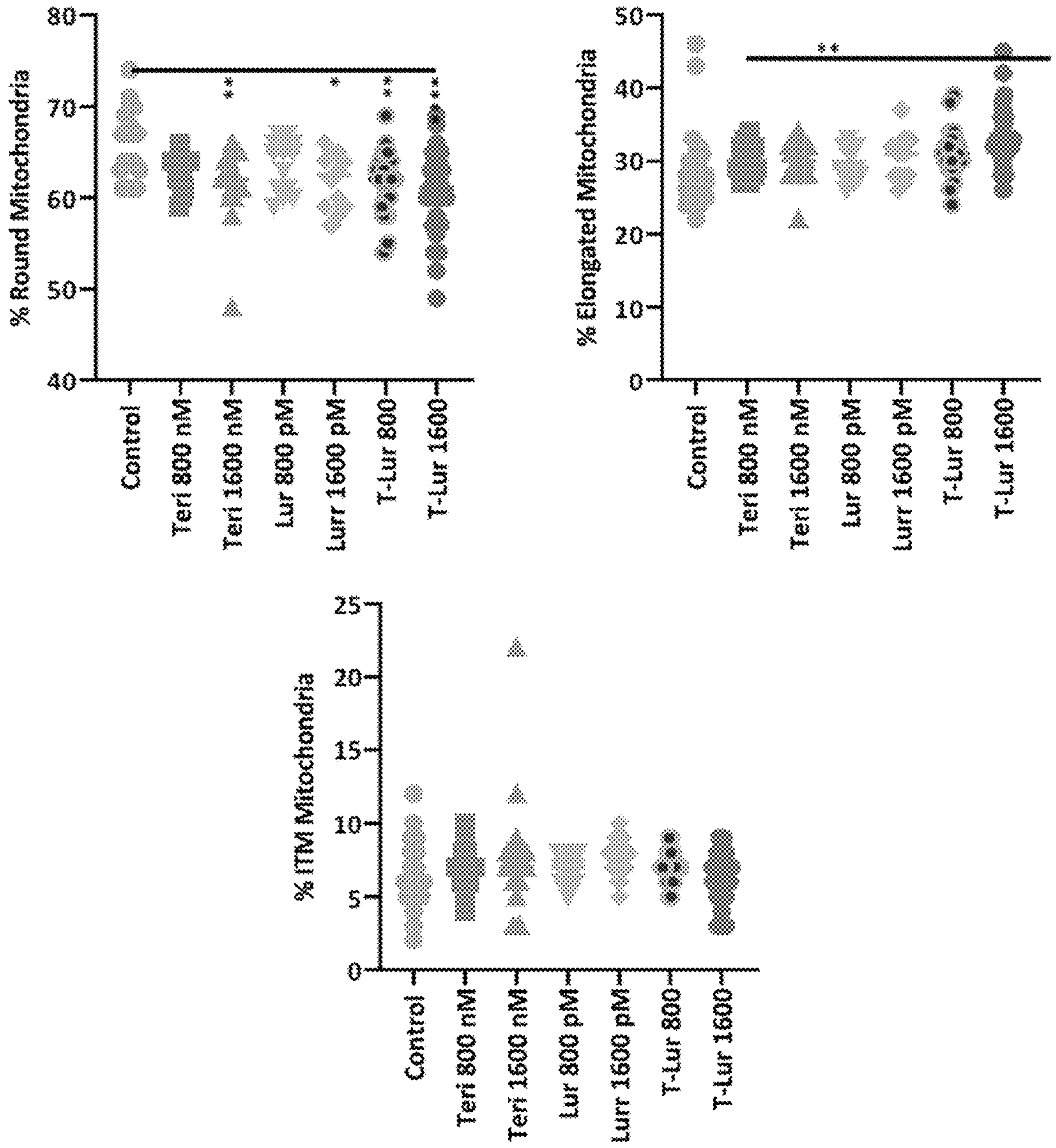

We used spheroid cultures as a second model to validate the synergistic effect of Teri/Lur treatment on SCLC cell viability and apoptosis. In addition, we used an LDH cytotoxicity assay to monitor therapeutic efficacy for 3D culture systems, to find the synergy of Teri with Lur. Treatment of H446 spheroids with Lur or Teri/Lur significantly increased the percentage of dead cells in a dose-dependent manner (FIG. 6A, left panel). The CI was calculated using the Chou-Talalay method. Notably, we observed a synergism with fixed concentrations of Teri and Lur. The $IC_{50}$ values for combination treatment was 4315 nM Teri/4315 μM Lur three-fold lower than single treatment. The value of $CI_{50}$=0.3 indicates drug synergism of Teri/Lur (FIG. 6A, right panel). SBC3 spheroids are more sensitive for Teri/Lur combination and responded synergistically with $CI_{50}$ value 0.0072 (FIG. 6B). Moreover, to further study spheroids sensitivity to Teri/Lur we evaluated the apoptosis, mitochondrial dynamics proteins, and cell cycle in 3D. Teri/Lur combination inhibited RNA poly II activity and increased the level of DNA damage and of replication stress proteins like γH2AX and pChk1(Ser345) (FIG. 6C, left panel). Next, we tested the effect of Teri and Lur on mitochondrial dynamics and checked the expression of DRP1 and MFN2 in H446 spheroids. The dose-dependent inhibition of DRP1 phosphorylation at Ser616 with Teri (1600 and 3200 nM) was comparable with our observation in 2D culture. Interestingly, Lur-mediated reduction in DRP1 phosphorylation correlated with decreased ERK phosphorylation, indicating the inhibition upstream of ERK but there was no change in MFN2 level. Inhibition of pDRP1 was increased with Teri/Lur combination (FIG. 6C, right panel). Antiproliferative effect of Teri is related with cell arrest in G1/S cell cycle control (30). We investigated Teri/Lur effect on spheroid cell cycle after drug treatment. FIG. 6C (lower panel) shows the expression of MDM2, p21, and E2F1, the regulators of p53 and cell cycle cyclins in H446 spheroids. MDM2 and E2F1 were downregulated with Teri/Lur combination. Cell cycle arrest protein p21 was strongly elevated with Teri and Teri/Lur treatments. As well, cyclin-dependent kinase CDK4 was inactivated with Lur or Teri/Lur treatments and did not affect the level of cyclin D1. Teri/Lur treatment was more potent on SBC3 spheroids and worked with lower concentrations (800 and 1600 nM/pM). Teri/Lur combination slightly reduced the phosphorylation level of RNA poly II (FIG. 6D, left panel). The same trend in response to DNA damage was observed in SBC3 spheroid model. Phosphorylation level of histone and Chk1 was increased. Similarly, to Teri/Lur treatment of H446 spheroids, pDRP1 level was reduced, and a moderate decrease of ERK phosphorylation was observed after treatment (FIG. 6D, right panel). Histone 2B served as a loading control for SCLC spheroids. Additionally, SBC3 spheroids were analyzed for cell cycle proteins. Teri/Lur treatment inhibited the expression of MDM2 and E2F1. Both Lur and Teri/Lur treatments upregulated p21 level. Activation of p21 inhibited cyclin D1 (FIG. 6D, lower panel). Finally, our results demonstrated Teri/Lur inhibitory effect on the cell cycle with decreasing H446 and SBC3 spheroid cells passing through G1 into S thus blocking DNA replication and leading to diminished spheroid growth. Next, mitochondrial dysfunction was evaluated in H446 spheroids by measurement of mitochondrial superoxide. The superoxide levels were unaffected with Teri or Lur treatment. A significant increase was observed after 40 h of Teri/Lur treatment (FIG. 6E, left panel). Two dose groups of Teri/Lur (1600 and 3200 nM/pM) led to an elevation in the mitochondrial ROS measured by MitoSOX intensity in H446 spheroids (FIG. 6E, right panel). ATP measurement was used to test the effect of Teri and Lur on spheroid cytotoxicity and cell death; the ATP level of treated spheroids was normalized to control. The concentration of Teri/Lur (1600 nM/pM) significantly decreased the level of ATP in spheroids to 50% compared with the control. Single-drug treatment with the same concentration of Teri or Lur reduced ATP levels to approximately 80% and 60%, respectively. There is also a significant difference in ATP levels between Lur (1600 μM) and Teri/Lur (1600 nM/pM) (FIG. 6F). Z-stacks of H446 spheroids stained with MitoTracker red were acquired on a Zeiss LSM 880 in Airyscan Fast mode. 2D subset images were analyzed in Imaris to evaluate the effect of Teri/Lur on mitochondrial morphology (FIG. 6G). Bounding Box 00 Lengths were generated from Surface detections of individual mitochondria and categorized into three groups: round, elongated and intermediate. Percentages of round/fragmentated mitochondria significantly decreased with Teri (1600 nM) or Lur (1600 μM), and two Teri/Lur doses (800, 1600 nM/pM). The percentage of elongated mitochondria significantly increased only with 1600 nM/pM Teri/Lur treatment. Percentage of ITM mitochondria was unaffected (FIG. 6H).

Figure 6I:
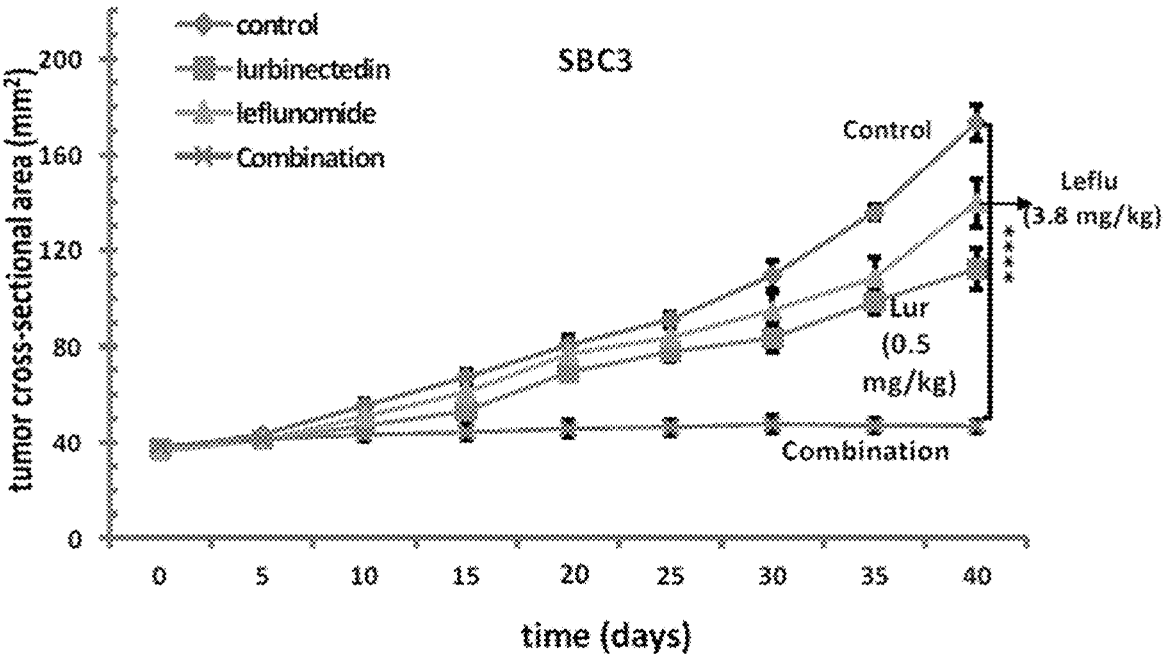
Figure 6J:
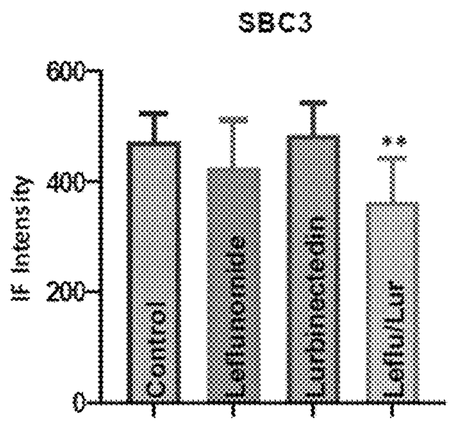
Figure 6K:
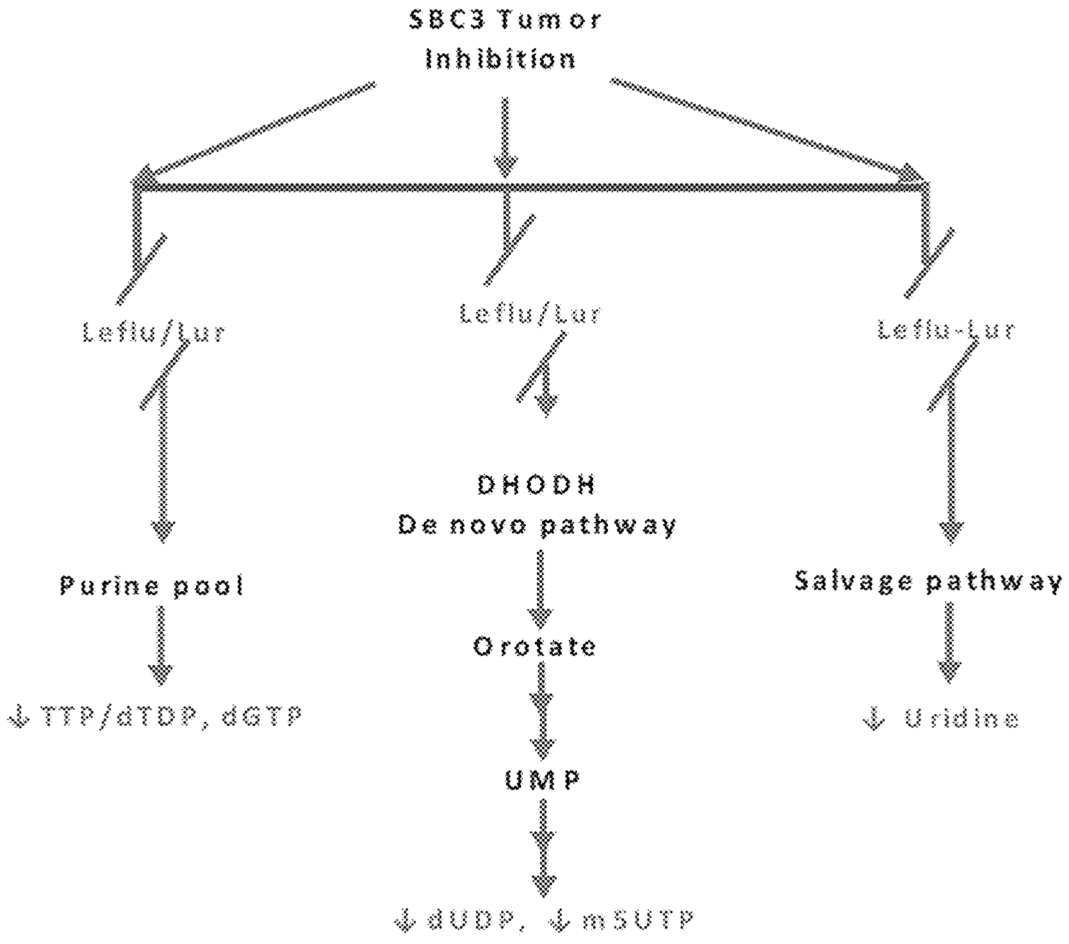
Figure 6L:
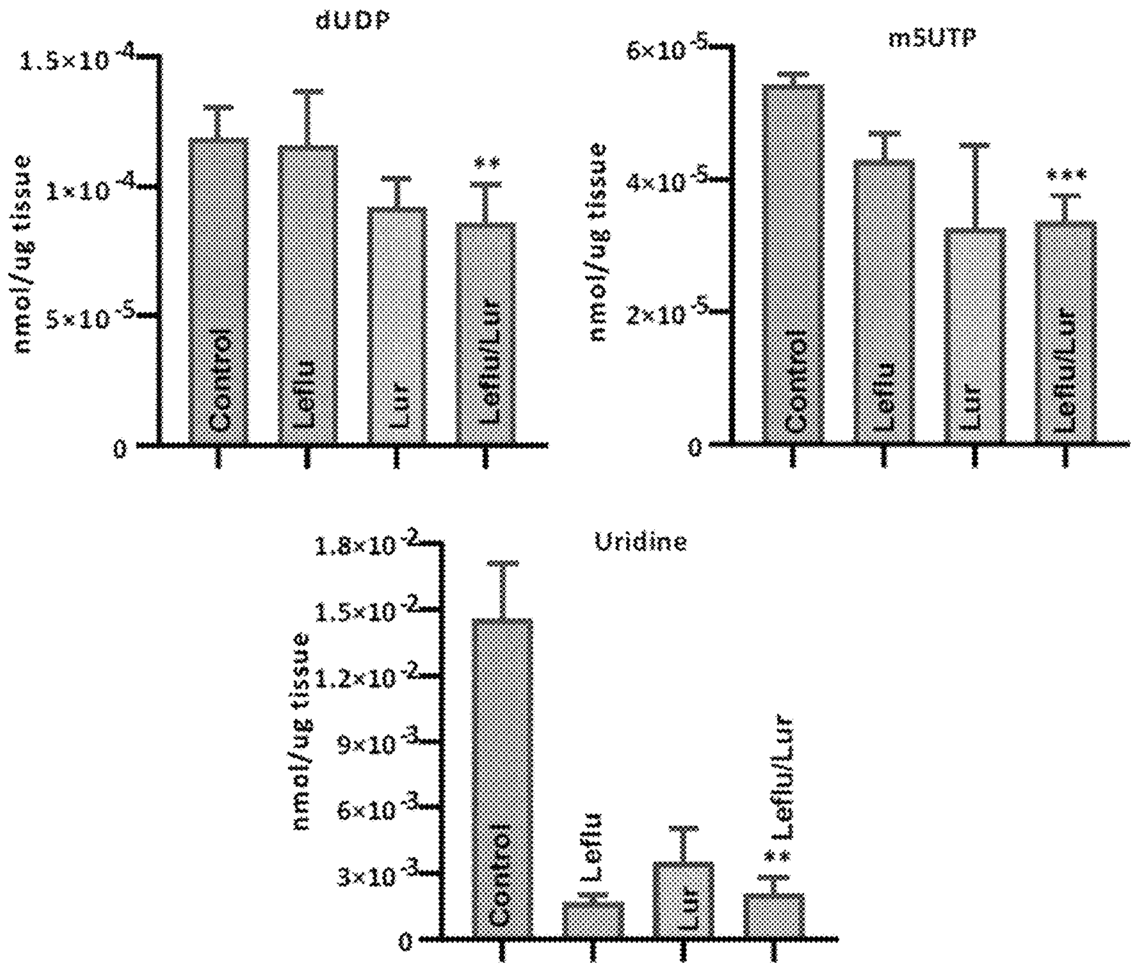
Figure 6M:
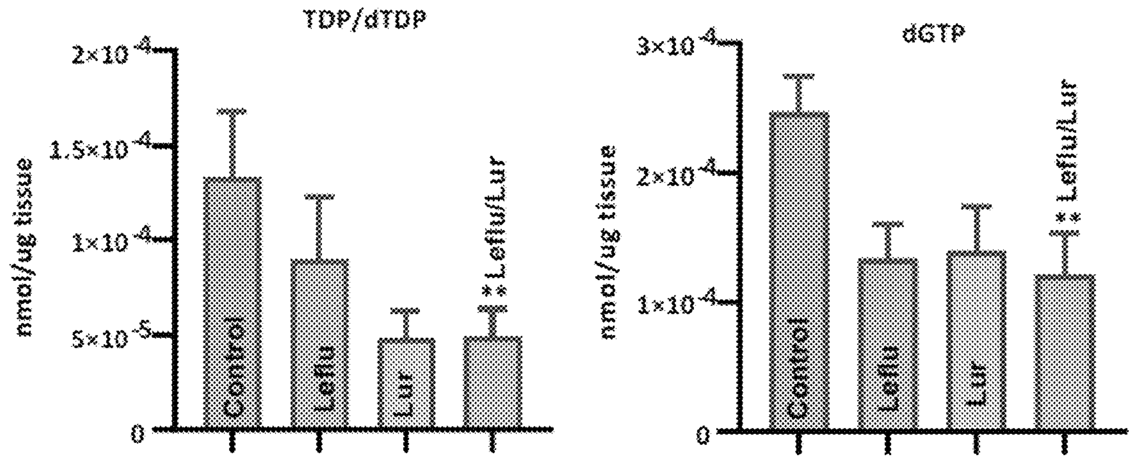

Finally, the efficacy of Teri/Lur was tested in a second SBC3 mouse xenograft model. Both Leflu and Lur alone, as well as Leflu/Lur combination significantly reduced tumor growth over time compared to the control: control—1.78±0.14 g; vs. treated: Lur—1.09±0.11 g, Leflu—1.39±0.12 g, and Lur/Leflu—0.28±0.04 g (FIG. 6I). Tumor sizes were reduced with Lur (~39%) and Leflu (~22%) treatments. From the rate of regression in xenograft studies, Leflu/Lur was more effective than either drug alone. A much greater reduction in tumor weight was observed in combination treatment (~84%). Leflu/Lur blocked tumor growth and caused inhibition of DRP1 phosphorylation at Ser616 (FIGS. 6I-6J). Leflu or Leflu/Lur suppresses tumor growth by inhibiting DRP1 and interrupting the pyrimidine pathway. We next evaluated the purine and pyrimidine substances in tumor tissue of the control and treated groups. Inhibition of tumor growth can be regulated by interrupting active purine or pyrimidine pools. The schematic diagram shows the effect of Leflu/Lur on purine and pyrimidine pools in SBC3 mouse xenograft (FIG. 6K). The same mathematical model from Teri/Carbo analysis was used to evaluate the synergism of Leflu and Lur on the concentrations of purines and pyrimidines. Leflu/Lur synergistically affected only one pyrimidine base, uridine, that is generated by the salvage pathway. dUDP and m5UTM levels, two substances from the de novo pyrimidine pathway, were significantly lower than the control (FIG. 6L). Leflu/Lur treatment strongly reduced concentrations of purine TDP/dTDP and dGTP substances (FIG. 6M). Together, these results confirm the therapeutic efficacy of Lur in combination with Teri or Leflu in SCLC preclinical models. Combined drug treatment of spheroids was more effective than a single drug treatment. It induced a robust increase in cellular damage and cytotoxicity while affecting mitochondrial morphology due to DRP1 inhibition and inhibited the pyrimidine salvage pathway in mouse xenograft.

RNAseq Analysis of Potent Activity of Teri/Lur in SBC3 a Spheroid-Model

Figure 7A:
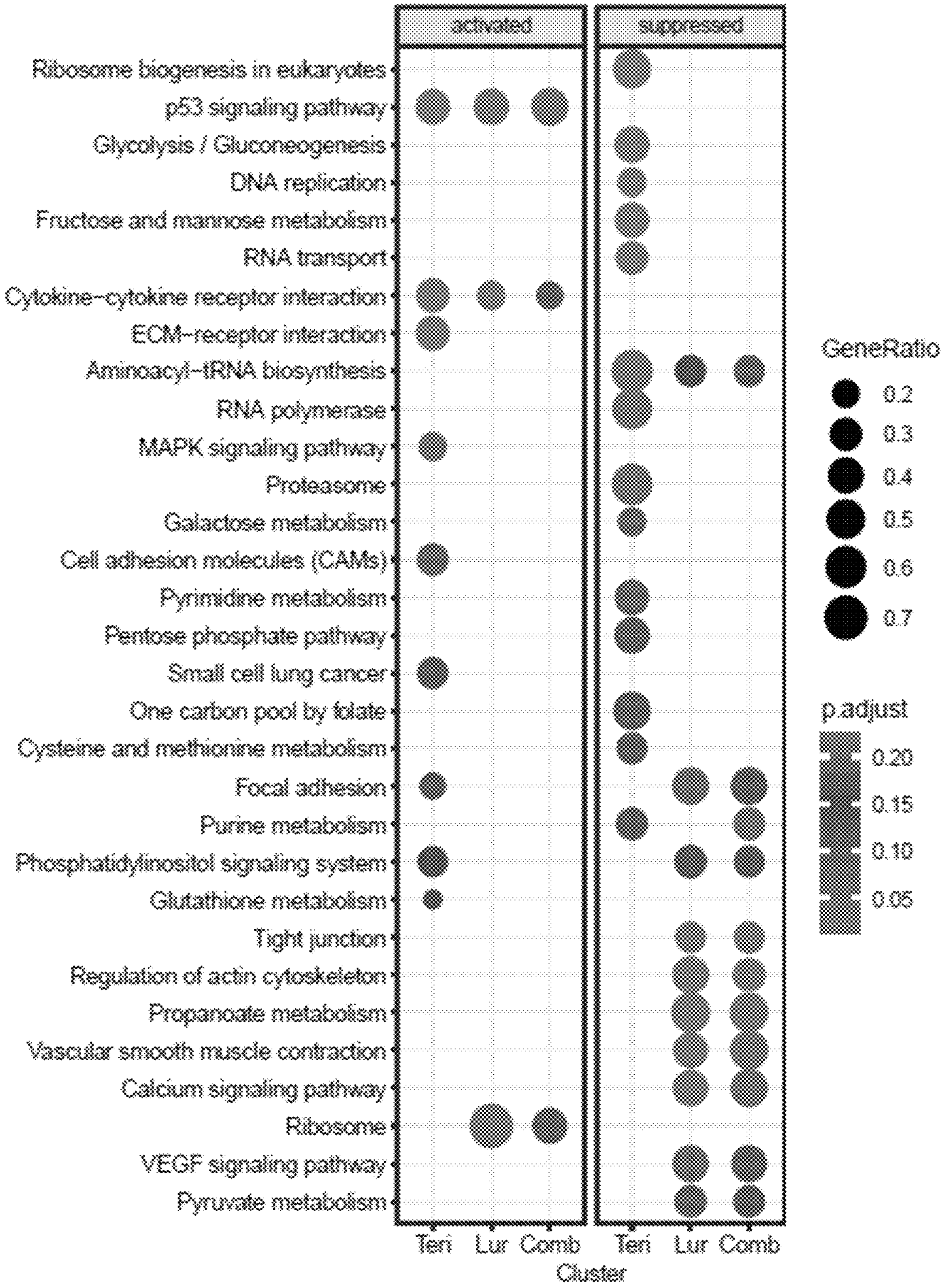
FIGS. 7A-7C. RNA-seq based gene expression profiles in response to different treatment.
Figure 7B:
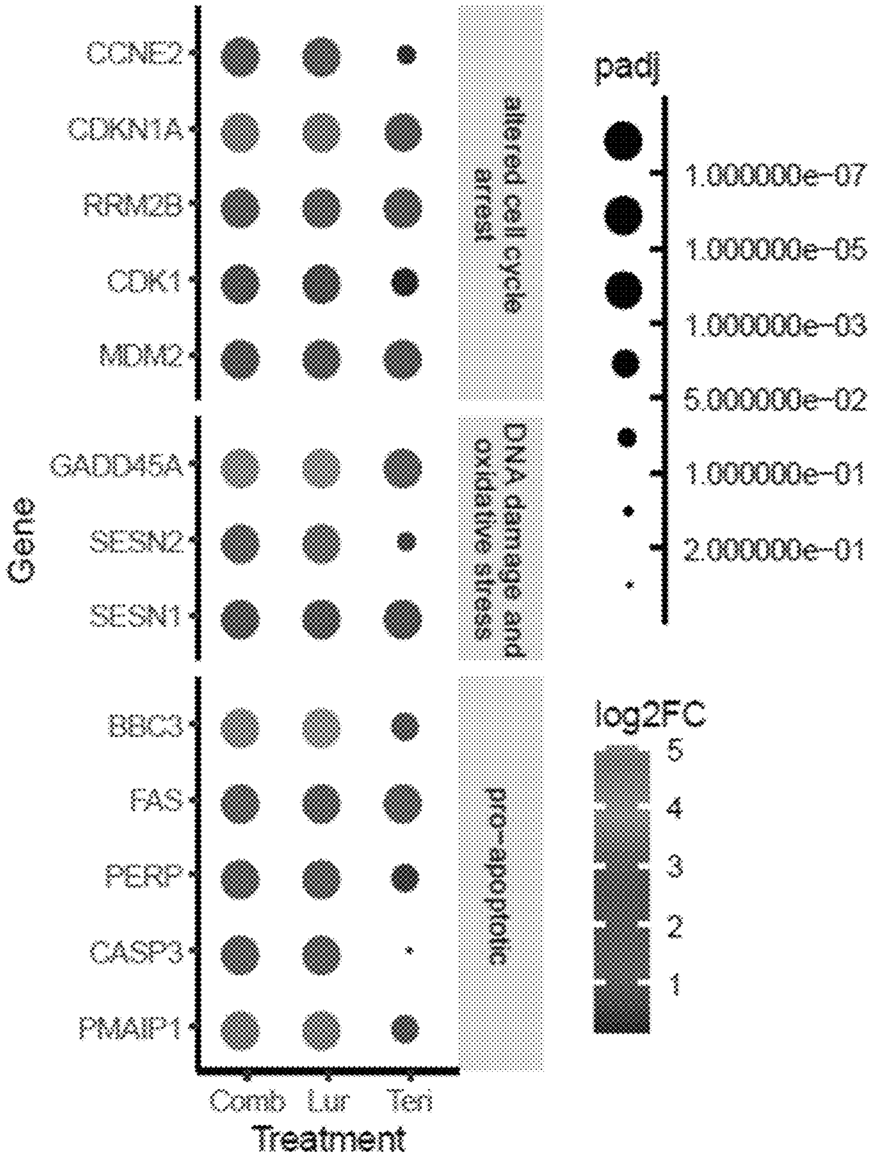

Next, we employed RNA sequencing to identify significant genes and pathways that were affected by Teri, Lur alone or the drug combination in SBC3 spheroids at 24 h. Results showed a unique gene expression profile for each treatment. The total number of genes was almost ten times higher with Lur and Teri/Lur treatment than with Teri treatment (Lur—8724 genes, Teri/Lur—8098 genes, and Teri—832 genes). Genes significantly affected by drug treatment were grouped by gene enrichment analysis (GSEA) for KEGG pathways. Results demonstrated the regulation of multiple signaling pathways. The p53 signaling pathway was activated in each group of drug treatment. Excess activation of p53 induces cellular stress, including DNA damage, cell cycle arrest, and apoptosis (FIG. 7A). The percentage of altered genes of p53 signaling pathway was 34% for Teri, 38% Lur and 43% Teri/Lur. Teri treatment upregulated additional pathways such as metabolic processes (MAPK signaling pathway, phosphatidylinositol signaling system, glutathione metabolism) and cellular communication (ECM-receptor interaction, small cell lung cancer, and cell adhesion molecules) (FIG. 7A). All drug-treated groups activated cytokine-cytokine receptor interaction; additionally, Lur and combination treatment promoted ribosome signaling. Next, we investigated the downregulation effects of Teri, Lur, and combination treatments on signaling pathways. Aminoacyl-tRNA biosynthesis, responsible for protein synthesis and involved in tumorigenesis (45), was suppressed by Teri, Lur, and Teri/Lur treatment (FIG. 7A). Teri alone displayed robust metabolic effect and downregulated ribosome biogenesis in eukaryotes, glycolysis/gluconeogenesis, fructose/mannose and galactose metabolism, pyrimidine and purine metabolism, pentose phosphate pathway and cysteine/methionine metabolism (FIG. 7A). In addition, Lur and combination treatment suppressed two other metabolic pathways, propanoate and pyruvate metabolism, and could contribute to inhibition of disseminating metastatic cells (46,47). Lur alone or combination treatment negatively impacted cell interaction in SBC3 spheroids through inhibition of focal adhesion, tight junction, actin cytoskeleton and calcium signaling pathways (FIG. 7A). Two other tumor angiogenesis driver pathways, VEGF and vascular smooth muscle contraction, were also suppressed by Lur and combination treatments. We performed functional enrichment analyses to detect top genes that regulate key signaling pathways after Teri, Lur, and Teri/Lur treatment. In p53 signaling pathway, Teri, Lur, and Teri/Lur combination altered cell cycle arrest genes (MDM2, CDK1, RRM2B, CDKN1A, CCNE2), DNA damage and oxidative stress genes (SESN1, SESN2, GADD45A), and pro-apoptotic genes (PMAIP1, CASP3, PERP, FAS, BBC3) (FIG. 7B). GSEA detected up-regulated genes related/critical to the p53 signaling pathway after Teri, Lur, and Teri/Lur treatments. Teri treatment caused DHODH inhibition, constraining the biogenesis of ribosomes and activating the p53 pathway (48) leading to cycle arrest.

Figure 7C:
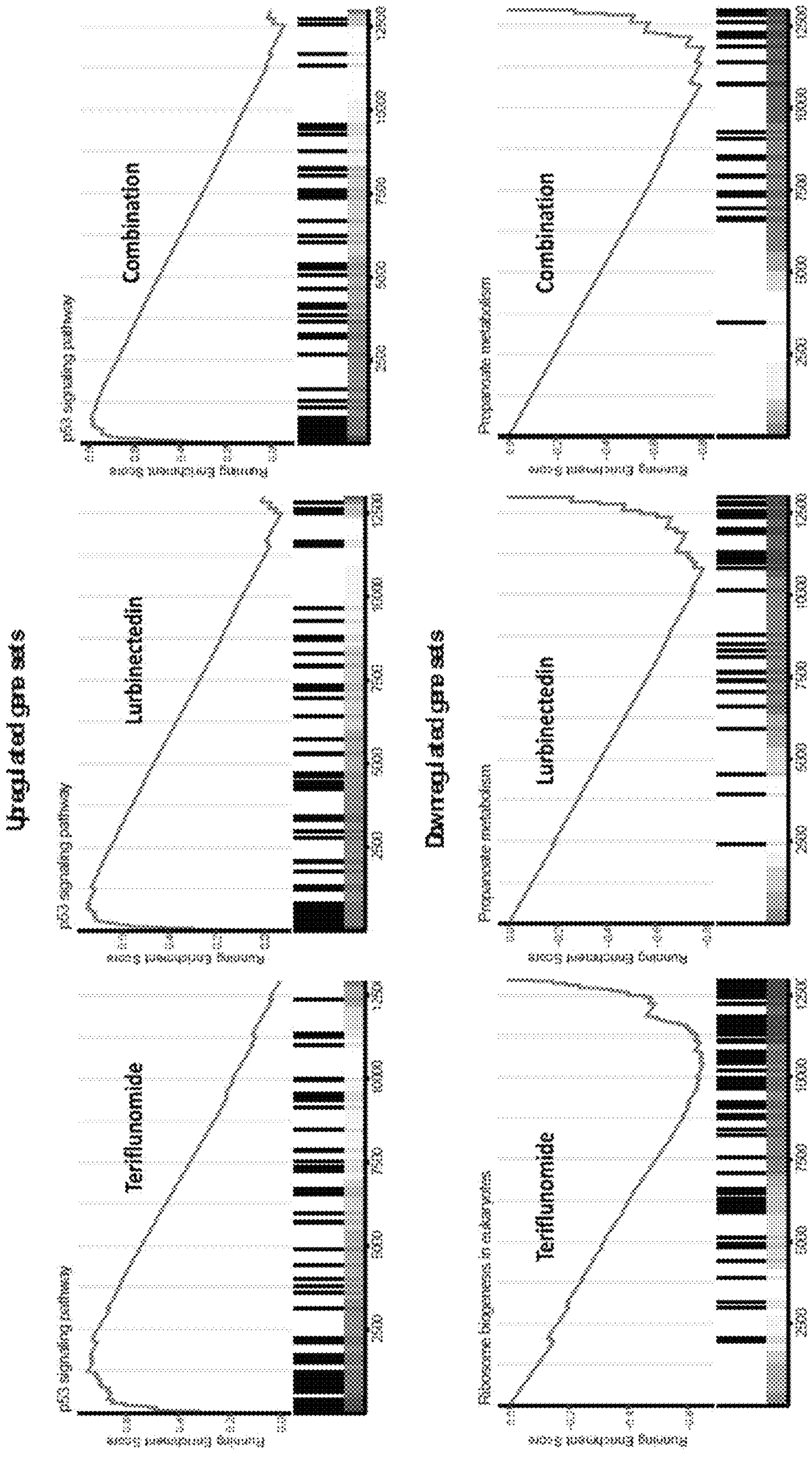

Furthermore, the combination treatment GSEA plot indicated that Teri sensitized SCLC spheroids to Lur and mediated apoptosis by activating the p53 signaling pathway (FIGS. 7A and 7C). These metabolic changes could impair mitochondrial oxidation and morphology. RNA-seq results indicated the robust/substantial effect of Teri/Lur combination treatment on critical cancer pathways in an SBC3 spheroid model. Using a low concentration range of Teri and Lur for 24 h, combination treatment increased cellular cytotoxicity and elevated cell cycle arrest, apoptosis, and DNA damage, suppressed cell-cell interactions, and cellular metabolism. Functional enrichment analysis of RNA-seq data yielded potential key targets critical to understanding molecular mechanisms of Teri/Lur in SCLC.

Abnormal expression of DRP1, observed in different tumor types, affects cancer progression through cell proliferation, mitochondrial dynamics, cell apoptosis, and cell cycle regulation (7,49,50). A recent study showed that mRNA DRP1 level increased two-fold in SCLC tissue compared with control and reported a correlation between high expression of DRP1 with poor survival probability for males and females (50). Pharmacological inhibition of DRP1 activity promoted cell cycle arrest and apoptosis in lung cancer cells (49). Increasing evidence suggests that targeting DRP1 to suppress mitochondrial fission may be a new strategy to treat SCLC.

Teri and Leflu are FDA-approved drugs with immunomodulator and immunosuppressant effects and affect mitochondrial morphology through inhibition of DHODH and MFN2 activation (9,10). Our molecular modeling analysis of DRP1 interaction with Leflu and Teri showed the highest binding score for Teri; Leflu had less interaction, and MDIVI1 showed the lowest binding score with DRP1. MDIVI1 is a putative inhibitor of mitochondrial fission and GTPase activity of DRP1 and induces mitochondrial elongation in cells (49). MDIVI1 caused apoptosis and enhanced chemotherapy-induced apoptosis in several cancer cells (51). The effect of MDIVI1 on DRP1 in our study was present but lower when compared with Teri and Leflu. Several studies showed that Leflu inhibited cancer cell proliferation through distinct mechanisms which distressed the mitochondrial network, cell cycle, purine and pyrimidine synthesis, c-Myc signaling, and metabolism (50,52,53).

Mitochondria play an important role in tumor growth and changes in mitochondrial shape has been shown to influence its function (7,49). The mitochondrial fusion/fission cycle is not a randomly occurring event and is regulated by a shared environment, communication, group formation, synchronization of behavior, and contact with other organelles (54,55). $Ser^{6161637}$, DRP1 phosphorylation sites, are directly involved in DRP1 activation and mitochondrial morphology regulation (7). After Teri treatment, there was a significant decrease of DRP1 phosphorylation at $Ser^{616}$ and reduced $pDRP1^{Ser616/637}$ ratios in dose-dependent manner in SBC3 cells. Additionally, Teri treatment was associated with mitochondrial area increase and correlated with mitochondrial elongation. Teri treatment shifted the balance from fission to fusion in SBC3 and SBC5 cells and decreased mitochondrial fragmentation and cell proliferation. The DRP1/MFN2 ratio is increased in lung cancer patient tumor tissue, and DRP1 knockdown or inhibition blocks cell cycle progression in lung cancer cells (49). Furthermore, initiation of mitochondrial fusion through pharmacological or genetic manipulations, reduced tumor growth (10). We found that Teri/Carbo enhanced chemotherapy-induced cell cytotoxicity and apoptosis in SBC3 and SBC5 cells. The malignant phenotype of fragmented mitochondria is a mitochondrial dynamic response to specific stressors to maintain the functions of rapidly proliferative cells. Recent studies reported that mitochondria contribute to cell's chemotherapeutic drug resistance by adjusting their shape toward fragmentation and creating mitochondrial dynamic imbalance (11,32,56). Since Teri directly targeted DRP1, we observed the inhibition of phosphorylation at $Ser^{616}$ after Teri/Carbo treatment. Furthermore, combination treatment increased cleaved PARP and p-p53 levels, and DNA damage proteins p-Chk1 and γ-H2AX. It is known that p53 accumulation in the mitochondria can induce Bax and Bak activation during the process of cell death (42,43).

Leflu and Teri inhibit the mitochondrial enzyme DHODH which regulates the biosynthesis of pyrimidine nucleotides. Several studies showed an antiproliferative effect of these two drugs for multiple solid and liquid tumors (9). SBC3 and SBC5 cells had elevated levels of DHODH compared with non-malignant BEAS2B cells. The measurement of pyrimidine substances after Teri/Carbo treatment of SBC3 cells showed significantly and synergistically reduced the levels of DNA bases. However, there were no significant effects for SBC5 cells, but we observed decreases in several molecules with Teri/Carbo treatment. Pyrimidine metabolism affects the aggressive behavior of epithelial and non-epithelial tumors by increasing the EMT phenotype (57). Pyrimidine metabolic signature associated with EMT was found in 978 human cancer cell lines and demonstrated the importance of its catabolic products (58). The oncogenic role of the pyrimidine metabolites can be associated with the release of intracellular and extracellular substances from tumor cells and act as receptor ligands of purine molecules in the tumor microenvironment (59). Our findings on the inhibition of DRP1 phosphorylation at $Ser^{616}$ and reduction of purine and pyrimidine concentrations in SBC3 cells hypothesize the crosstalk of pyrimidines with mitochondrial fission proteins in SCLC. Indeed, knockdown of DRP1 in SBC3 and SBC5 cells significantly suppressed clone proliferation.

NanoString analyses of 16 metabolic and mitochondrial genes showed that knockdown of DNM1L significantly depleted expressions of nine genes in SBC3 cells; among them were mitochondrial MFN1, COX4IL, COX14, ATP51D, and metabolic MYC, MAPK1, CAD, and TIGAR. Downregulation of CAD by DNM1L-KO confirmed the possibility of crosstalk pyrimidine de novo pathway and mitochondrial fission in SBC3 cells. Interestingly, mitochondrial fusion is required for innate immune signaling and is regulated through DHODH inhibition (60). The viral infection limits the IFN response by promoting DRP1 phosphorylation and mitochondrial fission (61). ATP5BKO cells had mitochondria without cristae (62), which may affect mitochondria shape and morphology. In parallel with Teri/Carbo treatment we also tested Teri/Lur combination in 2D and 3D SCLC cell cultures. Interestingly, we observed a synergistic effect only in SCLC spheroids. Only a few studies compared effects of drug combinations between the two culture formats. Very low concentrations of ~0.8-3.2 μM Lur were used in combination treatment 100 times less than the peak Lur plasma concentrations reported in a clinical trial (63). Even with a low dose range of Teri/Lur treatment, the level of DRP1 phosphorylation at $Ser^{616}$ was significantly inhibited in H446 and SBC3 spheroids. Furthermore, Teri/Lur reduced RNA poly II activity and increased levels of DNA damage and replication stress proteins like γH2AX and pChk1($Ser^{345}$). Correspondingly, several studies reported DNA damage response markers in SCLC cell lines after a combination of ceralasertib/berzosertib with lurbinectedin treatment (64) or ONC201/Lur (65). Mitochondrial dynamics respond to various stressors and regulate ROS, pro-apoptotic molecules, metabolic intermediates, and ATP. Mitochondrial ROS is known to have dual action in cancer where elevated concentrations affect cell survival and increase cell death, and at lower concentrations, ROS acts as signaling molecules that mediate redox signaling events beneficial to tumor progression. ROS is a DNA damage mediator whose accumulation induces mitochondrial DNA degradation. We found amplification of mitochondrial superoxide (ROS) levels in H446 spheroids due to Teri/Lur treatment inducing mitochondrial depolarization and cell death. We also observed that Lur synergized with Teri and decreased ATP concentration more effectively than Lur-only treatment, as published recently for single Lur treatment (66). Finally, we detected mitochondrial fragmentation decreased in H446 spheroids treated with Teri and Teri/Lur using Imaris Surfaces and Cells parameters optimized for SCLC cells. Thus, Leflu/Lur treatment regressed mouse tumor growth by inhibiting DRP1 activation and the pyrimidine salvage pathway. Phenotypic synergy of Teri/Lur was confirmed by GSEA analysis. RNA-seq results using cancer hallmark collection showed significant upregulation of apoptosis through activation of the p53 pathway and down-regulation of cellular communication and motility, angiogenesis, and metabolic function genes.

Considered together, the present study indicates that targeting the fragmented mitochondrial network of SCLC tumors with high expression of DRP1 can re-sensitize tumors that are resistant.

References for Example 1

1. Koinis F, Kotsakis A, Georgoulias V. *Transl Lung Cancer Res* 2016; 5:39-50. 2. Subbiah S, Nam A, Garg N, Behal A, Kulkarni P, Salgia R. *J Clin Med* 2020; 9. 3. Rudin C M, Ismaila N, Hann C L, Malhotra N, Movsas B, Norris K, et al. *J Clin Onco* 2015; 33:4106-11. 4. American Cancer Society. [cited 2022 Sep. 9] Available from: http://www.cancer.org/acs/groups/content/@editorial/documents/document/acspc-044552.pdf. 5. Lennon F E, Cianci G C, Kanteti R, Riehm J J, Arif Q, Poroyko V A, et al. *Sci Rep* 2016; 6:24578. 6. Grieco J P, Allen M E, Perry J B, Wang Y, Song Y, Rohani A, et al. *Front Oncol* 2020; 10:600113. 7. Kashatus D F. *Biochem Biophys Res Commun* 2018; 500:9-16. 8. Tsuyoshi H, Orisaka M, Fujita Y, Asare-Werehene M, Tsang B K, Yoshida Y. *BMC Cancer* 2020; 20:467. 9. Miret-Casals L, Sebastian D, Brea J, Rico-Leo E M, Palacin M, Fernandez-Salguero P M, et al. *Cell Chem Biol* 2018; 25:268-78 e4. 10. Yu M, Nguyen N D, Huang Y, Lin D, Fujimoto T N, Molkentine J M, et al. *JCI Insight* 2019; 5. 11. Xie L, Zhou T, Xie Y, Bode A M, Cao Y. *Front Oncol* 2021; 11:769036. 12. Arrieta O, Lara-Mejia L, Zatarain-Barron Z L. *Lancet Oncol* 2020; 21:1132-4. 13. Dumoulin D W, Cantini L, Cornelissen R, Vink M, Klaase L, Slooff K, et al. *Eur J Cancer* 2022; 172:357-66. 14. Christensen C L, Kwiatkowski N, Abraham B J, Carretero J, Al-Shahrour F, Zhang T, et al. *Cancer Cell* 2014; 26:909-22. 15. Mirzapoiazova T, Xiao G, Mambetsariev B, Nasser M W, Miaou E, Singhal S S, et al. *Mol Cancer Ther* 2021; 20:1820-35. 16. Jones M H, Virtanen C, Honjoh D, Miyoshi T, Satoh Y, Okumura S, et al. *Lancet* 2004; 363:775-81. 17. Edgar R, Domrachev M, Lash A E. *Nucleic Acids Res* 2002; 30:207-10. 18. Lim N, Tesar S, Belmadani M, Poirier-Morency G, Mancarci B O, Sicherman J, et al. Curation of over 10,000 transcriptomic studies to enable data reuse. *Database* 2021. 19. Ritchie M E, Phipson B, Wu D, Hu Y, Law C W, Shi W, et al. *Nucleic Acids Res* 2015; 43:e47. 20. Rosner B. Fundamentals of biostatistics. Boston, M A: Cengage Learning; 2016. 21. Chen S, Zhou Y, Chen Y, Gu *J. Bioinformatics* 2018; 34:i884-i90. 22. Dobin A, Davis C A, Schlesinger F, Drenkow J, Zaleski C, Jha S, et al. *Bioinformatics* 2013; 29:15-21. 23. Liao Y, Smyth G K, Shi W. *Nucleic Acids Res* 2013; 41:e108. 24. Love M I, Huber W, Anders S. *Genome Biol* 2014; 15:550. 25. Wu T, Hu E, Xu S, Chen M, Guo P, Dai Z, et al. *Innovation* 2021; 2:100141. 26. Pellattiero A, Scorrano L. *Cell Chem Biol* 2018; 25:231-3. 27. Yu D D, Andrali S S, Li H, Lin M, Huang W, Forman B M. *Bioorg Med Chem* 2016; 24:3986-93. 28. Bar-Or A, Pachner A, Menguy-Vacheron F, Kaplan J, Wiendl H. *Drugs* 2014; 74:659-74. 29. Fragoso Y D, Brooks J B. *Expert Rev Clin Pharmacol* 2015; 8:315-20. 30. Cheng L, Wang H, Wang Z, Huang H, Zhuo D, Lin J. *Drug Des Devel Ther* 2020; 14:1897-908. 31. Jiang L, Zhang W, Li W, Ling C, Jiang M. *Toxicol Lett* 2018; 282:154-65. 32. Lennon F E, Salgia R. *Expert Opin Investig Drugs* 2014; 23:675-92. 33. Poroyko V, Mirzapoiazova T, Nam A, Mambetsariev I, Mambetsariev B, Wu X, et al. *Oncotarget* 2018; 9:19793-806. 34. Lima A R, Correia M, Santos L, Tavares C, Rios E, Canberk S, et al. *Endocrine* 2021; 73:85-97. 35. Li L, Ng S R, Colón C I, Drapkin B J, Hsu P P, Li Z, et al. *Sci Transl Med* 2019; 11. 36. Ma Y, Wang L, Jia R. *Am J Cancer Res* 2020; 10:1278-93. 37. Hu J, Zhang H, Li J, Jiang X, Zhang Y, Wu Q, et al. *J Exp Clin Cancer Res* 2020; 39:37. 38. Gundamaraju R, Lu W, Manikam R. *Cancers* 2021; 13. 39. Grasso D, Zampieri L X, Capelôa T, Van de Velde J A, Sonveaux P. *Cell Stress* 2020; 4:114-46. 40. Anderson G R, Wardell S E, Cakir M, Yip C, Ahn Y R, Ali M, et al. *Nat Commun* 2018; 9:1677. 41. Gibbons D L, Byers L A, Kurie J M. *Mol Cancer Res* 2014; 12:3-13. 42. Hu W, Wang F, Tang J, Liu X, Yuan Z, Nie C, et al. *J Biol Chem* 2012; 287:68-80. 43. Wang J, Guo W, Zhou H, Luo N, Nie C, Zhao X, et al. *Oncotarget* 2015; 6:17192-205. 44. Santamaria Nunez G, Robles C M, Giraudon C, Martinez-Leal J F, Compe E, Coin F, et al. *Mol Cancer Ther* 2016; 15:2399-412. 45. Zhou Z, Sun B, Nie A, Yu D, Bian M. *Front Cell Dev Biol* 2020; 8:599765. 46. Zhang Q, Xiong D, Pan J, Wang Y, Hardy M, Kalyanaraman B, et al. *Cancers* 2022; 14. 47. Gomes A P, Ilter D, Low V, Drapela S, Schild T, Mullarky E, et al. *Nat Metab* 2022; 4:435-43. 48. Zhou Y, Tao L, Zhou X, Zuo Z, Gong J, Liu X, et al. *Cancer Metab* 2021; 9:22. 49. Rehman J, Zhang H J, Toth P T, Zhang Y, Marsboom G, Hong Z, et al. *FASEB Journal* 2012; 26:2175-86. 50. Yu L, Xiao Z, Tu H, Tong B, Chen S. *Medicine* 2019; 98:e18228. 51. Tusskorn O, Khunluck T, Prawan A, Senggunprai L, Kukongviriyapan V. *Biomed Pharmacother* 2019; 111:109-18. 52. Zhu S, Yan X, Xiang Z, Ding H F, Cui H. *PloS one* 2013; 8:e71555. 53. Buettner R, Morales C, Wu X, Sanchez J F, Li H, Melstrom L G, et al. *Mol Ther Oncolytics* 2019; 14:149-58. 54. Mirzapoiazova T, Li H, Nathan A, Srivstava S, Nasser M W, Lennon F, et al. *J Clin Med* 2019; 8. 55. Picard M, Sandi C. *Neurosci Biobehav Rev* 2021; 120:595-610. 56. *Yapa* NMB, Lisnyak V, Reljic B, Ryan M T. *FEBS Lett* 2021; 595:1184-204. 57. Siddiqui A, Ceppi P. *Mol Metab* 2020; 35:100962. 58. Shaul Y D, Freinkman E, Comb W C, Cantor J R, Tam W L, Thiru P, et al. *Cell* 2014; 158: 1094-109. 59. Schneider G, Glaser T, Lameu C, Abdel-baset-Ismail A, Sellers Z P, Moniuszko M, et al. *Mol Cancer* 2015; 14:201. 60. Bahat A, MacVicar T, Langer T. *Front Cell Dev Biol* 2021; 9:720490. 61. Yasukawa K, Kinoshita D, Yaku K, Nakagawa T, Koshiba T. *J Biol*

*Chem* 2020; 295:444-57. 62. Bajzikova M, Kovarova J, Coelho A R, Boukalova S, Oh S, Rohlenova K, et al. *Cell Metab* 2019; 29:399-416 e10. 63. Trigo J, Subbiah V, Besse B, Moreno V, Lopez R, Sala M A, et al. *Lancet Oncol* 2020; 21:645-54. 64. Kundu K, Cardnell R J, Zhang B, Shen L, Stewart C A, Ramkumar K, et al. *Transl Lung Cancer Res* 2021; 10:4095-105. 65. Liguori N R, Sanchez Sevilla Uruchurtu A, Zhang L, Abbas A E, Lee Y S, Zhou L, et al. *Am J Cancer Res* 2022; 12:729-43. 66. Xie W, Forveille S, Iribarren K, Sauvat A, Senovilla L, Wang Y, et al. *Oncoimmunology* 2019; 8:e1656502.

Example 2

SCLC constitutes about 13% to 15.7% of all lung cancer cases (1,2). Majority of patients with SCLC have extensive-stage SCLC (ES-SCLC) with poor prognosis and survival (median survival 7.3 months; 2-year survival <5%) (3-6). Estimated deaths from SCLC are approximately 4% of all cancer mortality. Standard of care for newly diagnosed ES-SCLC has been platinum-based chemotherapy in combination with etoposide but most patients experience progression of disease eventually. In the last few years, anti-PDL1 antibody (atezolizumab or durvalumab) has been approved in combination with chemotherapy for first-line treatment of ES-SCLC (7,8). However, even with the addition of checkpoint inhibitor, the 1-year progression-free survival (PFS) is still less than 20% (7,8). Thus, many patients with ES-SCLC experience progression by the one-year mark. ES-SCLC is generally unresponsive to chemotherapy at relapse (9). Topotecan, a topoisomerase-I inhibitor, is the longest approved drug for more than 20 years for treating SCLC in the second-line setting. Reported ORR with topotecan is 24%, median PFS is 3.4 months; however, its use is limited by its significant toxicity and difficult schedule of administration (10). Other drugs approved in the second line setting and beyond are lurbinectedin and tarlatamab-dlle, both of which have received accelerated approvals within the last 5 years. There is a need to investigate novel drugs and combinations in this setting to improve patient outcomes.

Lurbinectedin

Lurbinectedin, an RNA-polymerase II inhibitor was approved in 2020 for the treatment of relapsed or refractory SCLC and has better tolerability than topotecan but use is limited by modest clinical benefit with lack of durable responses (ORR 32.7%; median PFS 3.5 months) (11). Lurbinectedin has a direct cytotoxic effect on tumor cells by blocking the binding of oncogenic transcription factors to their target sequences and promotes the irreversible proteasomal degradation of RNA polymerase II (12).

Leflunomide

Leflunomide is a commercially available oral immunosuppressive agent that has been FDA approved since 1998 for the treatment of rheumatoid arthritis as a single agent or in combination with methotrexate (13,14). Leflunomide is generally well-tolerated and may be taken over a long period of time. The primary mechanism of action through its active metabolite, teriflunomide, is the inhibition of de novo pyrimidine synthesis by targeting dihydroorotate dehydrogenase (DHODH), leading to an anti-proliferative effect on B and T lymphocytes (15). DHODH is an inner mitochondrial membrane enzyme that catalyzes the fourth step in the de novo synthesis of pyrimidines (16). Depletion of pyrimidine pools induced by the DHODH inhibitors such as leflunomide and teriflunomide promotes mitochondrial elongation through induction of the mitochondrial proteins MFN1 and MFN2 (17). Moreover, leflunomide represses the mitochondrial fission protein Dynamin-related protein 1 (DRP1) (17). Thus, leflunomide significantly regulates cell mitochondrial morphology and function and therefore, has the portal to be used as a repurposed chemotherapeutic drug.

DRP1 and Mitochondrial Function in SCLC

Several studies in the past have associated mitochondrial fragmentation with tumor progression in multiple cancers such as mesothelioma, ovarian, breast, lung, and pancreatic cancer (18,19). Both mitochondrial fragmentation (fission) and elongation (fusion) are responsible for maintaining proper morphology. However, the rapid proliferation of cancer cells resulting from their constant growth and metabolic shifts triggers mitochondrial fragmentation (20). DRP1 plays a central role in mitochondrial fission and fusion regulation. Notably, its phosphorylation at site Ser616 (fission) leads to activation, while at Ser637 (fusion) leads to inactivation (21).

Abnormal expression of DRP1, observed in different tumor types, affects cancer progression through cell proliferation, mitochondrial dynamics, cell apoptosis, and cell cycle regulation (22). Increasing evidence suggests that targeting DRP1 to suppress mitochondrial fission may be a new strategy to treat SCLC as DRP1 is upregulated in human small cell carcinoma (23,24). A recent study showed that mRNA DRP1 level increased two-fold in SCLC tissue compared with control and reported a correlation between high expression of DRP1 with poor survival probability for males and females (24). Pharmacological inhibition of DRP1 activity promoted cell cycle arrest and apoptosis in lung cancer cells (22).

Our preclinical studies have provided strong evidence supporting our hypothesis that leflunomide may be an effective drug for treating SCLC by targeting DRP1 and suppressing mitochondrial fission may be a new strategy to treat SCLC. In experiments performed on SBC5 SCLC cell line, we found that Teriflunomide, the active metabolite of leflunomide, significantly inhibits DRP1 phosphorylation at Ser616 and Ser637, but DRP1 expression level is unaffected after treatment (FIG. 2C). Although mitochondrial areas of SBC5 cells were not affected with treatment, elongations of individual mitochondria were detected with each treatment. Altogether, these data suggest that targeting DRP1 with Teri decreased phosphorylation at Ser616 and affected mitochondrial morphology.

Experiments show increased efficacy of the combination of Leflunomide/Teriflunomide and lurbinectedin in vitro and in vivo. In SBC3 mouse xenograft model for SCLC, both Leflunomide and Lurbinectidin alone, as well as the combination significantly reduced tumor growth over time compared to the control. The combination was more effective than either drug alone (~84% as compared to 22% with Leflunomide alone and 39% with Lurbinectedin alone; FIG. 6I).

Spheroid cultures were used as a second model to validate the synergistic effect of Teriflunomide/Lurbinectedin treatment on SCLC cell viability and apoptosis. SBC3 spheroids were more sensitive for the combination and responded synergistically with $CI_{50}$ value 0.0072. The combination inhibited RNA polymerase II activity and increased the level of DNA damage and of replication stress proteins like γH2AX and pChk1(Ser345). Inhibition of pDRP1 was also increased with treatment with the combination. Hence, the results from these comprehensive experiments reveal that pharmacological inhibition of DRP1 and DHODH with combinations of Leflunomide and Lurbinectedin accelerated cell death by reducing DRP1 activity, pyrimidine synthesis, and impeded mitochondrial fragmentation.

We disclose herein, inter alia, a Phase I clinical trial to identify the maximum tolerated dose (MTD) of combination therapy with lurbinectedin and leflunomide in patients with metastatic pre-treated SCLC. The primary goal is to establish the safety and tolerability of the combination (Specific Aim 1). Pharmacology is performed to characterize the relationship between serum concentration of the active leflunomide metabolite, teriflunomide, and disease response (Specific Aim 2). In addition, we also evaluate the impact of combination therapy on mitochondrial biomarkers in blood and tumors (Specific Aim 3). Our central hypothesis is that leflunomide synergizes with lurbinectedin via modulation of mitochondrial fission and morphology for SCLC.

The FDA-approved dose for leflunomide in adults for the treatment of rheumatoid arthritis is a loading dose of 100 mg orally once daily for 3 days, followed by a maintenance dose of 10 to 20 mg orally once daily. Leflunomide has been used at up to 40 mg/day in patients with Wegner's granulomatosis with a safety profile like the 20 mg/day dose used in rheumatoid arthritis (25). A loading dose of 100 mg for 3 days is used to facilitate rapid attainment of steady state levels. Without a loading dose, it is estimated that attainment of steady state concentrations would require nearly two months of dosing (Leflunomide FDA label). Leflunomide (the pro-drug) is rapidly converted to its active primary metabolite teriflunomide, which mediates leflunomide's pharmacologic activity. Therefore, in the proposed trial, we will start leflunomide with a loading dose of 100 mg daily for 3 days followed by maintenance dose of 10 mg daily and this will be then investigated at higher doses using a dose-escalation 3+3 design. Lurbinectedin will be administered at the approved standard of care dose of 3.2 mg/m$^2$ every 3 weeks.

Figure 14:
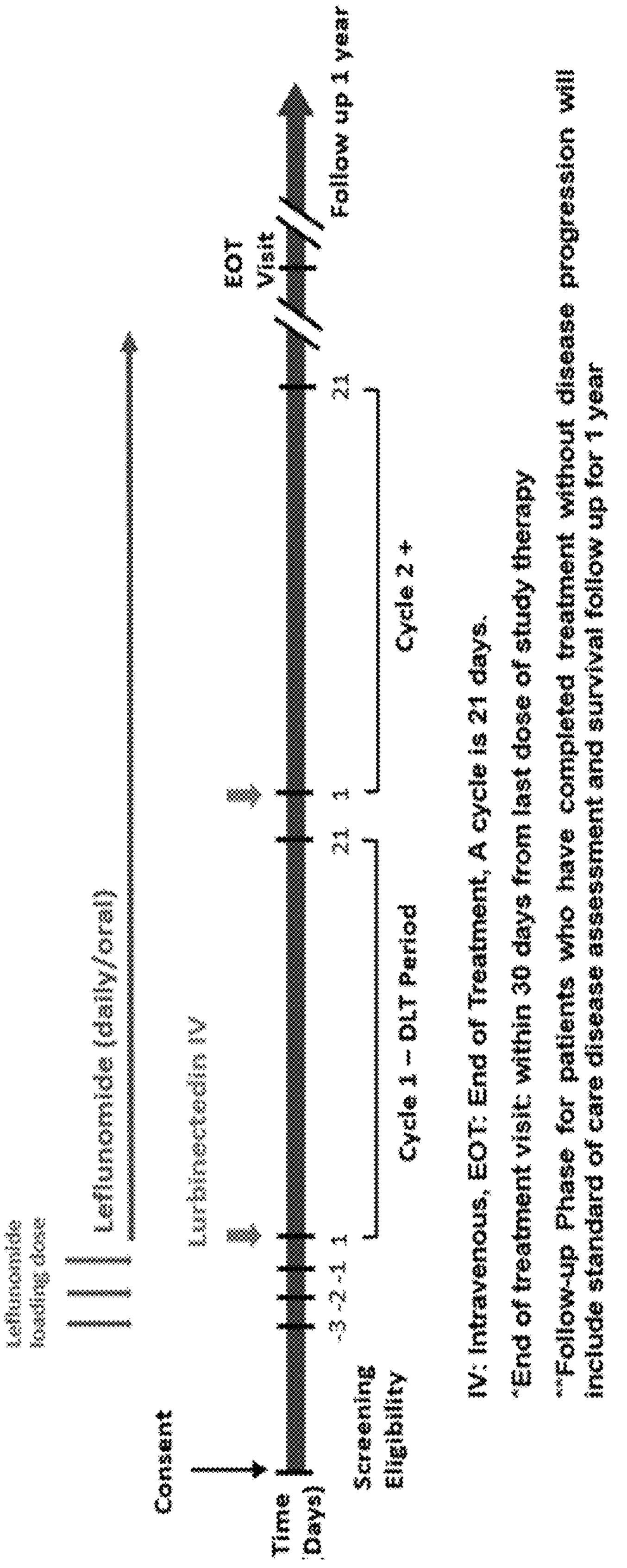
FIG. 14. Phase I trial schema.
Figure 15:
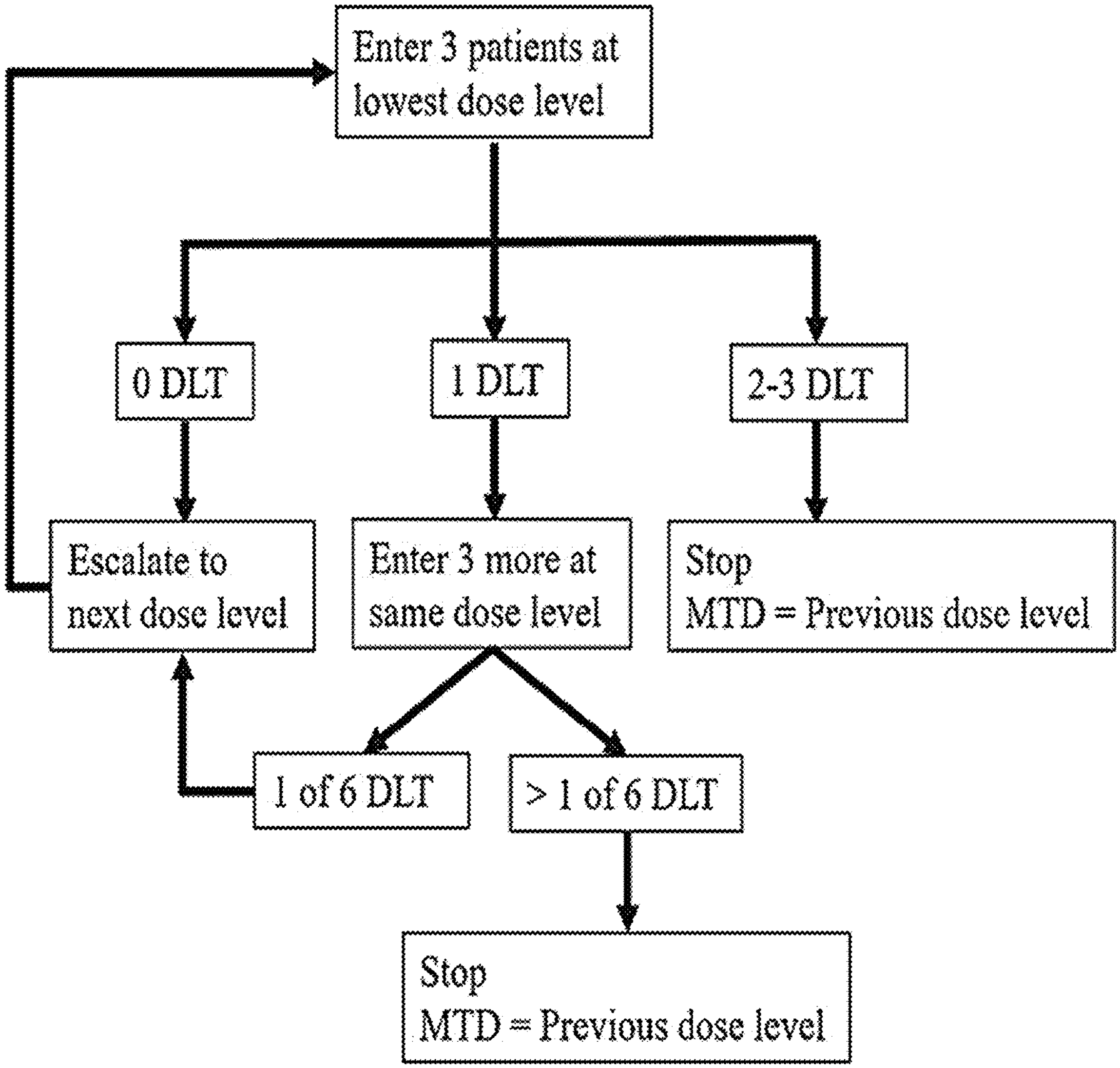
FIG. 15. Phase I dose-escalation trial schema.

Phase I trial design. Patients diagnosed with recurrent or refractory SCLC with disease progression on or after prior chemoimmunotherapy will be enrolled in the trial using the standard 3+3 design during the dose-escalation (FIG. 14). All cycles will be 21 days. The dose of lurbonectedin will be fixed at 3.2 mg/m$^2$ every 3 weeks which is the standard dose for this drug. Leflunomide will be given on days −3 to −1 at the loading dose of 100 mg per day. Patients will then start on maintenance dose using the drug escalation levels as per Table 4 from day 1 of cycle. A total of approximately 15 patients are expected to be accrued to establish the maximum tolerated dose (MTD). An expansion cohort of an additional 6-10 patients may be enrolled at the MTD to confirm safety.

Patient eligibility. Patients will be required to have: 1) relapsed or refractory SCLC; 2) ≥18 years of age with an ECOG performance status of ≤2; and 3) received at least one prior line of platinum-based chemotherapy. Patients will be excluded from trial if they have symptomatic or active (new or progressive) brain metastases or known leptomeningeal disease.

Trial treatment: Eligible patients will receive lurbinectedin and leflunomide on a 21-day cycle.

- On Days −3, −2 and −1 (for cycle 1 only), patients will receive loading dose of leflunomide (100 mg)
- On day 1 of each cycle, patients will receive lurbinectedin intravenously.
- On days 1 to 21 of each cycle, patients will receive lurbinectedin oral once daily as per the dose escalation schema.

TABLE 4

The dosing of the treatment regimen will be as per the dose escalation levels.

| Dose level | Lurbinectedin (Day 1 of each cycle) | Leflunomide loading (pre-cycle 1) | Leflunomide (post-load; C1D1 onwards) |
|---|---|---|---|
| Level −1 | 3.2 mg/m$^2$ | 100 mg Days −3, −2, −1 | 10 mg every other day |
| Level 1 (start) | 3.2 mg/m$^2$ | 100 mg Days −3, −2, −1 | 10 mg daily |
| Level 2 | 3.2 mg/m$^2$ | 100 mg Days −3, −2, −1 | 20 mg daily |
| Level 3 | 3.2 mg/m$^2$ | 100 mg Days −3, −2, −1 | 30 mg daily |

Trial endpoints: The primary endpoint of the trial will be to determine the MTD and recommended phase II dose (RP2D) of the combination of lurbinectedin and leflunomide for the treatment of recurrent or refractory SCLC. The secondary endpoint will be to measure clinical responses at all dose levels using RECIST v 1.1.

Duration of treatment/study: The treatment will continue until evidence of radiographic progression, unequivocal clinical progression, unacceptable side effects, withdrawal of consent, or death.

Duration of follow-up: A safety follow-up visit should occur when subjects permanently stop study treatment and should be performed 30 days (±7 days) after the last dose of treatment. Patients will be followed at least every 3 months (±7 days) for survival for up to two years following their Safety Follow up visit. This follow-up may be via phone calls and through review of medical records. Patients removed from study for unacceptable adverse event(s) will also be followed until resolution or stabilization of the adverse event.

Specific Aim 1: To identify the MTD of leflunomide in combination with lurbinectedin for the treatment of patients with metastatic SCLC (n=15) who have progressed on prior platinum-based chemotherapy. The goal of this aim will be to test the safety and tolerability of this combination. Patients will receive escalating doses of leflunomide using 3+3 design starting from level 1 (10 mg oral daily).

For safety and tolerability, the MTD will be defined as the highest dose level at which one or no patient develops a dose limiting toxicity (DLT) out of a cohort of 6 patients. Toxicities will be described at all dose levels using the National Cancer Institute Common Toxicity Criteria for Adverse Events (NCI CTCAE) v 5.0. All patients will be monitored for the first 21 days of treatment for DLT during the dose-escalation. All patients in the dose-escalation part who receive 1 cycle of therapy will be evaluable for DLT. Patients who experience DLT within the first 21 days of treatment and drop out of the study will be considered evaluable for DLT and will not be replaced. Patients who drop out of the study for reasons other than DLT will be considered not evaluable and will be replaced.

DLT Definition

A DLT will be defined as any of the following treatment-related adverse events (AEs) or laboratory abnormalities, graded according to NCI CTCAE v 5:

- Grade 4 thrombocytopenia with clinically significant bleeding or grade 4 thrombocytopenia lasting more than 7 days and/or requiring a platelet transfusion.
- Grade 4 neutropenia lasting more than 7 days or any-grade febrile neutropenia. In the event of Grade 4 neutropenia, a full blood count must be performed no more than 7 days after the onset of the event to determine if a DLT has occurred.

≥Grade 3 hypersensitivity reaction (unless first occurrence and resolves within 8 hours with appropriate clinical management).

Treatment delay >7 days secondary to recovery from study drug-related toxicity.

≥Grade 3 non-hematologic treatment-related toxicity lasting more than 72 hours despite optimal supportive care.

≥Grade 3 elevation in bilirubin or transaminases

≥Grade 3 fatigue

Inability to take at least 80% of planned leflunomide doses during cycle 1.

The following events will be excluded from the DLT definition:

Any AE≥grade 3 clearly determined to be unrelated to study drug(s) (e.g., disease progression)

≥Grade 3 isolated alkaline phosphatase laboratory abnormality of any duration

≥Grade 3 asymptomatic laboratory abnormality of any duration that does not require any clinical intervention or hospitalization.

Specific Aim 2: To determine the correlation between levels of the active leflunomide metabolite, teriflunomide and disease response by collecting serial serum samples from the patients enrolled on the trial.

Teriflunomide analysis. Total and free Teriflunomide plasma concentrations will be determined using an LC-MS/MS method based on an assay that has been validated over a wide dynamic concentration range of 10-4000 ng/mL (59). Following LC/MS/MS analysis, serum concentrations of Teriflunomide will be quantified. Non-compartmental PK analyses of Teriflunomide will be used to determine the average steady-state total and free Teriflunomide trough concentrations (Ctrough). Ctrough results will be summarized within and between participants using means and standard deviations. At the end of the study, total and free Teriflunomide levels will be summarized at 2- and 4-week sampling time points. Blood samples will be collected during cycle 1, cycle 2 and at progression.

Tumor response assessments. Disease response will be assessed as specified in RECIST v 1.1 guidelines. During study treatment, disease status will be assessed every 8 weeks (±7 days) using CT scan of the abdomen/pelvis, CT of the chest, or additional staging as required for each patient. Tumor responses will be correlated with Teriflunomide plasma concentrations.

Specific Aim 3: To determine the pharmacodynamic effects of combination therapy tumor mitochondrial biomarkers in patients enrolled on trial therapy in Aim 1 by collecting pre- and post-treatment tumor biopsies.

Tumor tissue analysis. For each patient enrolled, two research biopsy will be performed at pre-treatment (if archived tissue not available) and after cycle 3. Tumor samples obtained from patients will be formalin-fixed and paraffin embedded (FFPE) and prepared for routine IHC. The second biopsy tissue will be sent to the Salgia lab for tissue processing and development of PDXs. In addition to biopsy, fluid from malignant pleural effusions can also be processed for isolating cancer cells and cultured in the lab. The pleural fluid samples will be collected and processed from the patients prior to treatment as well as during treatment if possible. Slides will be stained with hematoxylin and eosin (H&E) and for DRP1 and DHODH expression using IHC. Expression will be quantified as ranging from 0 to 3 using a semi-quantitative visual index. Slides will also be stained with pDRP1 Ser616 antibody (2oab Alexa488), and the phosphorylation level will be analyzed with QuPath 0.2.0M9 software.

ctDNA analysis. DNA will be extracted from the whole blood collected in Streck cfDNA tubes pre-treatment, C3D1 and at progression. This blood will be analyzed for mutations using next-generation sequencing of cell-free DNA. Circulating tumor (ct) DNA will be analyzed using the Guardant360® platform (Guardant Health, Redwood City, CA). Guardant360® sequences 83 cancer-associated genes to identify somatic alterations; all exons are sequenced in some genes; only clinically significant exons are sequenced in other genes. The types of genomic alterations detected by Guardant360® include single nucleotide variants (SNVs), gene amplifications, fusions, short insertions/deletions (indels, longest detected, 70 base pairs), splice site disrupting events, microsatellite instability, and tumor mutation burden. Given the limited number of genomic alterations that are expected and the limited number of enrolled patients, the results will be described in a descriptive fashion, with a focus on the identification of potential mechanisms of resistance to treatment. Changes in mutation allele frequency before and after study treatment will be described. The Guardant360® assay is a commercially available assay and will be ordered as a standard care assay in this study.

Statistical Analysis

Descriptive statistics will be used for all safety, efficacy, immunogenicity, and PK parameters. Data will be summarized using descriptive statistics (number of subjects, mean, median, standard deviation, minimum, and maximum) for continuous variables and summarized using frequencies and percentages for categorical variables. Time-to-event distributions (PFS, DOR) will be estimated using the Kaplan-Meier method. All data collected will be presented in subject listings. All data will be summarized overall and by dose level received. Response rate endpoints will be summarized by dose levels, number, and percentage, along with Clopper-Pearson exact binomial confidence intervals. Correlative endpoints (described below) will be compared between pre-treatment and post-treatment samples. Differences in paired samples will be calculated and compared with Wilcoxon rank sum test or using generalized linear mixed models as applicable. Simple and classical approaches will be used to handle missing data based on the assumption that missing data are random and noninformative. Descriptive statistics will be used to characterize possible inter-patient variability and relationship to tolerability/toxicity, and response for future studies. In addition, the specific time trend for Teriflunomide serum concentration over the course of treatment will be assessed using linear mixed effects modeling. The overall fit of the model will be evaluated graphically by taking a scatter plot of data and applying an overlay of the line generated by the model. Similar modeling techniques will be used to assess the impact of serum concentration on clinical events (e.g., toxicity and disease response).

References for Example 2

1. Govindan, R., et al., J Clin Oncol, 2006. 24(28): p. 4539-44. 2. Gaspar, L. E., et al., Clin Lung Cancer, 2012. 13(2): p. 115-22. 3. Jhun, B. W., et al., Lung Cancer, 2013. 81(1): p. 65-70. 4. Powell, H. A., et al., Br J Cancer, 2014. 110(4): p. 908-15. 5. Murray, N. and A. T. Turrisi, 3rd, J Thorac Oncol, 2006. 1(3): p. 270-8. 6. Chute, J. P., et al., J Clin Oncol, 1999. 17(6): p. 1794-801. 7. Horn, L., et al., N Engl J Med, 2018. 379(23): p. 2220-2229. 8. Paz-Ares, L., et al., Lancet, 2019. 394(10212): p. 1929-1939. 9. Gazdar, A. F., P. A. Bunn, and J. D. Minna, Nat Rev Cancer, 2017. 17(12): p. 725-737. 10. Schiller, J. H., et al., J Clin Oncol, 1996. 14(8): p. 2345-52. 11. Trigo, J., et al., Lancet Oncol, 2020. 21(5): p. 645-654. 12. Dumoulin, D. W., et al., Eur J Cancer, 2022. 172: p. 357-366. 13. Fragoso, Y. D. and J. B. Brooks, Expert Rev Clin Pharmacol, 2015. 8(3): p. 315-20. 14. Alfaro-Lara, R., et al., Reumatol Clin (Engl Ed), 2019. 15(3): p. 133-139. 15. Herrmann, M. L., R. Schleyerbach, and B. J. Kirschbaum, Immunopharmacology, 2000. 47(2-3): p. 273-89. 16. Cherwinski, H. M., et al., Inflamm Res, 1995. 44(8): p. 317-22. 17. Miret-Casals, L., et al., Cell Chem Biol, 2018. 25(3): p. 268-278 e4. 18. Lennon, F. E., et al., Sci Rep, 2016. 6: p. 24578. 19. Grieco, J. P., et al., Front Oncol, 2020. 10: p. 600113. 20. Kashatus, D. F., Biochem Biophys Res Commun, 2018. 500(1): p. 9-16. 21. Tsuyoshi, H., et al., BMC Cancer, 2020. 20(1): p. 467. 22. Rehman, J., et al., FASEB J, 2012. 26(5): p. 2175-86. 23. Mirzapoiazova, T., et al., J Clin Med, 2019. 8(10). 24. Yu, L., et al., Medicine (Baltimore), 2019. 98(48): p. e18228. 25. Metzler, C., et al., Rheumatology (Oxford), 2004. 43(3): p. 315-20.

What is claimed is:

1. A method of treating small cell lung cancer in a subject in need thereof, said method comprising administering to the subject a combined effective amount of a first agent and a second agent, wherein the first agent is leflunomide or teriflunomide and the second agent is lurbinectedin or carboplatin, and wherein the combined effective amount is a combined synergistically effective amount.

2. The method of claim 1, wherein the first agent is leflunomide.

3. The method of claim 1, wherein the first agent is teriflunomide.

4. The method of claim 1, wherein the first agent is administered orally.

5. The method of claim 1, wherein the first agent is administered at a dose of about 10 mg.

6. The method of claim 1, wherein the first agent is administered at a dose of about 20 mg.

7. The method of claim 1, wherein the first agent is administered at a dose of about 30 mg.

8. The method of claim 1, wherein the second agent is lurbinectedin.

9. The method of claim 8, wherein lurbinectedin is administered intravenously at a dose of from about 1 $mg/m^2$ to about 5 $mg/m^2$ over 60 minutes.

10. The method of claim 8, wherein lurbinectedin is administered intravenously at a dose of about 3.2 $mg/m^2$ over 60 minutes.

11. The method of claim 1, wherein the second agent is carboplatin.

12. The method of claim 11, further comprising administering etoposide, atezolizumab, or durvalumab.

* * * * *